United States Patent [19]
Summers, Jr. et al.

[11] Patent Number: 5,998,194
[45] Date of Patent: Dec. 7, 1999

[54] POLYKETIDE-ASSOCIATED SUGAR BIOSYNTHESIS GENES

[75] Inventors: Richard G. Summers, Jr., Nashotah, Wis.; Leonard Katz, Wheeling, Ill.; Stefano Donadio, Varese, Italy; Michael J. Staver, Grayslake, Ill.

[73] Assignee: Abbott Laboratories, Abbott Park, Ill.

[21] Appl. No.: 08/576,626

[22] Filed: Dec. 21, 1995

[51] Int. Cl.⁶ .............................. C12N 1/20; C12N 9/00; C07H 21/04
[52] U.S. Cl. .................... 435/252.33; 435/200; 435/227; 435/228; 435/231; 435/252.3; 435/252.35; 435/320.1; 435/325; 435/419; 536/23.2
[58] Field of Search ..................................... 435/200, 227, 435/228, 231, 320.1, 252.3, 252.33, 325, 419, 252.35; 536/23.2

[56] References Cited

FOREIGN PATENT DOCUMENTS

| | | |
|---|---|---|
| 9116334 | 10/1991 | WIPO . |
| 9313663 | 7/1993 | WIPO . |
| 9508548 | 3/1995 | WIPO . |

OTHER PUBLICATIONS

Annu. Rev. Microbiol, Katz, et al., 1993, vol. 47:875–912, "Polyketide Synthesis, Prospects for Hybrid Antibiotics".

Annu. Rev. Genet, Hopwood, et al., 1990, vol. 24:37–66, "Molecular Genetics of Polyketides and its Comparision to Fatty Acid Biosynthesis".

Annu. Rev. Microbiol., Liu, et al., 1994, vol. 48:223–256, "Pathways and Mechanisms in the Biogenesis of Novel Deoxysugars by Bacteria".

Molecular Microbiology, Merson–Davies, et al., 1994, vol. 13(2):349–355, "Analysis of Five Tylosin Biosynthetic Genes from the tyIIBA region of the Streptomyces Fradiae Genome".

Journal of Bacteriology, Weber, et al., 1985, vol. 164(1):425–433, "Genetic Analysis of Erythromycin Production in Streptomyces Erythreus".

Journal of Bacteriology, Vara, et al., 1989, vol. 171(11):5872–5881, "Cloning of Genes govenring the Deoxysugar Portion of the Erythromycin Biosynthesis Pathway in *Saccharopolyspora Erythraea*(*Streptomyces Erythreus*)".

Journal of Bacteriology, Weber, et al., 1990, vol. 172(5):2372–2383, "Organization of a Clsuter of Erythromycin Genes in *Saccharopolyspora Erythraea*".

Industrial Microorganisms: Basic and Applied Molecular Genetics, Donadio, et al., 1993, pp. 257–265, "Recent Developments in the Genetics of Erythromycin Formation".

Science, Donadio et al., vol. 252:675–679, Modular Organozation of Genes Required for Complex Polyketide Biosynthesis; May 3, 1991.

Mol Gen Genet, Haydock, et al., 1991, vol. 230:120–128, "Cloning and Sequence Analysis of Genes Involved in Erythromycin Biosynthesis in *Saccharopolyspora Eryhtraea*: Sequence Similarities Between EryG and A Family of S–Adenosylmethionine–Dependent Methyltransferases".

Nature, Cortes, et al., 1990, vol 348:176–178, An Unusually Large Multifunctional Polypeptide in the Erthromycin–Producing Polyketide Synthase of *Saccharopolyspora Erythraea*.

*Primary Examiner*—Robert A. Wax
*Attorney, Agent, or Firm*—Dianne Castuto

[57] ABSTRACT

The present invention provides isolated polynucleotides from *Saccharomyces erythraea* that encode enzymes involved in the biosynthesis of polyketide-associated sugars. Methods of using the polynucleotides to produce novel glycosylation modified polyketides are also provided.

19 Claims, 45 Drawing Sheets

```
  1  CACGCCGACGCGATCGCGCGGCACATCGACGCCTGGCTGGGCGGAGGGAATTCATGACCA   60
                                                            M  T  T

61  CGACCGATCGCGCCGGGCTGGGCAGGCAGCTCCAGATGATCCGCGGCCTGCACTGGGGTT  120
      T  D  R  A  G  L  G  R  Q  L  Q  M  I  R  G  L  H  W  G  Y

121  ACGGCAGCAACGGCGACCCTTACCCGATGCTGCTGTGCGGACACGACGACGACCCGCAGC  180
      G  S  N  G  D  P  Y  P  M  L  L  C  G  H  D  D  D  P  Q  R

181  GCCGGTACCGCTCGATGCGCGAGTCCGGTGTGCGGCGCAGGACCGAGACGTGGGTGGTGG  240
      R  Y  R  S  M  R  E  S  G  V  R  R  R  T  E  T  W  V  V  A

241  CCGACCACGCCACCGCCCGGCAGGTGCTCGACGACCCCGCGTTCACCCGCGCCACCGGAC  300
      D  H  A  T  A  R  Q  V  L  D  D  P  A  F  T  R  A  T  G  R

301  GCACACCGGAATGGATGCGGGCCGCGGGCGCGCCACCCGCCGAGTGGGCCCAGCCGTTCC  360
      T  P  E  W  M  R  A  A  G  A  P  P  A  E  W  A  Q  P  F  R

361  GGGACGTGCACGCCGCGTCCTGGGAAGGCGAGGTCCCCGACGTCGGGGAACTGGCGGAGA  420
      D  V  H  A  A  S  W  E  G  E  V  P  D  V  G  E  L  A  E  S

421  GCTTCGCCGGTCTGCTCCCCGGCGCGGGCGCGCGGCTGGACCTGGTCGGCGACTTCGCCT  480
      F  A  G  L  L  P  G  A  G  A  R  L  D  L  V  G  D  F  A  W

481  GGCAGGTACCGGTGCAGGGCATGACCGCCGTGCTCGGCGCAGCCGGAGTGCTGCGCGGCG  540
      Q  V  P  V  Q  G  M  T  A  V  L  G  A  A  G  V  L  R  G  A

541  CCGCGTGGGACGCCCGCGTCAGCCTGGACGCCCAGCTCAGCCCGCAGCAGCTCGCGGTGA  600
      A  W  D  A  R  V  S  L  D  A  Q  L  S  P  Q  Q  L  A  V  T

601  CCGAAGCAGCGGTCGCGGCACTGCCCGCCGACCCCGCACTGCGCGCCCTGTTCGCCGGGG  660
      E  A  A  V  A  A  L  P  A  D  P  A  L  R  A  L  F  A  G  A

661  CCGAGATGACCGCGAACACCGTGGTCGACGCGGTCCTGGCCGTCTCGGCCGAACCGGGGC  720
      E  M  T  A  N  T  V  V  D  A  V  L  A  V  S  A  E  P  G  L

721  TGGCCGAACGGATCGCCGACGACCCCGCCGCCGCGCAGCGAACCGTCGCCGAGGTGCTGC  780
      A  E  R  I  A  D  D  P  A  A  A  Q  R  T  V  A  E  V  L  R

781  GCCTGCACCCGGCATTGCACCTGGAGCGGCGCACGGCCACCGCAGAGGTGCGGCTCGGCG  840
      L  H  P  A  L  H  L  E  R  R  T  A  T  A  E  V  R  L  G  E

841  AGCACGTGATCGGCGAAGGCGAGGAGGTCGTGGTCGTCGTCGCGGCGGCCAACCGCGACC  900
      H  V  I  G  E  G  E  E  V  V  V  V  V  A  A  A  N  R  D  P

901  CGGAGGTCTTCGCCGAGCCCGACCGCCTCGACGTGGACCGCCCCGACGCCGACCGCGCGC  960
      E  V  F  A  E  P  D  R  L  D  V  D  R  P  D  A  D  R  A  L
```

FIG. 4A-1

```
 961  TGTCGGCACATCGCGGCCACCCCGGCAGGCTGGAGGAGCTGGTCACCGCGCTCGCCACCG  1020
       S   A   H   R   G   H   P   G   R   L   E   E   L   V   T   A   L   A   T   A

1021  CCGCACTGCGGGCCGCGGCCAAGGCGCTGCCCGGACTCACGCCCAGCGGCCCGGTCGTCC  1080
       A   L   R   A   A   A   K   A   L   P   G   L   T   P   S   G   P   V   V   R

1081  GGCGCCGCCGATCACCCGTCCTGCGGGGAACCAACCGCTGCCCCGTCGAGCTCTGAGGAT  1140
       R   R   R   S   P   V   L   R   G   T   N   R   C   P   V   E   L   *

1141  TCCGCGATGCGCGTCGTCTTCTCCTCCATGGCCAGCAAGAGCCACCTCTTCGGCCTCGTC  1200
           M   R   V   V   F   S   S   M   A   S   K   S   H   L   F   G   L   V

1201  CCCCTCGCATGGGCGTTCCGCGCGGCGGGGCACGAGGTCCGCGTGGTCGCGTCCCCGGCG  1260
       P   L   A   W   A   F   R   A   A   G   H   E   V   R   V   V   A   S   P   A

1261  CTCACCGAGGACATCACCGCGGCCGGGCTGACCGCCGTCCCGGTCGGCACCGACGTCGAC  1320
       L   T   E   D   I   T   A   A   G   L   T   A   V   P   V   G   T   D   V   D

1321  CTCGTGGACTTCATGACCCACGCGGGCCACGACATCATCGACTACGTCCGGAGCCTGGAC  1380
       L   V   D   F   M   T   H   A   G   H   D   I   I   D   Y   V   R   S   L   D

1381  TTCAGCGAGCGGGACCCCGCCACCTTGACCTGGGAGCACCTGCGGGGCATGCAGACCGTG  1440
       F   S   E   R   D   P   A   T   L   T   W   E   H   L   R   G   M   Q   T   V

1441  CTCACCCCGACCTTCTACGCCCTGATGAGCCCGGACACGCTCATCGAAGGCATGGTCTCG  1500
       L   T   P   T   F   Y   A   L   M   S   P   D   T   L   I   E   G   M   V   S

1501  TTCTGCCGGAAGTGGCGGCCCGACCTGGTCATCTGGGAGCCGCTCACCTTCGCCGCGCCC  1560
       F   C   R   K   W   R   P   D   L   V   I   W   E   P   L   T   F   A   A   P

1561  ATCGCGGGCGCGGTGACCGGAACGCCGCACGCGCGGCTGCTGTGGGGACCCGACATCACC  1620
       I   A   G   A   V   T   G   T   P   H   A   R   L   L   W   G   P   D   I   T

1621  ACCCGGGCGCGGCAGAACTTCCTCGGCCTGCTGCCCGACCAGCCGGAGGAGCACCGGGAG  1680
       T   R   A   R   Q   N   F   L   G   L   L   P   D   Q   P   E   E   H   R   E

1681  GGCCCGCTCGCCGAGTGGCTCACCTGGACGCTGGAGAAGTACGGCGGCCCGGCCTTCGAC  1740
       G   P   L   A   E   W   L   T   W   T   L   E   K   Y   G   G   P   A   F   D

1741  GAGGAGGTGGTCGTCGGGCAGTGGACGATCGACCCCGCCCCGGCCGCGATCAGGCTCGAC  1800
       E   E   V   V   V   G   Q   W   T   I   D   P   A   P   A   A   I   R   L   D

1801  ACCGGCCTGAAGACCGTCGGGATGCGCTACGTCGACTACAACGGGCCGTCCGTGGTGCCG  1860
       T   G   L   K   T   V   G   M   R   Y   V   D   Y   N   G   P   S   V   V   P

1861  GAATGGCTGCACGACGAGCCCGAGCGCCGCCGCGTGTGCCTCACGCTCGGGATCTCCAGC  1920
       E   W   L   H   D   E   P   E   R   R   R   V   C   L   T   L   G   I   S   S
```

FIG. 4A-2

```
1921  CGCGAGAACAGCATCGGGCAGGTCTCCATCGAGGAGCTGCTGGGTGCCGTCGGCGACGTC  1980
       R  E  N  S  I  G  Q  V  S  I  E  E  L  L  G  A  V  G  D  V

1981  GACGCCGAGATCATCGCGACCTTCGACGCGCAGCAGCTAGAAGGCGTCGCGAACATCCCG  2040
       D  A  E  I  I  A  T  F  D  A  Q  Q  L  E  G  V  A  N  I  P

2041  CACAACGTCCGCACGGTCGGCTTCGTCCCGATGCACGCGCTGCTGCCGACCTGCGCGGCG  2100
       H  N  V  R  T  V  G  F  V  P  M  H  A  L  L  P  T  C  A  A

2101  ACGGTGCACCACGGCGGACCCGGGAGCTGGCACACCGCGGCGATCCACGGCGTGCCGCAG  2160
       T  V  H  H  G  G  P  G  S  W  H  T  A  A  I  H  G  V  P  Q

2161  GTGATCCTGCCCGACGGCTGGGACACCGGCGTGCGCGCGCAGCGCACGCAGGAATTCGGG  2220
       V  I  L  P  D  G  W  D  T  G  V  R  A  Q  R  T  Q  E  F  G

2221  GCGGGGATCGCGCTGCCCGTGCCCGAGCTGACCCCCGACCAGCTCCGGGAGTCGGTGAAG  2280
       A  G  I  A  L  P  V  P  E  L  T  P  D  Q  L  R  E  S  V  K

2281  CGGGTCCTCGACGACCCGGCCCACCGCGCCGGCGCGGCGCGGATGCGCGACGACATGCTC  2340
       R  V  L  D  D  P  A  H  R  A  G  A  A  R  M  R  D  D  M  L

2341  GCGGAGCCGTCACCGGCCGAGGTCGTCGGCATCTGCGAGGAACTGGCCGCAGGAAGGAGA  2400
       A  E  P  S  P  A  E  V  V  G  I  C  E  E  L  A  A  G  R  R

2401  GAACCACGATGACCACCGACGCCGCGACGCACGTGCGGCTCGGGCGTTCCGCGCTGCTCA  2460
       E  P  R  *
                M  T  T  D  A  A  T  H  V  R  L  G  R  S  A  L  L  T

2461  CCAGCAGGCTCTGGCTCGGCACGGTGAACTTCAGCGGACGCGTCGAGGACGACGACGCGC  2520
        S  R  L  W  L  G  T  V  N  F  S  G  R  V  E  D  D  D  A  L

2521  TGCGCCTGATGGACCACGCCCGGGACCGCGGCATCAACTGCCTCGACACCGCCGACATGT  2580
        R  L  M  D  H  A  R  D  R  G  I  N  C  L  D  T  A  D  M  Y

2581  ACGGCTGGCGGCTCTACAAGGGCCACACCGAGGAGCTGGTGGGCAGGTGGCTGGCCCAGG  2640
        G  W  R  L  Y  K  G  H  T  E  E  L  V  G  R  W  L  A  Q  G

2641  GCGGCGGACGGCGCGAGGACACCGTGCTGGCGACCAAGGTCGGCGGCGAGATGAGCGAGC  2700
        G  G  R  R  E  D  T  V  L  A  T  K  V  G  G  E  M  S  E  R

2701  GCGTCAACGACAGCGGGCTGTCGGCGCGGCACATCATCGCCTCCTGCGAGGGATCGCTGC  2760
        V  N  D  S  G  L  S  A  R  H  I  I  A  S  C  E  G  S  L  R

2761  GCAGGCTGGGCGTCGACCACATCGACGTCTACCAGATGCACCACATCGACCGGTCCGCGC  2820
        R  L  G  V  D  H  I  D  V  Y  Q  M  H  H  I  D  R  S  A  P

2821  CGTGGGACGAGGTGTGGCAGGCCATGGACAGCCTCGTCGCCAGCGGCAAGGTCTCCTACG  2880
        W  D  E  V  W  Q  A  M  D  S  L  V  A  S  G  K  V  S  Y  V
```

FIG. 4A-3

```
2881  TCGGCTCGTCGAACTTCGCGGGCTGGCACATCGCCGCCGCGCAGGAGAACGCCGCCCGCC  2940
       G  S  S  N  F  A  G  W  H  I  A  A  A  Q  E  N  A  A  R  R

2941  GCCACTCCCTGGGCATGGTCTCCCACCAGTGCCTGTACAACCTGGCGGTCCGGCACGCCG  3000
       H  S  L  G  M  V  S  H  Q  C  L  Y  N  L  A  V  R  H  A  E

3001  AGCTGGAGGTGCTGCCCGCCGCGCAGGCCTACGGGCTCGGCGTCTTCGCCTGGTCGCCGC  3060
       L  E  V  L  P  A  A  Q  A  Y  G  L  G  V  F  A  W  S  P  L

3061  TGCACGGCGGCCTGCTCAGCGGAGCGCTGGAGAAGCTGGCCGCGGGCACCGCGGTGAAGT  3120
       H  G  G  L  L  S  G  A  L  E  K  L  A  A  G  T  A  V  K  S

3121  CGGCGCAGGGCCGTGCGCAGGTGCTGTTGCCGTCCCTGCGCCCGGCGATCGAGGCCTACG  3180
       A  Q  G  R  A  Q  V  L  L  P  S  L  R  P  A  I  E  A  Y  E

3181  AGAAGTTCTGCCGCAACCTCGGCGAAGACCCGGCCGAGGTGGGGCTCGCATGGGTGCTGT  3240
       K  F  C  R  N  L  G  E  D  P  A  E  V  G  L  A  W  V  L  S

3241  CCCGGCCCGGCATCGCCGGCGCCGTCATCGGCCCGCGAACCCCCGAGCAGCTCGACTCCG  3300
       R  P  G  I  A  G  A  V  I  G  P  R  T  P  E  Q  L  D  S  A

3301  CGCTGAAGGCGTCCGCGATGACCCTGGACGAGCAGGCGCTGTCCGAACTGGACGAGATCT  3360
       L  K  A  S  A  M  T  L  D  E  Q  A  L  S  E  L  D  E  I  F

3361  TCCCCGCGGTGGCCTCCGGCGGCGCGGCGCCGGAAGCCTGGTTGCAGTGAGCACAAGAGG  3420
       P  A  V  A  S  G  G  A  A  P  E  A  W  L  Q  *

3421  AACCGAGAAAGGATACGGCTGGTGAGCGTGAAGCAGAAGTCAGCGTTGCAGGACCTGGTC  3480

3481  GACTTCGCCAAGTGGCACGTGTGGACCAGGGTGCGGCCGTCCAGCCGTGCGCGCCTGGCC  3540

3541  TACGAGCTGTTCGCCGACGACCACGAGGCCACGACCGAGGGCGCCTACATCAACCTCGGC  3600

3601  TACTGGAAGCCCGGGTGCGCCGGCCTGGAGGAGGCCAACCAGGAGCTGGCGAACCAGCTC  3660

3661  GCCGAGGCCGCGGGGATCAGCGAGGGCGACGAGGTGCTCGACGTCGGGTTCGGGCTCGGC  3720

3721  GCGCAGGACTTCTTCTGGCTCGACCTGCAGCCAGCT  3756
```

FIG. 4A-4

```
  1 CGGGTTGCCGCACATCGCGCTGGGGAGATTCTTTGAATTTCGCCCGTAGCACCGACCTGG   60

61 AAAGCGAGCAAATGCTCCGGTGAATGGGATCAGTGATTCCCCGCGTCAATTGATCACCCT  120
                      V  N  G  I  S  D  S  P  R  Q  L  I  T  L

121 TCTGGGCGCTTCCGGCTTCGTCGGGAGCGCGGTTCTGCGCGAGCTGCGCGACCACCCGGT  180
     L  G  A  S  G  F  V  G  S  A  V  L  R  E  L  R  D  H  P  V

181 CCGGCTGCGCGCGGTGTCCCGCGGCGGAGCGCCCGCGGTTCCGCCCGGCGCCGCGGAGGT  240
     R  L  R  A  V  S  R  G  G  A  P  A  V  P  P  G  A  A  E  V

241 CGAGGACCTGCGCGCCGACCTGCTGGAACCGGGCCGGGCCGCCGCCGCGATCGAGGACGC  300
     E  D  L  R  A  D  L  L  E  P  G  R  A  A  A  A  I  E  D  A

301 CGACGTGATCGTGCACCTGGTGGCGCACGCAGCGGGCGGTTCCACCTGGCGCAGCGCCAC  360
     D  V  I  V  H  L  V  A  H  A  A  G  G  S  T  W  R  S  A  T

361 CTCCGACCCGGAAGCCGAGCGGGTCAACGTCGGCCTGATGCACGACCTCGTCGGCGCGCT  420
     S  D  P  E  A  E  R  V  N  V  G  L  M  H  D  L  V  G  A  L

421 GCACGATCGCCGCAGGTCGACGCCGCCCGTGTTGCTCTACGCGAGCACCGCACAGGCCGC  480
     H  D  R  R  R  S  T  P  P  V  L  L  Y  A  S  T  A  Q  A  A

481 GAACCCGTCGGCGGCCAGCAGGTACGCGCAGCAGAAGACCGAGGCCGAGCGCATCCTGCG  540
     N  P  S  A  A  S  R  Y  A  Q  Q  K  T  E  A  E  R  I  L  R

541 CAAAGCCACCGACGAGGGCCGGGTGCGCGGCGTGATCCTGCGGCTGCCCGCGGTCTACGG  600
     K  A  T  D  E  G  R  V  R  G  V  I  L  R  L  P  A  V  Y  G

601 CCAGAGCGGCCCGTCCGGCCCCATGGGGCGGGGCGTGGTCGCAGCGATGATCCGGCGTGC  660
     Q  S  G  P  S  G  P  M  G  R  G  V  V  A  A  M  I  R  R  A

661 CCTCGCCGGCGAGCCGCTCACCATGTGGCACGACGGCGGCGTGCGCCGCGACCTGCTGCA  720
     L  A  G  E  P  L  T  M  W  H  D  G  G  V  R  R  D  L  L  H

721 CGTCGAGGACGTGGCCACCGCGTTCGCCGCCGCGCTGGAGCACCACGACGCGCTGGCCGG  780
     V  E  D  V  A  T  A  F  A  A  A  L  E  H  H  D  A  L  A  G

781 CGGCACGTGGGCGCTGGGCGCCGACCGATCCGAGCCGCTCGGCGACATCTTCCGGGCCGT  840
     G  T  W  A  L  G  A  D  R  S  E  P  L  G  D  I  F  R  A  V

841 CTCCGGCAGCGTCGCCCGGCAGACCGGCAGCCCCGCCGTCGACGTGGTCACCGTGCCCGC  900
     S  G  S  V  A  R  Q  T  G  S  P  A  V  D  V  V  T  V  P  A

901 GCCCGAGCACGCCGAGGCCAACGACTTCCGCAGCGACGACATCGACTCCACCGAGTTCCG  960
     P  E  H  A  E  A  N  D  F  R  S  D  D  I  D  S  T  E  F  R
```

FIG. 4B-1

```
 961  CAGCCGGACCGGCTGGCGCCCCGGGTTTCCCTCACCGACGGCATCGACCGGACGGTGGC  1020
        S  R  T  G  W  R  P  R  V  S  L  T  D  G  I  D  R  T  V  A

1021  CGCCCTGACCCCCACCGAGGAGCACTAGTGCGGGTACTGCTGACGTCCTTCGCGCACCGC  1080
        A  L  T  P  T  E  E  H  *
                                  V  R  V  L  L  T  S  F  A  H  R

1081  ACGCACTTCCAGGGACTGGTCCCGCTGGCGTGGGCGCTGCGCACCGCGGGTCACGACGTG  1140
        T  H  F  Q  G  L  V  P  L  A  W  A  L  R  T  A  G  H  D  V

1141  CGCGTGGCCGCCCAGCCCGCGCTCACCGACGCGGTCATCGGCGCCGGTCTCACCGCGGTA  1200
        R  V  A  A  Q  P  A  L  T  D  A  V  I  G  A  G  L  T  A  V

1201  CCCGTCGGCTCCGACCACCGGCTGTTCGACATCGTCCCGGAAGTCGCCGCTCAGGTGCAC  1260
        P  V  G  S  D  H  R  L  F  D  I  V  P  E  V  A  A  Q  V  H

1261  CGCTACTCCTTCTACCTGGACTTCTACCACCGCGAGCAGGAGCTGCACTCGTGGGAGTTC  1320
        R  Y  S  F  Y  L  D  F  Y  H  R  E  Q  E  L  H  S  W  E  F

1321  CTGCTCGGCATGCAGGAGGCCACCTCGCGGTGGGTATACCCGGTGGTCAACAACGACTCC  1380
        L  L  G  M  Q  E  A  T  S  R  W  V  Y  P  V  V  N  N  D  S

1381  TTCGTCGCCGAGCTGGTCGACTTCGCCCGGGACTGGCGTCCTGACCTGGTGCTCTGGGAG  1440
        F  V  A  E  L  V  D  F  A  R  D  W  R  P  D  L  V  L  W  E

1441  CCGTTCACCTTCGCCGGCGCCGTCGCGGCCCGGGCCTGCGGAGCCGCGCACGCCCGGCTG  1500
        P  F  T  F  A  G  A  V  A  A  R  A  C  G  A  A  H  A  R  L

1501  CTGTGGGGCAGCGACCTCACCGGCTACTTCCGCGGCCGGTTCCAGGCGCAACGCCTGCGA  1560
        L  W  G  S  D  L  T  G  Y  F  R  G  R  F  Q  A  Q  R  L  R

1561  CGGCCGCCGGAGGACCGGCCGGACCCGCTGGGCACGTGGCTGACCGAGGTCGCGGGGCGC  1620
        R  P  P  E  D  R  P  D  P  L  G  T  W  L  T  E  V  A  G  R

1621  TTCGGCGTCGAATTCGGCGAGGACCTCGCGGTCGGGCAGTGGTCGGTCGACCAGTTGCCG  1680
        F  G  V  E  F  G  E  D  L  A  V  G  Q  W  S  V  D  Q  L  P

1681  CCGAGTTTCCGGCTGGACACCGGAATGGAAACCGTTGTCGCGCGGACCCTGCCCTACAAC  1740
        P  S  F  R  L  D  T  G  M  E  T  V  V  A  R  T  L  P  Y  N

1741  GGCGCGTCGGTGGTTCCGGACTGGCTCAAGAAGGGCAGTGCGACTCGACGCATCTGCATT  1800
        G  A  S  V  V  P  D  W  L  K  K  G  S  A  T  R  R  I  C  I

1801  ACCGGAGGGTTCTCCGGACTCGGGCTCGCCGCCGATGCCGATCAGTTCGCGCGGACGCTC  1860
        T  G  G  F  S  G  L  G  L  A  A  D  A  D  Q  F  A  R  T  L
```

FIG. 4B-2

```
1861  GCGCAGCTCGCGCGATTCGATGGCGAAATCGTGGTTACGGGTTCCGGTCCGGATACCTCC  1920
       A  Q  L  A  R  F  D  G  E  I  V  V  T  G  S  G  P  D  T  S

1921  GCGGTACCGGACAACATTCGTTTGGTGGATTTCGTTCCGATGGGCGTTCTGCTCCAGAAC  1980
       A  V  P  D  N  I  R  L  V  D  F  V  P  M  G  V  L  L  Q  N

1981  TGCGCGGCGATCATCCACCACGGCGGGGCCGGAACCTGGGCCACGGCACTGCACCACGGA  2040
       C  A  A  I  I  H  H  G  G  A  G  T  W  A  T  A  L  H  H  G

2041  ATTCCGCAAATATCAGTTGCACATGAATGGGATTGCATGCTACGCGGCCAGCAGACCGCG  2100
       I  P  Q  I  S  V  A  H  E  W  D  C  M  L  R  G  Q  Q  T  A

2101  GAACTGGGCGCGGGAATCTACCTCCGGCCGGACGAGGTCGATGCCGACTCATTGGCGAGC  2160
       E  L  G  A  G  I  Y  L  R  P  D  E  V  D  A  D  S  L  A  S

2161  GCCCTCACCCAGGTGGTCGAGGACCCCACCTACACCGAGAACGCGGTGAAGCTTCGCGAG  2220
       A  L  T  Q  V  V  E  D  P  T  Y  T  E  N  A  V  K  L  R  E

2221  GAGGCGCTGTCCGACCCGACGCCGCAGGAGATCGTCCCGCGACTGGAGGAACTCACGCGC  2280
       E  A  L  S  D  P  T  P  Q  E  I  V  P  R  L  E  E  L  T  R

2281  CGCCACGCCGGCTAGCGGTTTCCGACCGACAAGTCCGTCCGACAGCACACCTCCGGAGGG  2340
       R  H  A  G  *

2341  AGCAGGGATGTACGAGGGCGGGTTCGCCGAGCTTTACGACCGGTTCTACCGCGGCCGGGG  2400
              M  Y  E  G  G  F  A  E  L  Y  D  R  F  Y  R  G  R  G

2401  CAAGGACTACGCGGCCGAGGCCGCGCAGGTCGCGCGGCTGGTCAGAGACCGCCTGCCCTC  2460
       K  D  Y  A  A  E  A  A  Q  V  A  R  L  V  R  D  R  L  P  S

2461  GGCTTCCTCGCTGCTCGACGTGGCCTGCGGGACCGGCACCCACCTGCGCCGGTTCGCCGA  2520
       A  S  S  L  L  D  V  A  C  G  T  G  T  H  L  R  R  F  A  D

2521  CCTCTTCGACGACGTGACCGGGCTGGAGCTGTCGGCGGCGATGATCGAGGTCGCCCGGCC  2580
       L  F  D  D  V  T  G  L  E  L  S  A  A  M  I  E  V  A  R  P

2581  GCAGCTCGGCGGCATCCCGGTGCTGCAGGGCGACATGCGCGACTTCGCGCTGGATCGCGA  2640
       Q  L  G  G  I  P  V  L  Q  G  D  M  R  D  F  A  L  D  R  E

2641  GTTCGACGCCGTCACCTGCATGTTCAGCTCCATCGGGCACATGCGCGACGGCGCCGAGCT  2700
       F  D  A  V  T  C  M  F  S  S  I  G  H  M  R  D  G  A  E  L

2701  GGACCAGGCGCTGGCGTCCTTCGCCCGCCACCTCGCCCCCGGCGGCGTCGTGGTGGTCGA  2760
       D  Q  A  L  A  S  F  A  R  H  L  A  P  G  G  V  V  V  V  E

2761  ACCGTGGTGGTTCCCGGAGGACTTCCTCGACGGCTACGTGGCCGGTGACGTGGTGCGCGA  2820
       P  W  W  F  P  E  D  F  L  D  G  Y  V  A  G  D  V  V  R  D
```

FIG. 4B-3

```
2821  CGGCGACCTGACGATCTCGCGCGTCTCGCACTCCGTGCGCGCCGGCGGCGCGACCCGGAT  2880
        G   D   L   T   I   S   R   V   S   H   S   V   R   A   G   G   A   T   R   M

2881  GGAGATCCACTGGGTCGTGGCCGACGCGGTGAACGGTCCGCGGCACCACGTGGAGCACTA  2940
        E   I   H   W   V   V   A   D   A   V   N   G   P   R   H   H   V   E   H   Y

2941  CGAGATCACGCTCTTCGAGCGGCAGCAGTACGAGAAGGCCTTCACCGCGGCCGGTTGCGC  3000
        E   I   T   L   F   E   R   Q   Q   Y   E   K   A   F   T   A   A   G   C   A

3001  TGTGCAGTACCTGGAGGGCGGACCCTCCGGACGCGGGTTGTTCGTCGGTGTGCGCGGATG  3060
        V   Q   Y   L   E   G   G   P   S   G   R   G   L   F   V   G   V   R   *

3061  ACCCGTGCGTCGCGTTTTCCGTTCCTGGCACAGGTGATCCGCTCCACGGGCCCTTTCCCC  3120

3121  GCCGTGACCGGACCCTTACAGTGAGTGCGGGTCTTGATCGACAACGCCCGGCGGCAGCAA  3180

3181  GCGGAGCCGTCGACGACACCGCAGGGAGAGTCGATGGGTGATCGGACCGGCGACCGGACG  3240
                                            M   G   D   R   T   G   D   R   T

3241  ATTCCGGAATCCTCGCAGACCGCAACGCGTTTCCTGCTCGGCGACGGCGGAATCCCCACC  3300
        I   P   E   S   S   Q   T   A   T   R   F   L   L   G   D   G   G   I   P   T

3301  GCCACGGCGGAAACCCACGACTGGCTGACCCGCAACGGCGCCGAGCAGCGGCTCGAGGTG  3360
        A   T   A   E   T   H   D   W   L   T   R   N   G   A   E   Q   R   L   E   V

3361  GCGCGCGTGCCGTTCAGCGCCATGGACCGCTGGTCGTTCCAGCCCGAGGACGGCAGGCTC  3420
        A   R   V   P   F   S   A   M   D   R   W   S   F   Q   P   E   D   G   R   L

3421  GCCCACGAGTCCGGGCGCTTCTTCTCCATCGAGGGCCTGCACGTGCGGACGAACTTCGGC  3480
        A   H   E   S   G   R   F   F   S   I   E   G   L   H   V   R   T   N   F   G

3481  TGGCGGCGGGACTGGATCCAGCCCATCATCGTGCAGCCCGAGATCGGCTTCCTCGGCCTC  3540
        W   R   R   D   W   I   Q   P   I   I   V   Q   P   E   I   G   F   L   G   L

3541  ATCGTCAAGGAGTTCGACGGTGTGCTGCACGTGCTGGCGCAGGCCAAGGCCGAGCCGGGC  3600
        I   V   K   E   F   D   G   V   L   H   V   L   A   Q   A   K   A   E   P   G

3601  AACATCAACGCCGTCCAGCTCTCCCCGACCCTGCAGGCGACCCGCAGCAACTACACCGGC  3660
        N   I   N   A   V   Q   L   S   P   T   L   Q   A   T   R   S   N   Y   T   G

3661  GTCCACCGCGGCTCGAAGGTCCGGTTCATCGAGTACTTCAACGGCACGCGCCCGAGCCGG  3720
        V   H   R   G   S   K   V   R   F   I   E   Y   F   N   G   T   R   P   S   R

3721  ATCCTCGTCGACGTGCTCCAGTCCGAGCAGGGCGCGTGGTTCCTGCGCAAGCGCAACCGG  3780
        I   L   V   D   V   L   Q   S   E   Q   G   A   W   F   L   R   K   R   N   R
```

FIG. 4B-4

```
3781  AACATGGTCGTCGAGGTGTTCGACGACCTGCCCGAGCACCCGAACTTCCGGTGGCTGACC  3840
       N  M  V  V  E  V  F  D  D  L  P  E  H  P  N  F  R  W  L  T

3841  GTCGCGCAGCTGCGGGCGATGCTGCACCACGACAACGTGGTGAACATGGACCTGCGCACC  3900
       V  A  Q  L  R  A  M  L  H  H  D  N  V  V  N  M  D  L  R  T

3901  GTGCTGGCCTGCGTCCCGACCGCCGTGGAGCGGGACCGGGCCGACGACGTGCTCGCGCGC  3960
       V  L  A  C  V  P  T  A  V  E  R  D  R  A  D  D  V  L  A  R

3961  CTGCCCGAGGGCTCGTTCCAGGCCCGGCTGCTGCACTCGTTCATCGGCGCGGGCACCCCG  4020
       L  P  E  G  S  F  Q  A  R  L  L  H  S  F  I  G  A  G  T  P

4021  GCCAACAACATGAACAGCCTGCTGAGCTGGATCTCCGACGTGCGCGCCAGGCGCGAGTTC  4080
       A  N  N  M  N  S  L  L  S  W  I  S  D  V  R  A  R  R  E  F

4081  GTGCAGCGCGGCCGCCCGCTGCCCGACATCGAGCGCAGCGGGTGGATCCGCCGCGACGAC  4140
       V  Q  R  G  R  P  L  P  D  I  E  R  S  G  W  I  R  R  D  D

4141  GGCATCGAGCACGAGGAGAAGAAGTACTTCGACGTCTTCGGCGTCACGGTGGCGACCAGC  4200
       G  I  E  H  E  E  K  K  Y  F  D  V  F  G  V  T  V  A  T  S

4201  GACCGCGAGGTCAACTCGTGGATGCAGCCGCTGCTCTCGCCCGCCAACAACGGCCTGCTC  4260
       D  R  E  V  N  S  W  M  Q  P  L  L  S  P  A  N  N  G  L  L

4261  GCCCTGCTGGTCAAGGACATCGGCGGCACGTTGCACGCGCTCGTGCAGCTGCGCACCGAG  4320
       A  L  L  V  K  D  I  G  G  T  L  H  A  L  V  Q  L  R  T  E

4321  GCGGGCGGGATGGACGTCGCCGAGCTGGCGCCTACGGTGCACTGCCAGCCCGACAACTAC  4380
       A  G  G  M  D  V  A  E  L  A  P  T  V  H  C  Q  P  D  N  Y

4381  GCCGACGCGCCCGAGGAGTTCCGACCGGCCTATGTGGACTACGTGTTGAACGTGCCGCGC  4440
       A  D  A  P  E  E  F  R  P  A  Y  V  D  Y  V  L  N  V  P  R

4441  TCGCAGGTCCGCTACGACGCATGGCACTCCGAGGAGGGCGGCCGGTTCTACCGCAACGAG  4500
       S  Q  V  R  Y  D  A  W  H  S  E  E  G  G  R  F  Y  R  N  E

4501  AACCGGTACATGCTGATCGAGGTGCCCGCCGACTTCGACGCCAGTGCCGCTCCCGACCAC  4560
       N  R  Y  M  L  I  E  V  P  A  D  F  D  A  S  A  A  P  D  H

4561  CGGTGGATGACCTTCGACCAGATCACCTACCTGCTCGGGCACAGCCACTACGTCAACATC  4620
       R  W  M  T  F  D  Q  I  T  Y  L  L  G  H  S  H  Y  V  N  I

4621  CACGTGCGCAGCATCATCGCGTGCGCCTCGGCCGTCTACACCAGGACCGCCGGATGAAAC  4680
       H  V  R  S  I  I  A  C  A  S  A  V  Y  T  R  T  A  G  *
                                                              M  K  R

4681  GCGCGCTGACCGACCTGGCGATCTTCGGCGGCCCCGAGGCATTCCTGCACACCCTCTACG  4740
        A  L  T  D  L  A  I  F  G  G  P  E  A  F  L  H  T  L  Y  V
```

FIG. 4B-5

```
4741  TGGGCAGGCCGACCGTCGGGGACCGGGAGCGGTTCTTCGCCCGCCTGGAGTGGGCGCTGA  4800
       G  R  P  T  V  G  D  R  E  R  F  F  A  R  L  E  W  A  L  N

4801  ACAACAACTGGCTGACCAACGGCGGACCACTGGTGCGCGAGTTCGAGGGCCGGGTCGCCG  4860
       N  N  W  L  T  N  G  G  P  L  V  R  E  F  E  G  R  V  A  D

4861  ACCTGGCGGGTGTCCGCCACTGCGTGGCCACCTGCAACGCGACGGTCGCGCTGCAACTGG  4920
       L  A  G  V  R  H  C  V  A  T  C  N  A  T  V  A  L  Q  L  V

4921  TGCTGCGCGCGAGCGACGTGTCCGGCGAGGTCGTCATGCCTTCGATGACGTTCGCGGCCA  4980
       L  R  A  S  D  V  S  G  E  V  V  M  P  S  M  T  F  A  A  T

4981  CCGCGCACGCGGCGAGCTGGCTGGGGCTGGAACCGGTGTTCTGCGACGTGGACCCCGAGA  5040
       A  H  A  A  S  W  L  G  L  E  P  V  F  C  D  V  D  P  E  T

5041  CCGGCCTGCTCGACCCCGAGCACGTCGCGTCGCTGGTCACACCGCGGACGGGCGCGATCA  5100
       G  L  L  D  P  E  H  V  A  S  L  V  T  P  R  T  G  A  I  I

5101  TCGGCGTGCACCTCTGGGGCAGGCCCGCTCCGGTCGAGGCGCTGGAGAAGATCGCCGCCG  5160
       G  V  H  L  W  G  R  P  A  P  V  E  A  L  E  K  I  A  A  E

5161  AGCACCAGGTCAAACTCTTCTTCGACGCCGCGCACGCGCTGGGCTGCACCGCCGGCGGGC  5220
       H  Q  V  K  L  F  F  D  A  A  H  A  L  G  C  T  A  G  G  R

5221  GGCCGGTCGGCGCCTTCGGCAACGCCGAGGTGTTCAGCTTCCACGCCACGAAGGCGGTCA  5280
       P  V  G  A  F  G  N  A  E  V  F  S  F  H  A  T  K  A  V  T

5281  CCTCGTTCGAGGGCGGCGCCATCGTCACCGACGACGGGCTGCTGGCCGACCGCATCCGCG  5340
       S  F  E  G  G  A  I  V  T  D  D  G  L  L  A  D  R  I  R  A

5341  CCATGCACAACTTCGGGATCGCACCGGACAAGCTGGTGACCGATGTCGGCACCAACGGCA  5400
       M  H  N  F  G  I  A  P  D  K  L  V  T  D  V  G  T  N  G  K

5401  AGATGAGCGAGTGCGCCGCGGCGATGGGCCTCACCTCGCTCGACGCCTTCGCCGAGACCA  5460
       M  S  E  C  A  A  A  M  G  L  T  S  L  D  A  F  A  E  T  R

5461  GGGTGCACAACCGCCTCAACCACGCGCTCTACTCCGACGAGCTCCGCGACGTGCGCGGCA  5520
       V  H  N  R  L  N  H  A  L  Y  S  D  E  L  R  D  V  R  G  I

5521  TATCCGTGCACGCGTTCGATCCTGGCGAGCAGAACAACTACCAGTACGTGATCATCTCGG  5580
       S  V  H  A  F  D  P  G  E  Q  N  N  Y  Q  Y  V  I  I  S  V

5581  TGGACTCCGCGGCCACCGGCATCGACCGCGACCAGTTGCAGGCGATCCTGCGAGCGGAGA  5640
       D  S  A  A  T  G  I  D  R  D  Q  L  Q  A  I  L  R  A  E  K

5641  AGGTTGTGGCACAACCCTACTTCTCCCCCGGGTGCCACCAGATGCAGCCGTACCGGACCG  5700
       V  V  A  Q  P  Y  F  S  P  G  C  H  Q  M  Q  P  Y  R  T  E
```

FIG. 4B-6

```
5701  AGCCGCCGCTGCGGCTGGAGAACACCGAACAGCTCTCCGACCGGGTGCTCGCGCTGCCCA   5760
       P  P  L  R  L  E  N  T  E  Q  L  S  D  R  V  L  A  L  P  T

5761  CCGGCCCCGCGGTGTCCAGCGAGGACATCCGGCGGGTGTGCGACATCATCCGGCTCGCCG   5820
       G  P  A  V  S  S  E  D  I  R  R  V  C  D  I  I  R  L  A  A

5821  CCACCAGCGGCGAGCTGATCAACGCGCAATGGGACCAGAGGACGCGCAACGGTTCGTGAC   5880
       T  S  G  E  L  I  N  A  Q  W  D  Q  R  T  R  N  G  S  *

5881  GACCTGCGCCACAAGTGCCAGGAGGTTCGCTCCCCGATGAACACAACTCGTACGGCAACC   5940
                                              M  N  T  T  R  T  A  T

5941  GCCCAGGAAGCGGGGGTCGCCGACGCGGCGCGCCCGGACGTCGACCGGCGGGCGGTCGTG   6000
       A  Q  E  A  G  V  A  D  A  A  R  P  D  V  D  R  R  A  V  V

6001  CGGGCGCTGAGCTCGGAGGTCTCCCGCGTCACCGGCGCCGGTGACGGTGACGCCCACGTG   6060
       R  A  L  S  S  E  V  S  R  V  T  G  A  G  D  G  D  A  H  V

6061  CAGGCCGCCCGGCTCGCCGACCTCGCCGCGCACTACGGGGCGCACCCGTTCACGCCGCTG   6120
       Q  A  A  R  L  A  D  L  A  A  H  Y  G  A  H  P  F  T  P  L

6121  GAGCAGACGCGTGCGCGGCTCGGCCTGGACCGCGCGGAGTTCGCCCACCTGCTCGACCTG   6180
       E  Q  T  R  A  R  L  G  L  D  R  A  E  F  A  H  L  L  D  L

6181  TTCGGCCGCATCCCGGACCTGGGCACCGCGGTGGAGCACGGTCCGGCGGGCAAGTACTGG   6240
       F  G  R  I  P  D  L  G  T  A  V  E  H  G  P  A  G  K  Y  W

6241  TCCAACACGATCAAGCCGCTGGACGCCGCAGGCGCACTGGACGCGGCGGTCTACCGCAAG   6300
       S  N  T  I  K  P  L  D  A  A  G  A  L  D  A  A  V  Y  R  K

6301  CCTGCCTTCCCCTACAGCGTCGGCCTGTACCCCGGGCCGACGTGCATGTTCCGCTGCCAC   6360
       P  A  F  P  Y  S  V  G  L  Y  P  G  P  T  C  M  F  R  C  H

6361  TTCTGCGTGCGGGTGACCGGTGCCCGCTACGAGGCCGCATCGGTCCCGGCGGGCAACGAG   6420
       F  C  V  R  V  T  G  A  R  Y  E  A  A  S  V  P  A  G  N  E

6421  ACGCTGGCCGCGATCATCGACGAGGTGCCCACGGACAACCCGAAGGCGATGTACATGTCG   6480
       T  L  A  A  I  I  D  E  V  P  T  D  N  P  K  A  M  Y  M  S

6481  GGCGGGCTCGAGCCGCTGACCAACCCCGGTCTCGGCGAGCTGGTGTCGCACGCCGCCGGG   6540
       G  G  L  E  P  L  T  N  P  G  L  G  E  L  V  S  H  A  A  G

6541  CGCGGTTTCGACCTCACCGTCTACACCAACGCCTTCGCCCTCACCGAGCAGACGCTGAAC   6600
       R  G  F  D  L  T  V  Y  T  N  A  F  A  L  T  E  Q  T  L  N

6601  CGCCAGCCCGGCCTGTGGGAGCTGGGCGCGATCCGCACGTCCCTCTACGGGCTGAACAAC   6660
       R  Q  P  G  L  W  E  L  G  A  I  R  T  S  L  Y  G  L  N  N
```

FIG. 4B-7

```
6661  GACGAGTACGAGACGACCACCGGCAAGCGCGGCGCTTTCGAACGCGTCAAGAAGAACCTG  6720
       D  E  Y  E  T  T  T  G  K  R  G  A  F  E  R  V  K  K  N  L

6721  CAGGGCTTCCTGCGGATGCGCGCCGAGCGGGACGCGCCGATCCGGCTCGGCTTCAACCAC  6780
       Q  G  F  L  R  M  R  A  E  R  D  A  P  I  R  L  G  F  N  H

6781  ATCATCCTGCCGGGACGGGCCGACCGGCTCACCGACCTCGTCGACTTCATCGCCGAGCTC  6840
       I  I  L  P  G  R  A  D  R  L  T  D  L  V  D  F  I  A  E  L

6841  AACGAGTCCAGCCCGCAACGGCCGCTGGACTTCGTGACGGTGCGCGAGGACTACAGCGGC  6900
       N  E  S  S  P  Q  R  P  L  D  F  V  T  V  R  E  D  Y  S  G

6901  CGCGACGACGGCCGGCTGTCGGACTCCGAGCGCAACGAGCTGCGCGAGGGCCTGGTGCGG  6960
       R  D  D  G  R  L  S  D  S  E  R  N  E  L  R  E  G  L  V  R

6961  TTCGTCGACTACGCCGCCGAGCGGACCCCGGGCATGCACATCGACCTGGGCTACGCCCTG  7020
       F  V  D  Y  A  A  E  R  T  P  G  M  H  I  D  L  G  Y  A  L

7021  GAGAGCCTGCGGCGGGGTGTGGACGCCGAGCTGCTGCGCATCCGGCCGGAGACGATGCGT  7080
       E  S  L  R  R  G  V  D  A  E  L  L  R  I  R  P  E  T  M  R

7081  CCCACCGCGCACCCCCAGGTCGCGGTGCAGATCGACCTGCTCGGCGACGTCTACCTCTAC  7140
       P  T  A  H  P  Q  V  A  V  Q  I  D  L  L  G  D  V  Y  L  Y

7141  CGCGAGGCGGGCTTCCCGGAGCTGGAGGGCGCCACCCGCTACATCGCGGGCCGGGTCACC  7200
       R  E  A  G  F  P  E  L  E  G  A  T  R  Y  I  A  G  R  V  T

7201  CCGTCGACCAGCCTGCGCGAGGTGGTGGAGAACTTCGTGCTGGAGAACGAGGGCGTGCAG  7260
       P  S  T  S  L  R  E  V  V  E  N  F  V  L  E  N  E  G  V  Q

7261  CCCCGCCCCGGCGACGAGTACTTCCTCGACGGCTTCGACCAGTCGGTGACCGCACGGCTC  7320
       P  R  P  G  D  E  Y  F  L  D  G  F  D  Q  S  V  T  A  R  L

7321  AACCAGCTCGAACGAGACATCGCCGACGGGTGGGAGGACCACCGCGGCTTCCTGCGCGGA  7380
       N  Q  L  E  R  D  I  A  D  G  W  E  D  H  R  G  F  L  R  G

7381  AGGTGAACCGGAGTTGCGAGTACGTGAGCTGGCGGTGGCGGGCGGTTTCGAGTTCACCCC  7440
       R  *                             V  A  G  G  F  E  F  T  P

7441  CGACCCGAAGCAGGACCGGCGGGGCCTGTTCGTGTCTCCGCTGCAGGACGAGGCGTTCGT  7500
       D  P  K  Q  D  R  R  G  L  F  V  S  P  L  Q  D  E  A  F  V

7501  GGGCGCGGTGGGCCATCGGTTCCCCGTCGCCCAGATGAACCACATCGTCTCCGCCCGGGG  7560
       G  A  V  G  H  R  F  P  V  A  Q  M  N  H  I  V  S  A  R  G

7561  CGTGCTGCGCGGGCTGCACTTCACCACCACCCCGCCGGGGCAGTGCAAGTACGTCTACTG  7620
       V  L  R  G  L  H  F  T  T  T  P  P  G  Q  C  K  Y  V  Y  C
```

FIG. 4B-8

```
7621  CGCGCGCGGCCGGGCGCTCGACGTCATCGTCGACATCCGGGTCGGCTCGCCGACGTTCGG  7680
       A  R  G  R  A  L  D  V  I  V  D  I  R  V  G  S  P  T  F  G

7681  GAAGTGGGACGCGGTGGAGATGGACACCGAGCACTTCCGGGCGGTCTACTTCCCCAGGGG  7740
       K  W  D  A  V  E  M  D  T  E  H  F  R  A  V  Y  F  P  R  G

7741  CACCGCGCACGCCTTCCTCGCGCTTGAGGACGACACCCTGATGTCGTACCTGGTCAGCAC  7800
       T  A  H  A  F  L  A  L  E  D  D  T  L  M  S  Y  L  V  S  T

7801  GCCGTACGTGGCCGAGTACGAGCAGGCGATCGACCCGTTCGACCCCGCGCTGGGTCTGCC  7860
       P  Y  V  A  E  Y  E  Q  A  I  D  P  F  D  P  A  L  G  L  P

7861  GTGGCCCGCGGACCTGGAGGTCGTGCTCTCCGACCGCGACACGGTGGCCGTGGACCTGGA  7920
       W  P  A  D  L  E  V  V  L  S  D  R  D  T  V  A  V  D  L  E

7921  GACCGCCAGGCGGCGAGGGATGCTGCCCGACTACGCCGACTGCCTCGGCGAGGAGCCCGC  7980
       T  A  R  R  R  G  M  L  P  D  Y  A  D  C  L  G  E  E  P  A

7981  CAGCACCGGCAGGTGACGGGTCCCGAGCACGATCTGTTCGAAGTGGCGCAGGCGCTCGTC  8040
       S  T  G  R  *

8041  GTCGCGGTCGA  8051
```

FIG. 4B-9

```
            1                                                    50
eryBIV      vngisdsprq litllGaSGf vGsavlreLr dhpv.rlrav sRggapavpp
ascF        ......mk.. .llitGvSGy iGshlvnyLa nlggyeiygi sRneildqdi
rfbJ        ....mtflke yvivsGaSGf iGkhlleaLk k.sgisvvai tRdvi..knn
strL        ...mspyprp rwlvtGaSGm lGreltplld rrga.avtal gRghl.ditd
Consensus   ---------- ------G-SG- ---------- -G-------- -R--------

51                                                  100
eryBIV      gaaevedlra dllepgraaa aiedadvivh lvahaAggst wrsatsdpe.
ascF        nql.lliniki fqldrdslpd ilkrvrpdv. .vihlAscfl sqhsyknike
rfbJ        sna.lanvrw cswdnielIv eelsidsali giihlAtey. .ghktsslin
strL        gaa....... ......vrsav aehrpavvvn caawtAvd.. ..eaesepal
Consensus   ---------- ---------- ---------- ----A----- ----------

101                                                 150
eryBIV      aervNvglmh dLvgalhdrr rstppvllya staqaanpsa asryaqqkte
ascF        iiksNvefpt eLlea..... ......mndv gvkkiintgt swqcfnsdty
rfbJ        iedaNvikpl kLldl..... ......aiky radiflntd. sffakkdfny
strL        amavNgegpr hLaqa..... ..c ravgavlql stdyvfpgsg grpyredhpt
Consensus   ----N----- -L-------- ---------- ---------- ----------
```

FIG. 5A-1

```
           151                                                            200
eryBIV     aerilrkatd egrvrgvilr lpa........ ..vygqsGps gpmgrgvvaa
ascF       npvnlyaask qafedilkfy inaegfsain  lklfdtyGgv dkrrklis.l
rfbJ       qhmrpyiitk rhfdeighyy anmhdisfvn  mrlehvyGpg dgenkfipyi
strL       gprtvygctk rageravlev lpdtgyivrt  awlygagGp. .....nfvak
Consensus  ---------- ---------- ---------- ---------G -- -------

201                                                            250
eryBIV     mirralagep ltmwhdggvr rdl.lhveDv atAFaaaleh hdalag...g
ascF       lddiaknnkq ldmspgeqll d..lvhinDv crAFkiaidk lcelpseyvv
rfbJ       idclnkkqsc vkcttgeqir d..fifvdDv vnAYltilen rkevps..yt
strL       mirleadedt vlvvddqhgq ptwtadlaDr laAlgaaala gtapagiyha
Consensus  ---------- ---------- ------D- --AF----- ----------
```

FIG. 5A-2

```
           251                                                         300
eryBIV     twalgadrse plgDifravs gsva..rqtg spavdvvtvp apehaeaandf
ascF       sygvsnkyrv tlkElvsiye ..rv...nnv klninfgtre yrnrevmvpc
rfbJ       eyqvgtgagv slkDflvylq ntmm...pgs ssifefgaie qrdneimfsv
strL       tntggttwna lapEtfrllg adparvrptt slalarpavr .prysvldqs
Consensus  ---------- ---------- ---------- ---------- ----------

301                                              345
eryBIV     rsddidstef rsrtgwrprv sltdgidrtv aaltpteeh ......
ascF       .tniqnl... ...pdwevvi plsqglky.. .......... ......
rfbJ       .annknlkam gwkpnfdykk gieellkrl. .......... ......
strL       rwkaaglepl rhw.....ra altesf.... palcgragrp vpgpr
Consensus  ---------- ---------- ---------- ---------- ----

FIG. 5A-3
```

```
          1                                                                                    50
eryBVII   ..........  ..........  ......Vagg  feftpdpkqD  rRGlFvspLq  deaFvgavGh
strM.     ..........  ..vrplsVqga  wlsetrafaD  dRGeFqelYs  arsLrgalGy
rfbC      ........vm  iviktaIpdv  lilepkvfgD  eRGfFfesYn  qqtFeeliGr
rfbF      .........m  kctklsIpev  ilfeprifeD  dRGhFfesFn  lakFqesiGr
ascE      lgvivphylm  ifkkldIegc  yliefnkfiD  sRGtFvktFh  sdfFsen.Gi
Consensus ----------  ----------  ---------I  ----------  ---F----G-

51                                                                                   100
eryBVII   rfpvaqmmhi  vSargvlRGl  HFtttppgqc  KyVycarGra  LDVivDiRvg  Ylvstpyvae
strM      dpgvaqvnrs  vSrrgvlRGv  HFaqlppsqa  KyVtclsGav  LDVvvDiRtg  Yltsqgyaag
rfbC      kvtfvqdnhs  kSkknVlRGl  HFqrgenaqg  KlVrcavGev  FDVavDiRke  Ykatnyysps
rfbF      qvtfvqsnes  ySkqnViRGl  HYq.virpqg  KlVrvveGev  FDIavDlRks  Ymvtdywype
ascE      vldmreefys  iSaknViRGm  HFqmppaehd  KlVycvnGav  LDVilDiRkd  Yktssvhnve
Consensus ----------  -S---V-RG-  HF--------  K-V----G--  LDV--D-R--  -Y--------

101                                                                                  150
eryBVII   SpTFgkWdaV  eMdtehfrav  YfprGtaHaF  laLeddtlms
strM      SpTYraWeaV  rLddph.rsl  YveaGlgHsF  maLtddavvv
rfbC      SpTFgqWvgV  nLsaenkrql  WipeGfaHgF  vtLseyaefl
rfbF      SpTFgqWvgV  lLsdknnhql  WipeGfgHgF  qvLspsakfq
ascE      SkTYgeYfsI  eLsyenslal  WvpkGlaHgF  lsLadnsimf
Consensus S-TF--W--V  -L--------  W---G---H-F  --L-------
```

FIG. 5B-1

```
           151                                                            200
eryBVII    yEqaIdpfdp alglpwpadl evvlsDrdtv avdletarrr gmlpdyadcl
  strM     rEhgVhpldp dlgiawpdgi epvlsEkdrq apgiaemerr glipdyeecl
  rfbC     sEgsIlwnde aigiewp... fsqlpE.... ...lsakdaa aplldqallt
  rfbF     hDrcIrfnds dinikwk... egiisEqqvi eyklsskdis gnsladaevf
  ascE     cDsgIkwnsf gfkwpid... npiisEkdns lcyfdefdss f.........
Consensus  -E--I----- ---------- ----E----- ---------- ----------

201        212
eryBVII    geepastgr.. tg
  strM     afrrslcerg  tg
  rfbC     e.........  ..
  rfbF     ..........  ..
  ascE     ..........  ..
Consensus  ----------  --
```

```
           1                                                         50
eryCIV     ..........mk raltdLaifg gpeaFlhtly vgrptVgd.. ....rerFfa
eryCI      .........md  vpfldLqa.. ayleLrsdid qAcrrVlg.. ....sgwY..
ascC       ...msqeelr   qqiaeLvaq. aetaMapkpf eAgksVvpps gkvigtkelq
dnrJ       ..........   vstyvWqyln eyreeradil dAvetVfe.. ....sgqL..
prg1       ..........   .......... .......... .......... ..........
strS       ..........   ..mssFqelp rwpqLtdddi eAavaalr.. ....snrL..
Consensus  ----------   ---------- ----L----- -A---V---- ----------

51                                                        100
eryCIV     rlewalnnnw   Ltnggplvre FEgrvAdL.. aGvrHcVatc natvAlqLvL
eryCI      ..........   Lhgpe..nea FEaeFAaY.. cenaHcVtvg SGcdAleLsL
ascC       lmveasldgw   L.ttgrfnda FEkkLgeYl. .Gvpyvlttt SGssAnlLAL
dnrJ       ilgts..vrs   .......... FEeeFAaY.. hGlpyctgvd nGtnAlvLgL
prg1       ..sgp...igq  LEaeFlaFld hGvryaVtfn SGtsAllaAy
strS       vgqgnstvee   FEaaLAa..g qGveHaVavs tGtaAvhLAL
Consensus  L---------   ---------- FE---A-Y-- -G---H-V--- SG---A---LAL 101                                                       150
eryCIV     rAs.......  .dV..sgEVV mPsmTFaaTa haaswlGleP VFcDVDpeTg
eryCI      vAL.......  .gVgqGDEVI vPshTFiaTw lgV.pvGAvP VpVEpEgvsh
ascC       tALtspklgv  ralkPGDEVI tvaagFptTv nptiqnGliP VFVDVDipT.
dnrJ       rAL.......  .gIgPGDEVV tvsnTaapTv vaIdavGAtP VFVDVhe...
prg1       .gVreGvEaa  gPalTYhaal spVfalrgdv VLVDIDpvsr
strS       .dVgPGDEVI  vPthTFigsa spVtylGArP VFaDVtpdTh
hAL.......
Consensus  -AL-------  --V-PGDEVI -P--TF--T- --V---GA-P VFVDVD--T-
```

FIG. 5C-2

```
                                                                                              200
eryCIV     .....lLDP ehVaslVTpr TgAIigvVHlW GrpapvEale klAAeHqvkl
eryCI      t......LDP alVEqAITpr TaAIlpVHly GhpaDLDalr aIAdrHgLal
ascC       ....ynvna sIEAAVsDk TkAImiaHtl GnlfDLaeVr rVAdkynLwl
dnrJ       ...enylMDt grlrsvigpr TrcllpVHly GqsvDMtpVl elAaeHdLkV
prg1       g......LDP kaIEAAITEn TrvVtvVHqw GhpcDMDaIl gVAerygLrV
strS       c......LDP dsVksllgEr TkAIvvVHin GiaaDMaalt aVAaeagvpV
Consensus  -------LDP --VEAAITE- T-AI--VH-Y G----DMD-V- -IA--H-L-V 201                                                                                 250
eryCIV     ffDaAhAlGc tagGrpVGaF GnaevFS.Fh atKavtsf.E GGAIVTdDglL
eryCI      VEDvAQAvGa rhrGhrVGag snaaaFS.FY PgKnlgAlGD GGAVVTtDpaL
ascC       IEDccdAlGs tYdGkmaGtF GdigtvS.FY Pahhi.tm.GE GGAVfTqsaeL
dnrJ       lEDcAQAhGa rrhGrlVGtq GhaaaFS.FY PtKvlgAyGD GGAVVTpDaev
prg1       lEDcshAhGs rYkGkvpGtF GdaavFS.Lq anKavyA.GE GGilvTdDalv
strS       IEDaAQAlGt eigGrpIGgF GdlacvSlFF eqKvitsgGE GGAVITdnpvy
Consensus  IED-AQA-G- -Y-G--VG-F G----FS-FY P-K---A-GE GGAVVT-D--L 251                                                                                 300
eryCIV     aDRiRaMhn FGiapdk... .......... .......... ...lvtdvG
eryCI      aERiRlLRn YG....sk.. .......... .......... qk.YvhevrG
ascC       ksiiesFRd WGrdcycapg cdntckkrfg qqlgslpfgy dhkYtyshlG
dnrJ       drRlRrLRy YG......mg .......... .......... eryYvvdtpG
prg1       qDRatLat tG....t.. .......... .......... ......vpG
strS       aERvRrLRs hGegpvsgs. .......... .......... pgmiwahevG
Consensus  -ER-R-LR- YG-------- ---------- ---------- ---y----G
```

```
                 301                                                           350
eryCIV     tNgkMsEcaA AmgltsLdaF aetrvhnrln halysdeLrd vrGisvhafd
eryCI      tNaRLdELQA AvlrvkLrhL DdWnarRttl aqhyqteLkd vpGitlpeth
ascC       yNikitDMQA AcglaqLepi EeFvekRkan fkylkdaLqs cadf.ielpe
dnrJ       hNsRLdEvQA eilrrkLrrL DaYvegRrav arryeegLgd ldGlvlpt..
prgI       lghRr..... .......... .......... .......... ..........
strS       yNvRLtsvQA psaspsnkrL gdLveaRrrn aaylserLag veGlelpvep
Consensus  -N-RL-E-QA A-----L--L D-W-----R- ---------- -G--------

351                                                           400
eryCIV     pgeqnnyqYv iisVdsaatg idr..dqLqa iLraekVvaq pyFspgcHqm
eryCI      pwads..aWh lFvlrcenrD .....hLqr  hLtdagVqtl ihYptpvHls
ascC       atensdpsWf gFpI.tlkeD sgvsridLvk fLdeakVgtr llFagnltrq
dnrJ       iaegndhvYy vYvVrhperD .......... rile aLtaydIhln isYpwpvHtm
prgI       .......... .......... .......... .......... ..........
strS       p...gtthaYw kYaVrvvpgD grrsaadiaa hLrsrgVpvl lrYpypLHkq
Consensus  -------W-- -Y------D- ---------- -L-----V--- --Y----H--
```

FIG. 5C-3

```
        401                                                          450
eryCIV  qpYrte...p  plrLentEqL  sdrvLaLPtg  PavssEdirr  Vcdiirlaat
eryCI   paYAdlgl.p  pGsFpvaEsL  agevLsLPig  PhLsrEaaDh  VIatlkaga
ascC    pyFhdvkyRv  vGeLtntDRi  mnqtFwigiy  PgLthDhlDy  VVskfeeffg
dnrJ    sgFAhlg.Yg  pGdLpvtERL  ageiFsLPmy  PsLrpDaqEk  VIdavrevvg
prgl    ..........  ..........  ..........  ..........  .........
strS    paFAe...Yh  gvsLpvaERL  sqellaLPsh  PgLveghlDh  aVeevrkava
Consensus --FA---Y-  -G-L---ERL  ----L--LP--  P-L---E--D-  VV------

451         468
eryCIV  sgelinaqwd  qrtrngs
eryCI   ..........  .......
ascC    lnf.......  .......
dnrJ    sl........  .......
prgl    ..........  .......
strS    s.........  .......
Consensus ---------  -------
```

FIG. 5C-4

```
             1                                                        50
eryBV        vrVlltsfAh rtHFqGlVPL AWALRtAGHD VRVaaqPALT DaVigAGLTA
eryCIII      mrVvfssmAs ksHLfGlVPL AWAFRaAGHE VRVvasPALT EdItaAGLTA
dnrS         mkVlvtafAm daHFnGvVPL AWALRaAGHD VRVasqPALT DsItrAGLTA
Consensus    --V-----A- --HF-G-VPL AWALR-AGHD VRV---PALT D-I--AGLTA 51                                                      100
eryBV        VPVGsDhrlf divpevaaqV hrysfylDFy hreqelhswE fLlgmqeats
eryCIII      VPVGtDvdlv dfmthaghdI idyvrslDFs erdpatltwE hLrgmqtvlt
dnrS         VPVGtDhqvq aamgamapgV falhlnpDYl enrpelldlE fLeastsmlt
Consensus    VPVG-D---- ---------V -------DF- ---------E -L--------

101                                                     150
eryBV        rwvYpvvnnD sFVaeLVdFa rdWRPDLVlW EPFTFagaVA aracGaahAR
eryCIII      ptfYalmspD tLIegMVsFc rkWRPDLViW EPLTFaapIA gavtGtphAR
dnrS         aafYaqinnD sMIdeMVdFa awWRPDLVvW EPFTFggaVA aqvtGaaqAR
Consensus    ---Y-----D --I--MV-F- --WRPDLV-W EPFTF---VA ----G---AR
```

FIG. 5D-1

```
              151                                                                    200
    eryBV     LLWGsDltgy  lavGqwsVDq  lPpsfRLdTg  meTVvaRtlp  YNG..asVVP  dWLkkgsatr
    eryCIII   LLWGpDittr  arqnFlgllp  dqPeEhRegp  LaeWLTwtle  kyGgpaFdeE
              frgrFqaqrl  rrPpEdRpdp  LgtWLTevag  rfGv.eFgeD
    dnrS      LLWGpDlflr  vhdrFqqvlh  evPaErRdda  LeeWLTwtle  rhGa.aFgpE
    Consensus LLWG-D----  ------F---  --P-E-R---  L--WLT----  --G---F--E 201                                                                    250
    eryBV     lavGqwsVDq  lPpsfRLdTg  meTVvaRtlp  YNG..asVVP  dWLkkgsatr
    eryCIII   vvvGqWtIDp  aPaaiRLdTg  lkTVgmRyvd  YNG..psVVP  eWLhdeperr
    dnrS      visGhwtIDq  mPpsvRFaTa  rpTVpmRfvp  YNGpvpaVVP  pWLradpgrp
    Consensus ---G-W-ID-  -P----RL-T  --TV---R--  YNG----VVP  -WL-------

251                                                                    300
    eryBV     RIciTgGfsg  lgla.adadq  fartLaqlar  fDgEIVvTgs  gpdtsav...
    eryCIII   RVclTlGiss  rensigqvs.  ieellgavgd  vDaEIIaTfd  aqqlegvani
    dnrS      RVllTqGite  rstgftglpr  agellasiae  lDaEVVaTvk  aeereglppl
    Consensus RV--T-G---  ----------  ---L------  -D-EIV-T--  ----------
```

FIG. 5D-2

```
            301                                                    350
eryBV       PdNIRlVdfv pMgvlLqnCA AiIHHGGaGt WaTAlhHGIP QisvaheWDc
eryCIII     PhNVRtVgfv pMhalLptCA AtVHHGGpGs WhTAaiHGVP QvilpdgWDt
dnrS        PgNVRvVdsl sLhvvLpsCA AvVHHGGaGt WaTAalHGVP QlalawqWDd
Consensus   P-NVR-V--- -M---L--CA A-VHHGG-G- W-TA--HGVP Q------WD- 351                                                    400
eryBV       mlRgqqtaeL GAGIyLrp.. devdadslas altqVveDPt ytenAvklRe
eryCIII     gvRaqrtqeF GAGIaLp..v peltpdqlre svkrVldDPa hragAarmRd
dnrS        vfRagqlekL GAGIfLpphg egasagrvrd rlaqVlaEPs frqgAariRa
Consensus   --R------L GAGI-L---- ---------- ----V--DP- ----A---R-

401                             433
eryBV       EaLsdPtPqe IVprlEeLtr rhag...... ...
eryCIII     DmLaePsPae VVgicEeLaa grrepr.... ...
dnrS        EmLrtPaPga VVptlEqLta rhrapagqgv rh
Consensus   E-L--P-P-- VV---E-L-- ---------- ---
```

FIG. 5D-3

```
           1                                                   50
eryCVI     MYegg.fAel YDrfyrgRgK DYaaeaaqva rlvrdrlpsA ssLLDVACGT
srmX       MYendsaAev YDllyqdR.K DYageaarvt dlirertpdA asLLDIACGT
rdmD       MYgad.lArv YDlvhreRgK DYrardrggr rrgpaeqagA grLLDVACGT
Consensus  MY-----A-- YD-----R-K DY-------- ---------A --LLDVACGT 51                                                 100
eryCVI     GtHLrrFAdL FddVtGlELS aaMievArpq LgGIpvlqGD MRdFaLdreF
srmX       GtHLeaFAkL YdrVsGlELS ewMaarAeer LpGVtlhrGD MRaFdLgetF
rdmD       GgHLrhFAdL FahVeGvELS epMaeeAraa LpGVtvhaGD MRdFrLgttF
Consensus  G-HL--FA-L F--V-G-ELS --M---A--- L-GV----GD MR-F-L---F 101                                                150
eryCVI     DaVtCMFsSI GhMrdgAELd qAlasfARHL apgGVvvVEP WWFpEdFlDG
srmX       DaVvCMFsSI GyLettADLe dAvaamARHL tadGVlaVEP WYFpDtFlDG
rdmD       DvVtCMFgSV GyMtsvAELg rAlrmfARHL epgGVavVDP WWFyEtFaDG
Consensus  D-V-CMF-SI G-M---AEL- -A----ARHL ---GV--VEP WWF-E-F-DG
```

FIG. 5E-1

```
             151                                                    200
   eryCVI    yVagdvvrd. .gdltIsRVS HSvRaGgatr MEIHWvVAda vnGprHhvEh
     srmX    hVsthalrta pgdqgVaRVS HStReGgrtr MEIHYlIAht aeGirHrsEv
     rdmD    hVsadivtv. .dgvtVsRVS HSaRrGrtsh MDVHFvVAep gaGaqHfvDt
Consensus    -V-------- -----V-RVS HS-R-G---- MEIH--VA-- --G--H--E-

201                                       241
   eryCVI    yeitLFeRqq YEkAFtaAGc aVqYleggps grGLFvGvRg
     srmX    dyltLFsRae YEaAYrkAGl dVeYvvtgeg spGFFlGtRr
     rdmD    hiisLFsRse YEqAFrdAGf aVeYlpeaps grGLFvGvRg
Consensus    ----LF-R-- YE-AF--AG- -V-Y------ --GLF-G-R- -
```

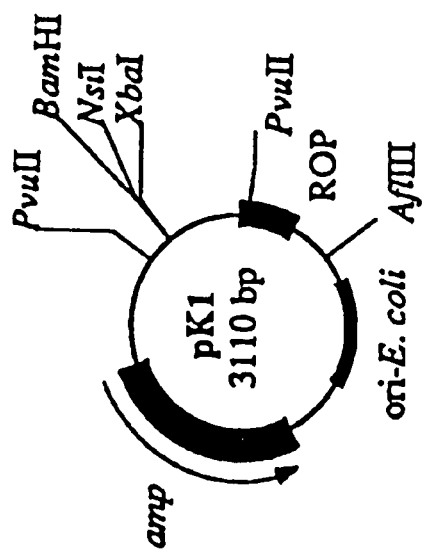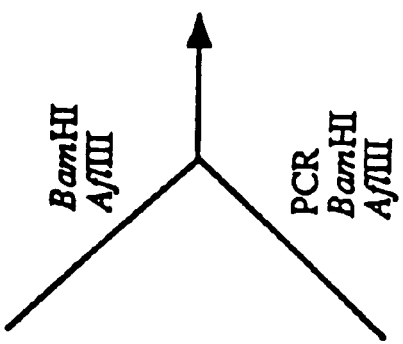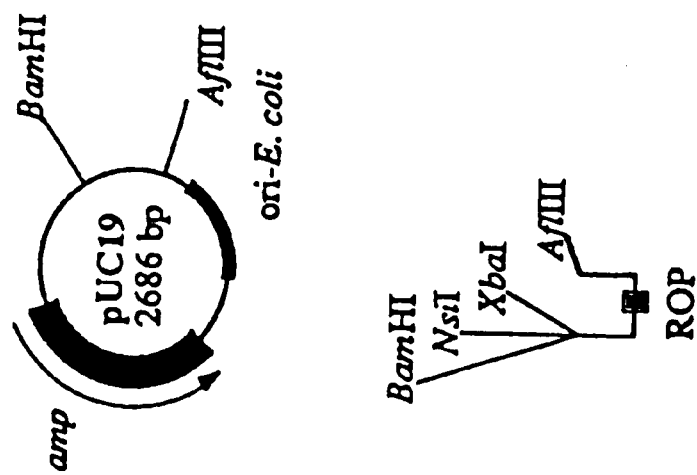
FIG. 9A

SEQUENCE LISTING (1) GENERAL INFORMATION:

-continued (iii) NUMBER OF SEQUENCES: 60

(2) INFORMATION FOR SEQ ID NO:1:

(i) SEQUENCE CHARACTERISTICS:
        (A) LENGTH: 3756 base pairs
        (B) TYPE: nucleic acid
        (C) STRANDEDNESS: single
        (D) TOPOLOGY: linear (xi) SEQUENCE DESCRIPTION: SEQ ID NO:1:

```
CACGCCGACG CGATCGCGCG GCACATCGAC GCCTGGCTGG GCGGAGGGAA TTCATGACCA      60
CGACCGATCG CGCCGGGCTG GGCAGGCAGC TCCAGATGAT CCGCGGCCTG CACTGGGGTT     120
ACGGCAGCAA CGGCGACCCT TACCCGATGC TGCTGTGCGG ACACGACGAC GACCCGCAGC     180
GCCGGTACCG CTCGATGCGC GAGTCCGGTG TGCGGCGCAG GACCGAGACG TGGGTGGTGG     240
CCGACCACGC CACCGCCCGG CAGGTGCTCG ACGACCCCGC GTTCACCCGC GCCACCGGAC     300
GCACACCGGA ATGGATGCGG GCCGCGGGCG CGCCACCCGC CGAGTGGGCC CAGCCGTTCC     360
GGGACGTGCA CGCCGCGTCC TGGGAAGGCG AGGTCCCCGA CGTCGGGGAA CTGGCGGAGA     420
GCTTCGCCGG TCTGCTCCCC GGCGCGGGCG CGCGGCTGGA CCTGGTCGGC GACTTCGCCT     480
GGCAGGTACC GGTGCAGGGC ATGACCGCCG TGCTCGGCGC AGCCGGAGTG CTGCGCGGCG     540
CCGCGTGGGA CGCCCGCGTC AGCCTGGACG CCCAGCTCAG CCCGCAGCAG CTCGCGGTGA     600
CCGAAGCAGC GGTCGCGGCA CTGCCCGCCG ACCCCGCACT GCGCGCCCTG TTCGCCGGGG     660
CCGAGATGAC CGCGAACACC GTGGTCGACG CGGTCCTGGC CGTCTCGGCC GAACCGGGGC     720
TGGCCGAACG GATCGCCGAC GACCCCGCCG CCGCGCAGCG AACCGTCGCC GAGGTGCTGC     780
GCCTGCACCC GGCATTGCAC CTGGAGCGGC GCACGGCCAC CGCAGAGGTG CGGCTCGGCG     840
AGCACGTGAT CGGCGAAGGC GAGGAGGTCG TGGTCGTCGT CGCGGCGGCC AACCGCGACC     900
CGGAGGTCTT CGCCGAGCCC GACCGCCTCG ACGTGGACCG CCCCGACGCC GACCGCGCGC     960
TGTCGGCACA TCGCGGCCAC CCCGGCAGGC TGGAGGAGCT GGTCACCGCG CTCGCCACCG    1020
CCGCACTGCG GGCCGCGGCC AAGGCGCTGC CCGGACTCAC GCCCAGCGGC CCGGTCGTCC    1080
GGCGCCGCCG ATCACCCGTC CTGCGGGGAA CCAACCGCTG CCCCGTCGAG CTCTGAGGAT    1140
TCCGCGATGC GCGTCGTCTT CTCCTCCATG GCCAGCAAGA GCCACCTCTT CGGCCTCGTC    1200
CCCCTCGCAT GGGCGTTCCG CGCGGCGGGG CACGAGGTCC GCGTGGTCGC GTCCCCGGCG    1260
CTCACCGAGG ACATCACCGC GGCCGGGCTG ACCGCCGTCC CGGTCGGCAC CGACGTCGAC    1320
CTCGTGGACT TCATGACCCA CGCGGGCCAC GACATCATCG ACTACGTCCG GAGCCTGGAC    1380
TTCAGCGAGC GGGACCCCGC CACCTTGACC TGGGAGCACC TGCGGGGCAT GCAGACCGTG    1440
CTCACCCCGA CCTTCTACGC CCTGATGAGC CCGGACACGC TCATCGAAGG CATGGTCTCG    1500
TTCTGCCGGA AGTGGCGGCC CGACCTGGTC ATCTGGGAGC CGCTCACCTT CGCCGCGCCC    1560
ATCGCGGGCG CGGTGACCGG AACGCCGCAC GCGCGGCTGC TGTGGGACC  CGACATCACC    1620
ACCCGGGCGC GGCAGAACTT CCTCGGCCTG CTGCCCGACC AGCCGGAGGA GCACCGGGAG    1680
GGCCCGCTCG CCGAGTGGCT CACCTGGACG CTGGAGAAGT ACGGCGGCCC GGCCTTCGAC    1740
GAGGAGGTGG TCGTCGGGCA GTGGACGATC GACCCCGCCC CGGCCGCGAT CAGGCTCGAC    1800
ACCGGCCTGA AGACCGTCGG GATGCGCTAC GTCGACTACA ACGGGCCGTC CGTGGTGCCG    1860
GAATGGCTGC ACGACGAGCC CGAGCGCCGC CGCGTGTGCC TCACGCTCGG GATCTCCAGC    1920
CGCGAGAACA GCATCGGGCA GGTCTCCATC GAGGAGCTGC TGGGTGCCGT CGGCGACGTC    1980
GACGCCGAGA TCATCGCGAC CTTCGACGCG CAGCAGCTAG AAGGCGTCGC GAACATCCCG    2040
```

```
CACAACGTCC GCACGGTCGG CTTCGTCCCG ATGCACGCGC TGCTGCCGAC CTGCGCGGCG    2100

ACGGTGCACC ACGGCGGACC CGGGAGCTGG CACACCGCGG CGATCCACGG CGTGCCGCAG    2160

GTGATCCTGC CCGACGGCTG GGACACCGGC GTGCGCGCGC AGCGCACGCA GGAATTCGGG    2220

GCGGGGATCG CGCTGCCCGT GCCCGAGCTG ACCCCCGACC AGCTCCGGGA GTCGGTGAAG    2280

CGGGTCCTCG ACGACCCGGC CCACCGCGCC GGCGCGGCGC GGATGCGCGA CGACATGCTC    2340

GCGGAGCCGT CACCGGCCGA GGTCGTCGGC ATCTGCGAGG AACTGGCCGC AGGAAGGAGA    2400

GAACCACGAT GACCACCGAC GCCGCGACGC ACGTGCGGCT CGGGCGTTCC GCGCTGCTCA    2460

CCAGCAGGCT CTGGCTCGGC ACGGTGAACT TCAGCGGACG CGTCGAGGAC GACGACGCGC    2520

TGCGCCTGAT GGACCACGCC CGGGACCGCG GCATCAACTG CCTCGACACC GCCGACATGT    2580

ACGGCTGGCG GCTCTACAAG GGCCACACCG AGGAGCTGGT GGGCAGGTGG CTGGCCCAGG    2640

GCGGCGGACG GCGCGAGGAC ACCGTGCTGG CGACCAAGGT CGGCGGCGAG ATGAGCGAGC    2700

GCGTCAACGA CAGCGGGCTG TCGGCGCGGC ACATCATCGC CTCCTGCGAG GGATCGCTGC    2760

GCAGGCTGGG CGTCGACCAC ATCGACGTCT ACCAGATGCA CCACATCGAC CGGTCCGCGC    2820

CGTGGGACGA GGTGTGGCAG GCCATGGACA GCCTCGTCGC CAGCGGCAAG GTCTCCTACG    2880

TCGGCTCGTC GAACTTCGCG GGCTGGCACA TCGCCGCCGC GCAGGAGAAC GCCGCCCGCC    2940

GCCACTCCCT GGGCATGGTC TCCCACCAGT GCCTGTACAA CCTGGCGGTC CGGCACGCCG    3000

AGCTGGAGGT GCTGCCCGCC GCGCAGGCCT ACGGGCTCGG CGTCTTCGCC TGGTCGCCGC    3060

TGCACGGCGG CCTGCTCAGC GGAGCGCTGG AGAAGCTGGC CGCGGGCACC GCGGTGAAGT    3120

CGGCGCAGGG CCGTGCGCAG GTGCTGTTGC CGTCCCTGCG CCCGGCGATC GAGGCCTACG    3180

AGAAGTTCTG CCGCAACCTC GGCGAAGACC CGGCCGAGGT GGGGCTCGCA TGGGTGCTGT    3240

CCCGGCCCGG CATCGCCGGC GCCGTCATCG GCCCGCGAAC CCCCGAGCAG CTCGACTCCG    3300

CGCTGAAGGC GTCCGCGATG ACCCTGGACG AGCAGGCGCT GTCCGAACTG GACGAGATCT    3360

TCCCCGCGGT GGCCTCCGGC GGCGCGGCGC CGGAAGCCTG GTTGCAGTGA GCACAAGAGG    3420

AACCGAGAAA GGATACGGCT GGTGAGCGTG AAGCAGAAGT CAGCGTTGCA GGACCTGGTC    3480

GACTTCGCCA AGTGGCACGT GTGGACCAGG GTGCGGCCGT CCAGCCGTGC GCGCCTGGCC    3540

TACGAGCTGT TCGCCGACGA CCACGAGGCC ACGACCGAGG GCGCCTACAT CAACCTCGGC    3600

TACTGGAAGC CCGGGTGCGC CGGCCTGGAG GAGGCCAACC AGGAGCTGGC GAACCAGCTC    3660

GCCGAGGCCG CGGGGATCAG CGAGGGCGAC GAGGTGCTCG ACGTCGGGTT CGGGCTCGGC    3720

GCGCAGGACT TCTTCTGGCT CGACCTGCAG CCAGCT                              3756

(2) INFORMATION FOR SEQ ID NO:2:

(i) SEQUENCE CHARACTERISTICS:
         (A) LENGTH: 8051 base pairs
         (B) TYPE: nucleic acid
         (C) STRANDEDNESS: single
         (D) TOPOLOGY: linear (xi) SEQUENCE DESCRIPTION: SEQ ID NO:2:

CGGGTTGCCG CACATCGCGC TGGGGAGATT CTTTGAATTT CGCCCGTAGC ACCGACCTGG      60

AAAGCGAGCA AATGCTCCGG TGAATGGGAT CAGTGATTCC CCGCGTCAAT TGATCACCCT     120

TCTGGGCGCT TCCGGCTTCG TCGGGAGCGC GGTTCTGCGC GAGCTGCGCG ACCACCCGGT     180

CCGGCTGCGC GCGGTGTCCC GCGGCGGAGC GCCCGCGGTT CCGCCCGGCG CCGCGGAGGT     240

CGAGGACCTG CGCGCCGACC TGCTGGAACC GGGCCGGGCC GCCGCCGCGA TCGAGGACGC     300
```

| | | | | | |
|---|---|---|---|---|---|
| CGACGTGATC | GTGCACCTGG | TGGCGCACGC | AGCGGGCGGT | TCCACCTGGC | GCAGCGCCAC | 360 |
| CTCCGACCCG | GAAGCCGAGC | GGGTCAACGT | CGGCCTGATG | CACGACCTCG | TCGGCGCGCT | 420 |
| GCACGATCGC | CGCAGGTCGA | CGCCGCCCGT | GTTGCTCTAC | GCGAGCACCG | CACAGGCCGC | 480 |
| GAACCCGTCG | GCGGCCAGCA | GGTACGCGCA | GCAGAAGACC | GAGGCCGAGC | GCATCCTGCG | 540 |
| CAAAGCCACC | GACGAGGGCC | GGGTGCGCGG | CGTGATCCTG | CGGCTGCCCG | CGGTCTACGG | 600 |
| CCAGAGCGGC | CCGTCCGGCC | CCATGGGGCG | GGGCGTGGTC | GCAGCGATGA | TCCGGCGTGC | 660 |
| CCTCGCCGGC | GAGCCGCTCA | CCATGTGGCA | CGACGGCGGC | GTGCGCCGCG | ACCTGCTGCA | 720 |
| CGTCGAGGAC | GTGGCCACCG | CGTTCGCCGC | CGCGCTGGAG | CACCACGACG | CGCTGGCCGG | 780 |
| CGGCACGTGG | GCGCTGGGCG | CCGACCGATC | CGAGCCGCTC | GGCGACATCT | TCCGGGCCGT | 840 |
| CTCCGGCAGC | GTCGCCCGGC | AGACCGGCAG | CCCCGCCGTC | GACGTGGTCA | CCGTGCCCGC | 900 |
| GCCCGAGCAC | GCCGAGGCCA | ACGACTTCCG | CAGCGACGAC | ATCGACTCCA | CCGAGTTCCG | 960 |
| CAGCCGGACC | GGCTGGCGCC | CCCGGGTTTC | CCTCACCGAC | GGCATCGACC | GGACGGTGGC | 1020 |
| CGCCCTGACC | CCCACCGAGG | AGCACTAGTG | CGGGTACTGC | TGACGTCCTT | CGCGCACCGC | 1080 |
| ACGCACTTCC | AGGGACTGGT | CCCGCTGGCG | TGGGCGCTGC | GCACCGCGGG | TCACGACGTG | 1140 |
| CGCGTGGCCG | CCCAGCCCGC | GCTCACCGAC | GCGGTCATCG | GCGCCGGTCT | CACCGCGGTA | 1200 |
| CCCGTCGGCT | CCGACCACCG | GCTGTTCGAC | ATCGTCCCGG | AAGTCGCCGC | TCAGGTGCAC | 1260 |
| CGCTACTCCT | TCTACCTGGA | CTTCTACCAC | CGCGAGCAGG | AGCTGCACTC | GTGGGAGTTC | 1320 |
| CTGCTCGGCA | TGCAGGAGGC | CACCTCGCGG | TGGGTATACC | CGGTGGTCAA | CAACGACTCC | 1380 |
| TTCGTCGCCG | AGCTGGTCGA | CTTCGCCCGG | GACTGGCGTC | CTGACCTGGT | GCTCTGGGAG | 1440 |
| CCGTTCACCT | TCGCCGGCGC | CGTCGCGGCC | CGGGCCTGCG | GAGCCGCGCA | CGCCCGGCTG | 1500 |
| CTGTGGGGCA | GCGACCTCAC | CGGCTACTTC | CGCGGCCGGT | TCCAGGCGCA | ACGCCTGCGA | 1560 |
| CGGCCGCCGG | AGGACCGGCC | GGACCCGCTG | GCACGTGGC | TGACCGAGGT | CGCGGGGCGC | 1620 |
| TTCGGCGTCG | AATTCGGCGA | GGACCTCGCG | GTCGGGCAGT | GGTCGGTCGA | CCAGTTGCCG | 1680 |
| CCGAGTTTCC | GGCTGGACAC | CGGAATGGAA | ACCGTTGTCG | CGCGGACCCT | GCCCTACAAC | 1740 |
| GGCGCGTCGG | TGGTTCCGGA | CTGGCTCAAG | AAGGGCAGTG | CGACTCGACG | CATCTGCATT | 1800 |
| ACCGGAGGGT | TCTCCGGACT | CGGGCTCGCC | GCCGATGCCG | ATCAGTTCGC | GCGGACGCTC | 1860 |
| GCGCAGCTCG | CGCGATTCGA | TGGCGAAATC | GTGGTTACGG | GTTCCGGTCC | GGATACCTCC | 1920 |
| GCGGTACCGG | ACAACATTCG | TTTGGTGGAT | TTCGTTCCGA | TGGGCGTTCT | GCTCCAGAAC | 1980 |
| TGCGCGGCGA | TCATCCACCA | CGGCGGGGCC | GGAACCTGGG | CCACGGCACT | GCACCACGGA | 2040 |
| ATTCCGCAAA | TATCAGTTGC | ACATGAATGG | GATTGCATGC | TACGCGGCCA | GCAGACCGCG | 2100 |
| GAACTGGGCG | CGGGAATCTA | CCTCCGGCCG | GACGAGGTCG | ATGCCGACTC | ATTGGCGAGC | 2160 |
| GCCCTCACCC | AGGTGGTCGA | GGACCCCACC | TACACCGAGA | ACGCGGTGAA | GCTTCGCGAG | 2220 |
| GAGGCGCTGT | CCGACCCGAC | GCCGCAGGAG | ATCGTCCCGC | GACTGGAGGA | ACTCACGCGC | 2280 |
| CGCCACGCCG | GCTAGCGGTT | TCCGACCGAC | AAGTCCGTCC | GACAGCACAC | CTCCGGAGGG | 2340 |
| AGCAGGGATG | TACGAGGGCG | GGTTCGCCGA | GCTTTACGAC | CGGTTCTACC | GCGGCCGGGG | 2400 |
| CAAGGACTAC | GCGGCCGAGG | CCGCGCAGGT | CGCGCGGCTG | GTCAGAGACC | GCCTGCCCTC | 2460 |
| GGCTTCCTCG | CTGCTCGACG | TGGCCTGCGG | GACCGGCACC | CACCTGCGCC | GGTTCGCCGA | 2520 |
| CCTCTTCGAC | GACGTGACCG | GGCTGGAGCT | GTCGGCGGCG | ATGATCGAGG | TCGCCCGGCC | 2580 |
| GCAGCTCGGC | GGCATCCCGG | TGCTGCAGGG | CGACATGCGC | GACTTCGCGC | TGGATCGCGA | 2640 |
| GTTCGACGCC | GTCACCTGCA | TGTTCAGCTC | CATCGGGCAC | ATGCGCGACG | CGCCGAGCT | 2700 |

```
GGACCAGGCG CTGGCGTCCT TCGCCCGCCA CCTCGCCCCC GGCGGCGTCG TGGTGGTCGA    2760

ACCGTGGTGG TTCCCGGAGG ACTTCCTCGA CGGCTACGTG GCCGGTGACG TGGTGCGCGA    2820

CGGCGACCTG ACGATCTCGC GCGTCTCGCA CTCCGTGCGC GCCGGCGGCG CGACCCGGAT    2880

GGAGATCCAC TGGGTCGTGG CCGACGCGGT GAACGGTCCG CGGCACCACG TGGAGCACTA    2940

CGAGATCACG CTCTTCGAGC GGCAGCAGTA CGAGAAGGCC TTCACCGCGG CCGGTTGCGC    3000

TGTGCAGTAC CTGGAGGGCG GACCCTCCGG ACGCGGGTTG TTCGTCGGTG TGCGCGGATG    3060

ACCCGTGCGT CGCGTTTTCC GTTCCTGGCA CAGGTGATCC GCTCCACGGG CCCTTTCCCC    3120

GCCGTGACCG GACCCTTACA GTGAGTGCGG GTCTTGATCG ACAACGCCCG GCGGCAGCAA    3180

GCGGAGCCGT CGACGACACC GCAGGGAGAG TCGATGGGTG ATCGGACCGG CGACCGGACG    3240

ATTCCGGAAT CCTCGCAGAC CGCAACGCGT TTCCTGCTCG GCGACGGCGG AATCCCCACC    3300

GCCACGGCGG AAACCCACGA CTGGCTGACC CGCAACGGCG CCGAGCAGCG GCTCGAGGTG    3360

GCGCGCGTGC CGTTCAGCGC CATGGACCGC TGGTCGTTCC AGCCCGAGGA CGGCAGGCTC    3420

GCCCACGAGT CCGGGCGCTT CTTCTCCATC GAGGGCCTGC ACGTGCGGAC GAACTTCGGC    3480

TGGCGGCGGG ACTGGATCCA GCCCATCATC GTGCAGCCCG AGATCGGCTT CCTCGGCCTC    3540

ATCGTCAAGG AGTTCGACGG TGTGCTGCAC GTGCTGGCGC AGGCCAAGGC CGAGCCGGGC    3600

AACATCAACG CCGTCCAGCT CTCCCCGACC CTGCAGGCGA CCCGCAGCAA CTACACCGGC    3660

GTCCACCGCG GCTCGAAGGT CCGGTTCATC GAGTACTTCA ACGGCACGCG CCCGAGCCGG    3720

ATCCTCGTCG ACGTGCTCCA GTCCGAGCAG GGCGCGTGGT TCCTGCGCAA GCGCAACCGG    3780

AACATGGTCG TCGAGGTGTT CGACGACCTG CCCGAGCACC CGAACTTCCG GTGGCTGACC    3840

GTCGCGCAGC TGCGGGCGAT GCTGCACCAC GACAACGTGG TGAACATGGA CCTGCGCACC    3900

GTGCTGGCCT GCGTCCCGAC CGCCGTGGAG CGGGACCGGG CCGACGACGT GCTCGCGCGC    3960

CTGCCCGAGG GCTCGTTCCA GGCCCGGCTG CTGCACTCGT TCATCGGCGC GGGCACCCCG    4020

GCCAACAACA TGAACAGCCT GCTGAGCTGG ATCTCCGACG TGCGCGCCAG GCGCGAGTTC    4080

GTGCAGCGCG GCCGCCCGCT GCCCGACATC GAGCGCAGCG GGTGGATCCG CCGCGACGAC    4140

GGCATCGAGC ACGAGGAGAA GAAGTACTTC GACGTCTTCG GCGTCACGGT GGCGACCAGC    4200

GACCGCGAGG TCAACTCGTG GATGCAGCCG CTGCTCTCGC CGCCAACAA CGGCCTGCTC    4260

GCCCTGCTGG TCAAGGACAT CGGCGGCACG TTGCACGCGC TCGTGCAGCT GCGCACCGAG    4320

GCGGGCGGGA TGGACGTCGC CGAGCTGGCG CCTACGGTGC ACTGCCAGCC CGACAACTAC    4380

GCCGACGCGC CCGAGGAGTT CCGACCGGCC TATGTGGACT ACGTGTTGAA CGTGCCGCGC    4440

TCGCAGGTCC GCTACGACGC ATGGCACTCC GAGGAGGGCG GCCGGTTCTA CCGCAACGAG    4500

AACCGGTACA TGCTGATCGA GGTGCCCGCC GACTTCGACG CCAGTGCCGC TCCCGACCAC    4560

CGGTGGATGA CCTTCGACCA GATCACCTAC CTGCTCGGGC ACAGCCACTA CGTCAACATC    4620

CACGTGCGCA GCATCATCGC GTGCGCCTCG GCCGTCTACA CCAGGACCGC CGGATGAAAC    4680

GCGCGCTGAC CGACCTGGCC ATCTTCGGCG GCCCCGAGGC ATTCCTGCAC ACCCTCTACG    4740

TGGGCAGGCC GACCGTCGGG GACCGGGAGC GGTTCTTCGC CCGCCTGGAG TGGGCGCTGA    4800

ACAACAACTG GCTGACCAAC GGCGGACCAC TGGTGCGCGA GTTCGAGGGC CGGGTCGCCG    4860

ACCTGGCGGG TGTCCGCCAC TGCGTGGCCA CCTGCAACGC GACGGTCGCG CTGCAACTGG    4920

TGCTGCGCGC GAGCGACGTG TCCGGCGAGG TCGTCATGCC TTCGATGACG TTCGCGGCCA    4980

CCGCGCACGC GGCGAGCTGG CTGGGGCTGG AACCGGTGTT CTGCGACGTG GACCCCGAGA    5040

CCGGCCTGCT CGACCCCGAG CACGTCGCGT CGCTGGTCAC ACCGCGGACG GGCGCGATCA    5100
```

```
TCGGCGTGCA CCTCTGGGGC AGGCCCGCTC CGGTCGAGGC GCTGGAGAAG ATCGCCGCCG    5160

AGCACCAGGT CAAACTCTTC TTCGACGCCG CGCACGCGCT GGGCTGCACC GCCGGCGGGC    5220

GGCCGGTCGG CGCCTTCGGC AACGCCGAGG TGTTCAGCTT CCACGCCACG AAGGCGGTCA    5280

CCTCGTTCGA GGGCGGCGCC ATCGTCACCG ACGACGGGCT GCTGGCCGAC CGCATCCGCG    5340

CCATGCACAA CTTCGGGATC GCACCGGACA AGCTGGTGAC CGATGTCGGC ACCAACGGCA    5400

AGATGAGCGA GTGCGCCGCG GCGATGGGCC TCACCTCGCT CGACGCCTTC GCCGAGACCA    5460

GGGTGCACAA CCGCCTCAAC CACGCGCTCT ACTCCGACGA GCTCCGCGAC GTGCGCGGCA    5520

TATCCGTGCA CGCGTTCGAT CCTGGCGAGC AGAACAACTA CCAGTACGTG ATCATCTCGG    5580

TGGACTCCGC GGCCACCGGC ATCGACCGCG ACCAGTTGCA GGCGATCCTG CGAGCGGAGA    5640

AGGTTGTGGC ACAACCCTAC TTCTCCCCCG GGTGCCACCA GATGCAGCCG TACCGGACCG    5700

AGCCGCCGCT GCGGCTGGAG AACACCGAAC AGCTCTCCGA CCGGGTGCTC GCGCTGCCCA    5760

CCGGCCCCGC GGTGTCCAGC GAGGACATCC GGCGGGTGTG CGACATCATC CGGCTCGCCG    5820

CCACCAGCGG CGAGCTGATC AACGCGCAAT GGGACCAGAG GACGCGCAAC GGTTCGTGAC    5880

GACCTGCGCC ACAAGTGCCA GGAGGTTCGC TCCCCGATGA ACACAACTCG TACGGCAACC    5940

GCCCAGGAAG CGGGGGTCGC CGACGCGGCG CGCCCGGACG TCGACCGGCG GGCGGTCGTG    6000

CGGGCGCTGA GCTCGGAGGT CTCCCGCGTC ACCGGCGCCG GTGACGGTGA CGCCCACGTG    6060

CAGGCCGCCC GGCTCGCCGA CCTCGCCGCG CACTACGGGG CGCACCCGTT CACGCCGCTG    6120

GAGCAGACGC GTGCGCGGCT CGGCCTGGAC CGCGCGGAGT CGCCCACCT GCTCGACCTG     6180

TTCGGCCGCA TCCCGGACCT GGGCACCGCG GTGGAGCACG GTCCGGCGGG CAAGTACTGG    6240

TCCAACACGA TCAAGCCGCT GGACGCCGCA GGCGCACTGG ACGCGGCGGT CTACCGCAAG    6300

CCTGCCTTCC CCTACAGCGT CGGCCTGTAC CCCGGGCCGA CGTGCATGTT CCGCTGCCAC    6360

TTCTGCGTGC GGGTGACCGG TGCCCGCTAC GAGGCCGCAT CGGTCCCGGC GGGCAACGAG    6420

ACGCTGGCCG CGATCATCGA CGAGGTGCCC ACGGACAACC CGAAGGCGAT GTACATGTCG    6480

GGCGGGCTCG AGCCGCTGAC CAACCCCGGT CTCGGCGAGC TGGTGTCGCA CGCCGCCGGG    6540

CGCGGTTTCG ACCTCACCGT CTACACCAAC GCCTTCGCCC TCACCGAGCA GACGCTGAAC    6600

CGCCAGCCCG GCCTGTGGGA GCTGGGCGCG ATCCGCACGT CCCTCTACGG GCTGAACAAC    6660

GACGAGTACG AGACGACCAC CGGCAAGCGC GGCGCTTTCG AACGCGTCAA GAAGAACCTG    6720

CAGGGCTTCC TGCGGATGCG CGCCGAGCGG GACGCGCCGA TCCGGCTCGG CTTCAACCAC    6780

ATCATCCTGC CGGGACGGGC CGACCGGCTC ACCGACCTCG TCGACTTCAT CGCCGAGCTC    6840

AACGAGTCCA GCCCGCAACG GCCGCTGGAC TTCGTGACGG TGCGCGAGGA CTACAGCGGC    6900

CGCGACGACG GCCGGCTGTC GGACTCCGAG CGCAACGAGC TGCGCGAGGG CCTGGTGCGG    6960

TTCGTCGACT ACGCCGCCGA GCGGACCCCG GGCATGCACA TCGACCTGGG CTACGCCCTG    7020

GAGAGCCTGC GGCGGGGTGT GGACGCCGAG CTGCTGCGCA TCCGGCCGGA GACGATGCGT    7080

CCCACCGCGC ACCCCCAGGT CGCGGTGCAG ATCGACCTGC TCGGCGACGT CTACCTCTAC    7140

CGCGAGGCGG GCTTCCCGGA GCTGGAGGGC GCCACCCGCT ACATCGCGGG CCGGGTCACC    7200

CCGTCGACCA GCCTGCGCGA GGTGGTGGAG AACTTCGTGC TGGAGAACGA GGGCGTGCAG    7260

CCCCGCCCCG GCGACGAGTA CTTCCTCGAC GGCTTCGACC AGTCGGTGAC CGCACGGCTC    7320

AACCAGCTCG AACGAGACAT CGCCGACGGG TGGGAGGACC ACCGCGGCTT CCTGCGCGGA    7380

AGGTGAACCG GAGTTGCGAG TACGTGAGCT GGCGGTGGCG GGCGGTTTCG AGTTCACCCC    7440

CGACCCGAAG CAGGACCGGC GGGGCCTGTT CGTGTCTCCG CTGCAGGACG AGGCGTTCGT    7500
```

```
GGGCGCGGTG GGCCATCGGT TCCCCGTCGC CCAGATGAAC CACATCGTCT CCGCCCGGGG    7560

CGTGCTGCGC GGGCTGCACT TCACCACCAC CCCGCCGGGG CAGTGCAAGT ACGTCTACTG    7620

CGCGCGCGGC CGGGCGCTCG ACGTCATCGT CGACATCCGG GTCGGCTCGC CGACGTTCGG    7680

GAAGTGGGAC GCGGTGGAGA TGGACACCGA GCACTTCCGG GCGGTCTACT TCCCCAGGGG    7740

CACCGCGCAC GCCTTCCTCG CGCTTGAGGA CGACACCCTG ATGTCGTACC TGGTCAGCAC    7800

GCCGTACGTG GCCGAGTACG AGCAGGCGAT CGACCCGTTC GACCCCGCGC TGGGTCTGCC    7860

GTGGCCCGCG GACCTGGAGG TCGTGCTCTC CGACCGCGAC ACGGTGGCCG TGGACCTGGA    7920

GACCGCCAGG CGGCGAGGGA TGCTGCCCGA CTACGCCGAC TGCCTCGGCG AGGAGCCCGC    7980

CAGCACCGGC AGGTGACGGG TCCCGAGCAC GATCTGTTCG AAGTGGCGCA GGCGCTCGTC    8040

GTCGCGGTCG A                                                        8051
```

(2) INFORMATION FOR SEQ ID NO:3:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:3:

```
GATCCAGCGT CTGCAGGCAT GCTCTAGATA CAATTAAAGG CTCCTTTTGG AGCCTTTTTT    60

TTTGGAGATT TTCAACGT                                                 78
```

(2) INFORMATION FOR SEQ ID NO:4:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:4:

```
AGCTACGTTG AAAATCTCCA AAAAAAAAGG CTCCAAAAGG AGCCTTTAAT TGTATCTAGA    60

GCATGCCTGC AGACGCTG                                                 78
```

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:5:

```
GATCGCATGC TCTAGAGTAC GTGAGCTGGC GGTGGCGGGC                          40
```

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:6:

```
GATCCGGATC CGCATGCTTC ACCTGCCGGT GCTGGCGGG                           39
```

(2) INFORMATION FOR SEQ ID NO:7:

(i) SEQUENCE CHARACTERISTICS:

(A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:7:

GATCACATGT TCTTTCCTGC GTTATCCCCT G                                31

(2) INFORMATION FOR SEQ ID NO:8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:8:

GATCGGATCC ATGCATGTCT AGAGCATCGC AGGATGCTGC TGGC                  44

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:9:

GAATGCATCC TGGAAAGCGA GCAAATGCTC CGGTG                            35

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:10:

GATCTAGAGC TAGCCGGCGT GGCGGCGCGT G                                31

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:11:

GATCGCTAGC CGTGACCGGA CCCTTACAGT GAGTG                            35

(2) INFORMATION FOR SEQ ID NO:12:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:12:

GATCTAGACT TAAGTCATCC GGCGGTCCTG GTGTAGACGG C                     41

(2) INFORMATION FOR SEQ ID NO:13:

(i) SEQUENCE CHARACTERISTICS:
        (A) LENGTH: 38 base pairs
        (B) TYPE: nucleic acid (C) STRANDEDNESS: single
            (D) TOPOLOGY: linear (xi) SEQUENCE DESCRIPTION: SEQ ID NO:13:

GATCTTAAGA ACCGGAGTTG CGAGTACGTG AGCTGGCG                          38

(2) INFORMATION FOR SEQ ID NO:14:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:14:

GATCTAGACC TAGGTCACCT GCCGGTGCTG GCGGGCTC                          38

(2) INFORMATION FOR SEQ ID NO:15:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:15:

GATCCTAGGC CGCAGGAAGG AGAGAACCAC G                                 31

(2) INFORMATION FOR SEQ ID NO:16:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:16:

GATCTAGATT AATCACTGCA ACCAGGCTTC CGGC                              34

(2) INFORMATION FOR SEQ ID NO:17:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:17:

GATTAATTGG CCGCGGCGCC GCGCTCGTTA TG                                32

(2) INFORMATION FOR SEQ ID NO:18:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:18:

GATCTAGATA ATTAATCATA CGACTTCCAG TCGGGGTAG                         39

(2) INFORMATION FOR SEQ ID NO:19:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:19:

GATTAATTAA TGATCAAGCT GAAAATTGTT TGCATG          36

(2) INFORMATION FOR SEQ ID NO:20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:20:

GATCTAGACT GCCGGCTCAG CCTTCCCAGG TTCG          34

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:21:

GGAATTCAGA TCTATGCATT CTAGAA          26

(2) INFORMATION FOR SEQ ID NO:22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:22:

CGCGTTCTAG AATGCATAGA TCTGAATTCC TGCA          34

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:23:

GAATGCATCT GGCTGGGCGG AGGGAATTCA TG          32

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:24:

GATCTAGACT TAAGTCATCG TGGTTCTCTC CTTCCTGCGG C          41

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:25:

```
GATCCTTAAG CTCCGGAGGG AGCAGGGATG                                    30

(2) INFORMATION FOR SEQ ID NO:26:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:26:

GATCTAGACC TAGGTCATCC GCGCACACCG ACGAAC                              36

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:27:

GATCCTAGGC CGTCTACACC AGGACCGCCG G                                   31

(2) INFORMATION FOR SEQ ID NO:28:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:28:

GATCTAGATT AATCACCTTC CGCGCAGGAA GCCGC                               35

(2) INFORMATION FOR SEQ ID NO:29:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:29:

GATCTTAAGC CGCCACTCGA ACGGACACTC G                                   31

(2) INFORMATION FOR SEQ ID NO:30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:30:

GATCTAGATC AAGCCCCAGC CTTGAGGG                                       28

(2) INFORMATION FOR SEQ ID NO:31:

(i) SEQUENCE CHARACTERISTICS:
        (A) LENGTH: 1114 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:
```

```
Met Thr Thr Thr Asp Arg Ala Gly Leu Gly Arg Gln Leu Gln Met Ile
 1               5                  10                  15

Arg Gly Leu His Trp Gly Tyr Gly Ser Asn Gly Asp Pro Tyr Pro Met
                20                  25                  30

Leu Leu Cys Gly His Asp Asp Pro Gln Arg Arg Tyr Arg Ser Met
            35                  40                  45

Arg Glu Ser Gly Val Arg Arg Arg Thr Glu Thr Trp Val Val Ala Asp
        50                  55                  60

His Ala Thr Ala Arg Gln Val Leu Asp Asp Pro Ala Phe Thr Arg Ala
 65                  70                  75                  80

Thr Gly Arg Thr Pro Glu Trp Met Arg Ala Ala Gly Ala Pro Pro Ala
                85                  90                  95

Glu Trp Ala Gln Pro Phe Arg Asp Val His Ala Ala Ser Trp Glu Gly
                100                 105                 110

Glu Val Pro Asp Val Gly Glu Leu Ala Glu Ser Phe Ala Gly Leu Leu
                115                 120                 125

Pro Gly Ala Gly Ala Arg Leu Asp Leu Val Gly Asp Phe Ala Trp Gln
            130                 135                 140

Val Pro Val Gln Gly Met Thr Ala Val Leu Gly Ala Ala Gly Val Leu
145                 150                 155                 160

Arg Gly Ala Ala Trp Asp Ala Arg Val Leu Asp Ala Gln Leu Ser
                165                 170                 175

Pro Gln Gln Leu Ala Val Thr Glu Ala Ala Val Ala Ala Leu Pro Ala
            180                 185                 190

Asp Pro Ala Leu Arg Ala Leu Phe Ala Gly Ala Glu Met Thr Ala Asn
            195                 200                 205

Thr Val Val Asp Ala Val Leu Ala Val Ser Ala Glu Pro Gly Leu Ala
    210                 215                 220

Glu Arg Ile Ala Asp Asp Pro Ala Ala Gln Arg Thr Val Ala Glu
225                 230                 235                 240

Val Leu Arg Leu His Pro Ala Leu His Leu Glu Arg Arg Thr Ala Thr
                245                 250                 255

Ala Glu Val Arg Leu Gly Glu His Val Ile Gly Glu Gly Glu Glu Val
                260                 265                 270

Val Val Val Ala Ala Ala Asn Arg Asp Pro Glu Val Phe Ala Glu
    275                 280                 285

Pro Asp Arg Leu Asp Val Asp Arg Pro Asp Ala Asp Arg Ala Leu Ser
    290                 295                 300

Ala His Arg Gly His Pro Gly Arg Leu Glu Glu Leu Val Thr Ala Leu
305                 310                 315                 320

Ala Thr Ala Ala Leu Arg Ala Ala Lys Ala Leu Pro Gly Leu Thr
                325                 330                 335

Pro Ser Gly Pro Val Val Arg Arg Arg Ser Pro Val Leu Arg Gly
                340                 345                 350

Thr Asn Arg Cys Pro Val Glu Leu Met Arg Val Val Phe Ser Ser Met
                355                 360                 365

Ala Ser Lys Ser His Leu Phe Gly Leu Val Pro Leu Ala Trp Ala Phe
    370                 375                 380

Arg Ala Ala Gly His Glu Val Arg Val Val Ala Ser Pro Ala Leu Thr
385                 390                 395                 400

Glu Asp Ile Thr Ala Ala Gly Leu Thr Ala Val Pro Val Gly Thr Asp
                405                 410                 415

Val Asp Leu Val Asp Phe Met Thr His Ala Gly His Asp Ile Ile Asp
```

-continued

```
                420                 425                 430
Tyr Val Arg Ser Leu Asp Phe Ser Glu Arg Asp Pro Ala Thr Leu Thr
            435                 440                 445
Trp Glu His Leu Arg Gly Met Gln Thr Val Leu Thr Pro Thr Phe Tyr
450                 455                 460
Ala Leu Met Ser Pro Asp Thr Leu Ile Glu Gly Met Val Ser Phe Cys
465                 470                 475                 480
Arg Lys Trp Arg Pro Asp Leu Val Ile Trp Glu Pro Leu Thr Phe Ala
                485                 490                 495
Ala Pro Ile Ala Gly Ala Val Thr Gly Thr Pro His Ala Arg Leu Leu
                500                 505                 510
Trp Gly Pro Asp Ile Thr Thr Arg Ala Arg Gln Asn Phe Leu Gly Leu
            515                 520                 525
Leu Pro Asp Gln Pro Glu Glu His Arg Glu Gly Pro Leu Ala Glu Trp
530                 535                 540
Leu Thr Trp Thr Leu Glu Lys Tyr Gly Gly Pro Ala Phe Asp Glu Glu
545                 550                 555                 560
Val Val Val Gly Gln Trp Thr Ile Asp Pro Ala Pro Ala Ala Ile Arg
                565                 570                 575
Leu Asp Thr Gly Leu Lys Thr Val Gly Met Arg Tyr Val Asp Tyr Asn
                580                 585                 590
Gly Pro Ser Val Val Pro Glu Trp Leu His Asp Glu Pro Glu Arg Arg
            595                 600                 605
Arg Val Cys Leu Thr Leu Gly Ile Ser Ser Arg Glu Asn Ser Ile Gly
            610                 615                 620
Gln Val Ser Ile Glu Glu Leu Leu Gly Ala Val Gly Asp Val Asp Ala
625                 630                 635                 640
Glu Ile Ile Ala Thr Phe Asp Ala Gln Gln Leu Glu Gly Val Ala Asn
                645                 650                 655
Ile Pro His Asn Val Arg Thr Val Gly Phe Val Pro Met His Ala Leu
                660                 665                 670
Leu Pro Thr Cys Ala Ala Thr Val His His Gly Gly Pro Gly Ser Trp
            675                 680                 685
His Thr Ala Ala Ile His Gly Val Pro Gln Val Ile Leu Pro Asp Gly
            690                 695                 700
Trp Asp Thr Gly Val Arg Ala Gln Arg Thr Gln Glu Phe Gly Ala Gly
705                 710                 715                 720
Ile Ala Leu Pro Val Pro Glu Leu Thr Pro Asp Gln Leu Arg Glu Ser
                725                 730                 735
Val Lys Arg Val Leu Asp Asp Pro Ala His Arg Ala Gly Ala Ala Arg
            740                 745                 750
Met Arg Asp Asp Met Leu Ala Glu Pro Ser Pro Ala Glu Val Val Gly
            755                 760                 765
Ile Cys Glu Glu Leu Ala Ala Gly Arg Arg Glu Pro Arg Met Thr Thr
            770                 775                 780
Asp Ala Ala Thr His Val Arg Leu Gly Arg Ser Ala Leu Leu Thr Ser
785                 790                 795                 800
Arg Leu Trp Leu Gly Thr Val Asn Phe Ser Gly Arg Val Glu Asp Asp
                805                 810                 815
Asp Ala Leu Arg Leu Met Asp His Ala Arg Asp Arg Gly Ile Asn Cys
            820                 825                 830
Leu Asp Thr Ala Asp Met Tyr Gly Trp Arg Leu Tyr Lys Gly His Thr
            835                 840                 845
```

-continued

```
Glu Glu Leu Val Gly Arg Trp Leu Ala Gln Gly Gly Gly Arg Arg Glu
            850                 855                 860

Asp Thr Val Leu Ala Thr Lys Val Gly Gly Glu Met Ser Glu Arg Val
865                 870                 875                 880

Asn Asp Ser Gly Leu Ser Ala Arg His Ile Ile Ala Ser Cys Glu Gly
                885                 890                 895

Ser Leu Arg Arg Leu Gly Val Asp His Ile Asp Val Tyr Gln Met His
                900                 905                 910

His Ile Asp Arg Ser Ala Pro Trp Asp Glu Val Trp Gln Ala Met Asp
            915                 920                 925

Ser Leu Val Ala Ser Gly Lys Val Ser Tyr Val Gly Ser Ser Asn Phe
        930                 935                 940

Ala Gly Trp His Ile Ala Ala Ala Gln Glu Asn Ala Ala Arg Arg His
945                 950                 955                 960

Ser Leu Gly Met Val Ser His Gln Cys Leu Tyr Asn Leu Ala Val Arg
                965                 970                 975

His Ala Glu Leu Glu Val Leu Pro Ala Ala Gln Ala Tyr Gly Leu Gly
            980                 985                 990

Val Phe Ala Trp Ser Pro Leu His Gly Gly Leu Leu Ser Gly Ala Leu
        995                 1000                1005

Glu Lys Leu Ala Ala Gly Thr Ala Val Lys Ser Ala Gln Gly Arg Ala
1010                1015                1020

Gln Val Leu Leu Pro Ser Leu Arg Pro Ala Ile Glu Ala Tyr Glu Lys
025                 1030                1035                1040

Phe Cys Arg Asn Leu Gly Glu Asp Pro Ala Glu Val Gly Leu Ala Trp
                1045                1050                1055

Val Leu Ser Arg Pro Gly Ile Ala Gly Ala Val Ile Gly Pro Arg Thr
            1060                1065                1070

Pro Glu Gln Leu Asp Ser Ala Leu Lys Ala Ser Ala Met Thr Leu Asp
        1075                1080                1085

Glu Gln Ala Leu Ser Glu Leu Asp Glu Ile Phe Pro Ala Val Ala Ser
    1090                1095                1100

Gly Gly Ala Ala Pro Glu Ala Trp Leu Gln
105                 1110
```

(2) INFORMATION FOR SEQ ID NO:32:

(i) SEQUENCE CHARACTERISTICS:
        (A) LENGTH: 2544 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

```
Met Asn Gly Ile Ser Asp Ser Pro Arg Gln Leu Ile Thr Leu Leu Gly
1               5                   10                  15

Ala Ser Gly Phe Val Gly Ser Ala Val Leu Arg Glu Leu Arg Asp His
                20                  25                  30

Pro Val Arg Leu Arg Ala Val Ser Arg Gly Ala Pro Ala Val Pro
            35                  40                  45

Pro Gly Ala Ala Glu Val Glu Asp Leu Arg Ala Asp Leu Leu Glu Pro
        50                  55                  60

Gly Arg Ala Ala Ala Ala Ile Glu Asp Ala Asp Val Ile Val His Leu
65                  70                  75                  80

Val Ala His Ala Ala Gly Gly Ser Thr Trp Arg Ser Ala Thr Ser Asp
```

-continued

```
                    85                  90                  95
Pro Glu Ala Glu Arg Val Asn Val Gly Leu Met His Asp Leu Val Gly
                100                 105                 110
Ala Leu His Asp Arg Arg Ser Thr Pro Val Leu Leu Tyr Ala
        115                 120                 125
Ser Thr Ala Gln Ala Ala Asn Pro Ser Ala Ala Ser Arg Tyr Ala Gln
    130                 135                 140
Gln Lys Thr Glu Ala Glu Arg Ile Leu Arg Lys Ala Thr Asp Glu Gly
145                 150                 155                 160
Arg Val Arg Gly Val Ile Leu Arg Leu Pro Ala Val Tyr Gly Gln Ser
                165                 170                 175
Gly Pro Ser Gly Pro Met Gly Arg Gly Val Val Ala Ala Met Ile Arg
            180                 185                 190
Arg Ala Leu Ala Gly Glu Pro Leu Thr Met Trp His Asp Gly Gly Val
        195                 200                 205
Arg Arg Asp Leu Leu His Val Glu Asp Val Ala Thr Ala Phe Ala Ala
    210                 215                 220
Ala Leu Glu His His Asp Ala Leu Ala Gly Gly Thr Trp Ala Leu Gly
225                 230                 235                 240
Ala Asp Arg Ser Glu Pro Leu Gly Asp Ile Phe Arg Ala Val Ser Gly
                245                 250                 255
Ser Val Ala Arg Gln Thr Gly Ser Pro Ala Val Asp Val Val Thr Val
            260                 265                 270
Pro Ala Pro Glu His Ala Glu Ala Asn Asp Phe Arg Ser Asp Asp Ile
        275                 280                 285
Asp Ser Thr Glu Phe Arg Ser Arg Thr Gly Trp Arg Pro Arg Val Ser
    290                 295                 300
Leu Thr Asp Gly Ile Asp Arg Thr Val Ala Ala Leu Thr Pro Thr Glu
305                 310                 315                 320
Glu His Met Arg Val Leu Leu Thr Ser Phe Ala His Arg Thr His Phe
                325                 330                 335
Gln Gly Leu Val Pro Leu Ala Trp Ala Leu Arg Thr Ala Gly His Asp
            340                 345                 350
Val Arg Val Ala Ala Gln Pro Ala Leu Thr Asp Ala Val Ile Gly Ala
        355                 360                 365
Gly Leu Thr Ala Val Pro Val Gly Ser Asp His Arg Leu Phe Asp Ile
    370                 375                 380
Val Pro Glu Val Ala Ala Gln Val His Arg Tyr Ser Phe Tyr Leu Asp
385                 390                 395                 400
Phe Tyr His Arg Glu Gln Glu Leu His Ser Trp Glu Phe Leu Leu Gly
                405                 410                 415
Met Gln Glu Ala Thr Ser Arg Trp Val Tyr Pro Val Val Asn Asn Asp
            420                 425                 430
Ser Phe Val Ala Glu Leu Val Asp Phe Ala Arg Asp Trp Arg Pro Asp
        435                 440                 445
Leu Val Leu Trp Glu Pro Phe Thr Phe Ala Gly Ala Val Ala Ala Arg
    450                 455                 460
Ala Cys Gly Ala Ala His Ala Arg Leu Leu Trp Gly Ser Asp Leu Thr
465                 470                 475                 480
Gly Tyr Phe Arg Gly Arg Phe Gln Ala Gln Arg Leu Arg Arg Pro Pro
                485                 490                 495
Glu Asp Arg Pro Asp Pro Leu Gly Thr Trp Leu Thr Glu Val Ala Gly
            500                 505                 510
```

```
Arg Phe Gly Val Glu Phe Gly Glu Asp Leu Ala Val Gly Gln Trp Ser
        515                 520                 525

Val Asp Gln Leu Pro Pro Ser Phe Arg Leu Asp Thr Gly Met Glu Thr
    530                 535                 540

Val Val Ala Arg Thr Leu Pro Tyr Asn Gly Ala Ser Val Val Pro Asp
545                 550                 555                 560

Trp Leu Lys Lys Gly Ser Ala Thr Arg Arg Ile Cys Ile Thr Gly Gly
            565                 570                 575

Phe Ser Gly Leu Gly Leu Ala Ala Asp Ala Asp Gln Phe Ala Arg Thr
            580                 585                 590

Leu Ala Gln Leu Ala Arg Phe Asp Gly Glu Ile Val Val Thr Gly Ser
        595                 600                 605

Gly Pro Asp Thr Ser Ala Val Pro Asp Asn Ile Arg Leu Val Asp Phe
        610                 615                 620

Val Pro Met Gly Val Leu Leu Gln Asn Cys Ala Ala Ile Ile His His
625                 630                 635                 640

Gly Gly Ala Gly Thr Trp Ala Thr Ala Leu His His Gly Ile Pro Gln
                645                 650                 655

Ile Ser Val Ala His Glu Trp Asp Cys Met Leu Arg Gly Gln Gln Thr
            660                 665                 670

Ala Glu Leu Gly Ala Gly Ile Tyr Leu Arg Pro Asp Glu Val Asp Ala
        675                 680                 685

Asp Ser Leu Ala Ser Ala Leu Thr Gln Val Val Glu Asp Pro Thr Tyr
        690                 695                 700

Thr Glu Asn Ala Val Lys Leu Arg Glu Glu Ala Leu Ser Asp Pro Thr
705                 710                 715                 720

Pro Gln Glu Ile Val Pro Arg Leu Glu Leu Thr Arg Arg His Ala
            725                 730                 735

Gly Met Tyr Glu Gly Gly Phe Ala Glu Leu Tyr Asp Arg Phe Tyr Arg
            740                 745                 750

Gly Arg Gly Lys Asp Tyr Ala Ala Glu Ala Ala Gln Val Ala Arg Leu
        755                 760                 765

Val Arg Asp Arg Leu Pro Ser Ala Ser Ser Leu Leu Asp Val Ala Cys
770                 775                 780

Gly Thr Gly Thr His Leu Arg Arg Phe Ala Asp Leu Phe Asp Asp Val
785                 790                 795                 800

Thr Gly Leu Glu Leu Ser Ala Ala Met Ile Glu Val Ala Arg Pro Gln
                805                 810                 815

Leu Gly Gly Ile Pro Val Leu Gln Gly Asp Met Arg Asp Phe Ala Leu
            820                 825                 830

Asp Arg Glu Phe Asp Ala Val Thr Cys Met Phe Ser Ser Ile Gly His
        835                 840                 845

Met Arg Asp Gly Ala Glu Leu Asp Gln Ala Leu Ala Ser Phe Ala Arg
850                 855                 860

His Leu Ala Pro Gly Gly Val Val Val Glu Pro Trp Trp Phe Pro
865                 870                 875                 880

Glu Asp Phe Leu Asp Gly Tyr Val Ala Gly Asp Val Val Arg Asp Gly
                885                 890                 895

Asp Leu Thr Ile Ser Arg Val Ser His Ser Val Arg Ala Gly Gly Ala
            900                 905                 910

Thr Arg Met Glu Ile His Trp Val Val Ala Asp Ala Val Asn Gly Pro
        915                 920                 925

Arg His His Val Glu His Tyr Glu Ile Thr Leu Phe Glu Arg Gln Gln
        930                 935                 940
```

```
Tyr Glu Lys Ala Phe Thr Ala Ala Gly Cys Ala Val Gln Tyr Leu Glu
945                 950                 955                 960

Gly Gly Pro Ser Gly Arg Gly Leu Phe Val Gly Val Arg Gly Met Gly
                965                 970                 975

Asp Arg Thr Gly Asp Arg Thr Ile Pro Glu Ser Ser Gln Thr Ala Thr
            980                 985                 990

Arg Phe Leu Leu Gly Asp Gly Gly Ile Pro Thr Ala Thr Ala Glu Thr
            995                 1000                1005

His Asp Trp Leu Thr Arg Asn Gly Ala Glu Gln Arg Leu Glu Val Ala
    1010                1015                1020

Arg Val Pro Phe Ser Ala Met Asp Arg Trp Ser Phe Gln Pro Glu Asp
    025                 1030                1035                1040

Gly Arg Leu Ala His Glu Ser Gly Arg Phe Phe Ser Ile Glu Gly Leu
                1045                1050                1055

His Val Arg Thr Asn Phe Gly Trp Arg Arg Asp Trp Ile Gln Pro Ile
        1060                1065                1070

Ile Val Gln Pro Glu Ile Gly Phe Leu Gly Leu Ile Val Lys Glu Phe
        1075                1080                1085

Asp Gly Val Leu His Val Leu Ala Gln Ala Lys Ala Glu Pro Gly Asn
        1090                1095                1100

Ile Asn Ala Val Gln Leu Ser Pro Thr Leu Gln Ala Thr Arg Ser Asn
105                 1110                1115                1120

Tyr Thr Gly Val His Arg Gly Ser Lys Val Arg Phe Ile Glu Tyr Phe
                1125                1130                1135

Asn Gly Thr Arg Pro Ser Arg Ile Leu Val Asp Val Leu Gln Ser Glu
            1140                1145                1150

Gln Gly Ala Trp Phe Leu Arg Lys Arg Asn Arg Asn Met Val Val Glu
            1155                1160                1165

Val Phe Asp Asp Leu Pro Glu His Pro Asn Phe Arg Trp Leu Thr Val
    1170                1175                1180

Ala Gln Leu Arg Ala Met Leu His His Asp Asn Val Val Asn Met Asp
185                 1190                1195                1200

Leu Arg Thr Val Leu Ala Cys Val Pro Thr Ala Val Glu Arg Asp Arg
            1205                1210                1215

Ala Asp Asp Val Leu Ala Arg Leu Pro Glu Gly Ser Phe Gln Ala Arg
            1220                1225                1230

Leu Leu His Ser Phe Ile Gly Ala Gly Thr Pro Ala Asn Asn Met Asn
        1235                1240                1245

Ser Leu Leu Ser Trp Ile Ser Asp Val Arg Ala Arg Arg Glu Phe Val
        1250                1255                1260

Gln Arg Gly Arg Pro Leu Pro Asp Ile Glu Arg Ser Gly Trp Ile Arg
265                 1270                1275                1280

Arg Asp Asp Gly Ile Glu His Glu Glu Lys Lys Tyr Phe Asp Val Phe
            1285                1290                1295

Gly Val Thr Val Ala Thr Ser Asp Arg Glu Val Asn Ser Trp Met Gln
            1300                1305                1310

Pro Leu Leu Ser Pro Ala Asn Asn Gly Leu Leu Ala Leu Leu Val Lys
    1315                1320                1325

Asp Ile Gly Gly Thr Leu His Ala Leu Val Gln Leu Arg Thr Glu Ala
    1330                1335                1340

Gly Gly Met Asp Val Ala Glu Leu Ala Pro Thr Val His Cys Gln Pro
345                 1350                1355                1360

Asp Asn Tyr Ala Asp Ala Pro Glu Glu Phe Arg Pro Ala Tyr Val Asp
```

```
                        1365              1370              1375
Tyr Val Leu Asn Val Pro Arg Ser Gln Val Arg Tyr Asp Ala Trp His
            1380              1385              1390
Ser Glu Glu Gly Gly Arg Phe Tyr Arg Asn Glu Asn Arg Tyr Met Leu
            1395              1400              1405
Ile Glu Val Pro Ala Asp Phe Asp Ala Ser Ala Ala Pro Asp His Arg
            1410              1415              1420
Trp Met Thr Phe Asp Gln Ile Thr Tyr Leu Leu Gly His Ser His Tyr
425              1430              1435              1440
Val Asn Ile His Val Arg Ser Ile Ile Ala Cys Ala Ser Ala Val Tyr
            1445              1450              1455
Thr Arg Thr Ala Gly Met Lys Arg Ala Leu Thr Asp Leu Ala Ile Phe
            1460              1465              1470
Gly Gly Pro Glu Ala Phe Leu His Thr Leu Tyr Val Gly Arg Pro Thr
            1475              1480              1485
Val Gly Asp Arg Glu Arg Phe Phe Ala Arg Leu Glu Trp Ala Leu Asn
            1490              1495              1500
Asn Asn Trp Leu Thr Asn Gly Gly Pro Leu Val Arg Glu Phe Glu Gly
505              1510              1515              1520
Arg Val Ala Asp Leu Ala Gly Val Arg His Cys Val Ala Thr Cys Asn
            1525              1530              1535
Ala Thr Val Ala Leu Gln Leu Val Leu Arg Ala Ser Asp Val Ser Gly
            1540              1545              1550
Glu Val Val Met Pro Ser Met Thr Phe Ala Ala Thr Ala His Ala Ala
            1555              1560              1565
Ser Trp Leu Gly Leu Glu Pro Val Phe Cys Asp Val Asp Pro Glu Thr
            1570              1575              1580
Gly Leu Leu Asp Pro Glu His Val Ala Ser Leu Val Thr Pro Arg Thr
585              1590              1595              1600
Gly Ala Ile Ile Gly Val His Leu Trp Gly Arg Pro Ala Pro Val Glu
            1605              1610              1615
Ala Leu Glu Lys Ile Ala Ala Glu His Gln Val Lys Leu Phe Phe Asp
            1620              1625              1630
Ala Ala His Ala Leu Gly Cys Thr Ala Gly Gly Arg Pro Val Gly Ala
            1635              1640              1645
Phe Gly Asn Ala Glu Val Phe Ser Phe His Ala Thr Lys Ala Val Thr
            1650              1655              1660
Ser Phe Glu Gly Gly Ala Ile Val Thr Asp Asp Gly Leu Leu Ala Asp
665              1670              1675              1680
Arg Ile Arg Ala Met His Asn Phe Gly Ile Ala Pro Asp Lys Leu Val
            1685              1690              1695
Thr Asp Val Gly Thr Asn Gly Lys Met Ser Glu Cys Ala Ala Ala Met
            1700              1705              1710
Gly Leu Thr Ser Leu Asp Ala Phe Ala Glu Thr Arg Val His Asn Arg
            1715              1720              1725
Leu Asn His Ala Leu Tyr Ser Asp Glu Leu Arg Asp Val Arg Gly Ile
            1730              1735              1740
Ser Val His Ala Phe Asp Pro Gly Glu Gln Asn Asn Tyr Gln Tyr Val
745              1750              1755              1760
Ile Ile Ser Val Asp Ser Ala Ala Thr Gly Ile Asp Arg Asp Gln Leu
            1765              1770              1775
Gln Ala Ile Leu Arg Ala Glu Lys Val Val Ala Gln Pro Tyr Phe Ser
            1780              1785              1790
```

-continued

Pro Gly Cys His Gln Met Gln Pro Tyr Arg Thr Glu Pro Pro Leu Arg
1795                 1800                1805

Leu Glu Asn Thr Glu Gln Leu Ser Asp Arg Val Leu Ala Leu Pro Thr
    1810                1815                1820

Gly Pro Ala Val Ser Ser Glu Asp Ile Arg Arg Val Cys Asp Ile Ile
825             1830                1835                1840

Arg Leu Ala Ala Thr Ser Gly Glu Leu Ile Asn Ala Gln Trp Asp Gln
            1845                1850                1855

Arg Thr Arg Asn Gly Ser Met Asn Thr Thr Arg Thr Ala Thr Ala Gln
                1860                1865                1870

Glu Ala Gly Val Ala Asp Ala Ala Arg Pro Asp Val Asp Arg Arg Ala
    1875                1880                1885

Val Val Arg Ala Leu Ser Ser Glu Val Ser Arg Val Thr Gly Ala Gly
        1890                1895                1900

Asp Gly Asp Ala His Val Gln Ala Ala Arg Leu Ala Asp Leu Ala Ala
905             1910                1915                1920

His Tyr Gly Ala His Pro Phe Thr Pro Leu Glu Gln Thr Arg Ala Arg
            1925                1930                1935

Leu Gly Leu Asp Arg Ala Glu Phe Ala His Leu Leu Asp Leu Phe Gly
                1940                1945                1950

Arg Ile Pro Asp Leu Gly Thr Ala Val Glu His Gly Pro Ala Gly Lys
    1955                1960                1965

Tyr Trp Ser Asn Thr Ile Lys Pro Leu Asp Ala Ala Gly Ala Leu Asp
        1970                1975                1980

Ala Ala Val Tyr Arg Lys Pro Ala Phe Pro Tyr Ser Val Gly Leu Tyr
985             1990                1995                2000

Pro Gly Pro Thr Cys Met Phe Arg Cys His Phe Cys Val Arg Val Thr
            2005                2010                2015

Gly Ala Arg Tyr Glu Ala Ala Ser Val Pro Ala Gly Asn Glu Thr Leu
                2020                2025                2030

Ala Ala Ile Ile Asp Glu Val Pro Thr Asp Asn Pro Lys Ala Met Tyr
    2035                2040                2045

Met Ser Gly Gly Leu Glu Pro Leu Thr Asn Pro Gly Leu Gly Glu Leu
    2050                2055                2060

Val Ser His Ala Ala Gly Arg Gly Phe Asp Leu Thr Val Tyr Thr Asn
065             2070                2075                2080

Ala Phe Ala Leu Thr Glu Gln Thr Leu Asn Arg Gln Pro Gly Leu Trp
            2085                2090                2095

Glu Leu Gly Ala Ile Arg Thr Ser Leu Tyr Gly Leu Asn Asn Asp Glu
                2100                2105                2110

Tyr Glu Thr Thr Thr Gly Lys Arg Gly Ala Phe Glu Arg Val Lys Lys
    2115                2120                2125

Asn Leu Gln Gly Phe Leu Arg Met Arg Ala Glu Arg Asp Ala Pro Ile
    2130                2135                2140

Arg Leu Gly Phe Asn His Ile Ile Leu Pro Gly Arg Ala Asp Arg Leu
145             2150                2155                2160

Thr Asp Leu Val Asp Phe Ile Ala Glu Leu Asn Glu Ser Ser Pro Gln
            2165                2170                2175

Arg Pro Leu Asp Phe Val Thr Val Arg Glu Asp Tyr Ser Gly Arg Asp
                2180                2185                2190

Asp Gly Arg Leu Ser Asp Ser Glu Arg Asn Glu Leu Arg Glu Gly Leu
    2195                2200                2205

Val Arg Phe Val Asp Tyr Ala Ala Glu Arg Thr Pro Gly Met His Ile
    2210                2215                2220

Asp Leu Gly Tyr Ala Leu Glu Ser Leu Arg Arg Gly Val Asp Ala Glu
225                 2230                2235                2240

Leu Leu Arg Ile Arg Pro Glu Thr Met Arg Pro Thr Ala His Pro Gln
                2245                2250                2255

Val Ala Val Gln Ile Asp Leu Leu Gly Asp Val Tyr Leu Tyr Arg Glu
                2260                2265                2270

Ala Gly Phe Pro Glu Leu Glu Gly Ala Thr Arg Tyr Ile Ala Gly Arg
            2275                2280                2285

Val Thr Pro Ser Thr Ser Leu Arg Glu Val Val Glu Asn Phe Val Leu
            2290                2295                2300

Glu Asn Glu Gly Val Gln Pro Arg Pro Gly Asp Glu Tyr Phe Leu Asp
305             2310                2315                2320

Gly Phe Asp Gln Ser Val Thr Ala Arg Leu Asn Gln Leu Glu Arg Asp
            2325                2330                2335

Ile Ala Asp Gly Trp Glu Asp His Arg Gly Phe Leu Arg Gly Arg Met
            2340                2345                2350

Ala Gly Gly Phe Glu Phe Thr Pro Asp Pro Lys Gln Asp Arg Arg Gly
            2355                2360                2365

Leu Phe Val Ser Pro Leu Gln Asp Glu Ala Phe Val Gly Ala Val Gly
            2370                2375                2380

His Arg Phe Pro Val Ala Gln Met Asn His Ile Val Ser Ala Arg Gly
385             2390                2395                2400

Val Leu Arg Gly Leu His Phe Thr Thr Thr Pro Pro Gly Gln Cys Lys
                2405                2410                2415

Tyr Val Tyr Cys Ala Arg Gly Arg Ala Leu Asp Val Ile Val Asp Ile
                2420                2425                2430

Arg Val Gly Ser Pro Thr Phe Gly Lys Trp Asp Ala Val Glu Met Asp
            2435                2440                2445

Thr Glu His Phe Arg Ala Val Tyr Phe Pro Arg Gly Thr Ala His Ala
            2450                2455                2460

Phe Leu Ala Leu Glu Asp Asp Thr Leu Met Ser Tyr Leu Val Ser Thr
465             2470                2475                2480

Pro Tyr Val Ala Glu Tyr Glu Gln Ala Ile Asp Pro Phe Asp Pro Ala
                2485                2490                2495

Leu Gly Leu Pro Trp Pro Ala Asp Leu Glu Val Val Leu Ser Asp Arg
            2500                2505                2510

Asp Thr Val Ala Val Asp Leu Glu Thr Ala Arg Arg Arg Gly Met Leu
            2515                2520                2525

Pro Asp Tyr Ala Asp Cys Leu Gly Glu Glu Pro Ala Ser Thr Gly Arg
    2530                2535                2540

(2) INFORMATION FOR SEQ ID NO:33:

(i) SEQUENCE CHARACTERISTICS:
        (A) LENGTH: 322 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:33:

Val Asn Gly Ile Ser Asp Ser Pro Arg Gln Leu Ile Thr Leu Leu Gly
1               5                   10                  15

Ala Ser Gly Phe Val Gly Ser Ala Val Leu Arg Glu Leu Arg Asp His
                20                  25                  30

```
Pro Val Arg Leu Arg Ala Val Ser Arg Gly Ala Pro Ala Val Pro
        35                  40                  45

Pro Gly Ala Ala Glu Val Glu Asp Leu Arg Ala Asp Leu Leu Glu Pro
    50                  55                  60

Gly Arg Ala Ala Ala Ile Glu Asp Ala Asp Val Ile Val His Leu
65                  70                  75                  80

Val Ala His Ala Ala Gly Gly Ser Thr Trp Arg Ser Ala Thr Ser Asp
                85                  90                  95

Pro Glu Ala Glu Arg Val Asn Val Gly Leu Met His Asp Leu Val Gly
                100                 105                 110

Ala Leu His Asp Arg Arg Arg Ser Thr Pro Val Leu Leu Tyr Ala
            115                 120                 125

Ser Thr Ala Gln Ala Ala Asn Pro Ser Ala Ala Ser Arg Tyr Ala Gln
    130                 135                 140

Gln Lys Thr Glu Ala Glu Arg Ile Leu Arg Lys Ala Thr Asp Glu Gly
145                 150                 155                 160

Arg Val Arg Gly Val Ile Leu Arg Leu Pro Ala Val Tyr Gly Gln Ser
                165                 170                 175

Gly Pro Ser Gly Pro Met Gly Arg Gly Val Val Ala Ala Met Ile Arg
            180                 185                 190

Arg Ala Leu Ala Gly Glu Pro Leu Thr Met Trp His Asp Gly Gly Val
            195                 200                 205

Arg Arg Asp Leu Leu His Val Glu Asp Val Ala Thr Ala Phe Ala Ala
210                 215                 220

Ala Leu Glu His His Asp Ala Leu Ala Gly Gly Thr Trp Ala Leu Gly
225                 230                 235                 240

Ala Asp Arg Ser Glu Pro Leu Gly Asp Ile Phe Arg Ala Val Ser Gly
                245                 250                 255

Ser Val Ala Arg Gln Thr Gly Ser Pro Ala Val Asp Val Val Thr Val
            260                 265                 270

Pro Ala Pro Glu His Ala Glu Ala Asn Asp Phe Arg Ser Asp Asp Ile
        275                 280                 285

Asp Ser Thr Glu Phe Arg Ser Arg Thr Gly Trp Arg Pro Arg Val Ser
    290                 295                 300

Leu Thr Asp Gly Ile Asp Arg Thr Val Ala Ala Leu Thr Pro Thr Glu
305                 310                 315                 320

Glu His (2) INFORMATION FOR SEQ ID NO:34:

(i) SEQUENCE CHARACTERISTICS:
        (A) LENGTH: 290 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:34:

Met Lys Leu Leu Ile Thr Gly Val Ser Gly Tyr Ile Gly Ser His Leu
1               5                   10                  15

Val Asn Tyr Leu Ala Asn Leu Gly Gly Tyr Glu Ile Tyr Gly Ile Ser
            20                  25                  30

Arg Asn Glu Ile Leu Asp Gln Asp Ile Asn Gln Leu Leu Leu Asn Ile
        35                  40                  45

Lys Ile Phe Gln Leu Asp Arg Asp Ser Leu Pro Asp Ile Leu Lys Arg
    50                  55                  60
```

```
Val Arg Pro Asp Val Val Ile His Leu Ala Ser Cys Phe Leu Ser Gln
 65              70                  75                  80

His Ser Tyr Lys Asn Ile Lys Glu Ile Ile Lys Ser Asn Val Glu Phe
                 85                  90                  95

Pro Thr Glu Leu Leu Glu Ala Met Asn Asp Val Gly Val Lys Lys Ile
            100                 105                 110

Ile Asn Thr Gly Thr Ser Trp Gln Cys Phe Asn Ser Asp Thr Tyr Asn
            115                 120                 125

Pro Val Asn Leu Tyr Ala Ala Ser Lys Gln Ala Phe Glu Asp Ile Leu
        130                 135                 140

Lys Phe Tyr Ile Asn Ala Glu Gly Phe Ser Ala Ile Asn Leu Lys Leu
145             150                 155                 160

Phe Asp Thr Tyr Gly Gly Val Asp Lys Arg Arg Lys Leu Ile Ser Leu
                165                 170                 175

Leu Asp Asp Ile Ala Lys Asn Asn Lys Gln Leu Asp Met Ser Pro Gly
            180                 185                 190

Glu Gln Leu Leu Asp Leu Val His Ile Asn Asp Val Cys Arg Ala Phe
        195                 200                 205

Lys Ile Ala Ile Asp Lys Leu Cys Glu Leu Pro Ser Glu Tyr Val Val
210             215                 220

Ser Tyr Gly Val Ser Asn Lys Tyr Arg Val Thr Leu Lys Glu Leu Val
225             230                 235                 240

Ser Ile Tyr Glu Arg Val Asn Asn Val Lys Leu Asn Ile Asn Phe Gly
                245                 250                 255

Thr Arg Glu Tyr Arg Asn Arg Glu Val Met Val Pro Cys Thr Asn Ile
            260                 265                 270

Gln Asn Leu Pro Asp Trp Glu Val Val Ile Pro Leu Ser Gln Gly Leu
            275                 280                 285

Lys Tyr
    290

(2) INFORMATION FOR SEQ ID NO:35:

(i) SEQUENCE CHARACTERISTICS:
        (A) LENGTH: 299 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:35:

Met Thr Phe Leu Lys Glu Tyr Val Ile Val Ser Gly Ala Ser Gly Phe
 1               5                  10                  15

Ile Gly Lys His Leu Leu Glu Ala Leu Lys Lys Ser Gly Ile Ser Val
                 20                  25                  30

Val Ala Ile Thr Arg Asp Val Ile Lys Asn Asn Ser Asn Ala Leu Ala
             35                  40                  45

Asn Val Arg Trp Cys Ser Trp Asp Asn Ile Glu Leu Leu Val Glu Glu
         50                  55                  60

Leu Ser Ile Asp Ser Ala Leu Ile Gly Ile His Leu Ala Thr Glu
 65              70                  75                  80

Tyr Gly His Lys Thr Ser Ser Leu Ile Asn Ile Glu Asp Ala Asn Val
                 85                  90                  95

Ile Lys Pro Leu Lys Leu Leu Asp Leu Ala Ile Lys Tyr Arg Ala Asp
            100                 105                 110
```

```
Ile Phe Leu Asn Thr Asp Ser Phe Ala Lys Lys Asp Phe Asn Tyr
        115                 120                 125

Gln His Met Arg Pro Tyr Ile Ile Thr Lys Arg His Phe Asp Glu Ile
    130                 135                 140

Gly His Tyr Tyr Ala Asn Met His Asp Ile Ser Phe Val Asn Met Arg
145                 150                 155                 160

Leu Glu His Val Tyr Gly Pro Gly Asp Gly Glu Asn Lys Phe Ile Pro
                165                 170                 175

Tyr Ile Ile Asp Cys Leu Asn Lys Lys Gln Ser Cys Val Lys Cys Thr
                180                 185                 190

Thr Gly Glu Gln Ile Arg Asp Phe Ile Phe Val Asp Asp Val Val Asn
            195                 200                 205

Ala Tyr Leu Thr Ile Leu Glu Asn Arg Lys Glu Val Pro Ser Tyr Thr
    210                 215                 220

Glu Tyr Gln Val Gly Thr Gly Ala Gly Val Ser Leu Lys Asp Phe Leu
225                 230                 235                 240

Val Tyr Leu Gln Asn Thr Met Met Pro Gly Ser Ser Ser Ile Phe Glu
                245                 250                 255

Phe Gly Ala Ile Glu Gln Arg Asp Asn Glu Ile Met Phe Ser Val Ala
                260                 265                 270

Asn Asn Lys Asn Leu Lys Ala Met Gly Trp Lys Pro Asn Phe Asp Tyr
            275                 280                 285

Lys Lys Gly Ile Glu Glu Leu Leu Lys Arg Leu
            290                 295

(2) INFORMATION FOR SEQ ID NO:36:

(i) SEQUENCE CHARACTERISTICS:
        (A) LENGTH: 308 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:36:

Met Ser Pro Tyr Pro Arg Pro Arg Trp Leu Val Thr Gly Ala Ser Gly
  1                 5                  10                  15

Met Leu Gly Arg Glu Leu Thr Pro Leu Leu Asp Arg Arg Gly Ala Ala
                20                  25                  30

Val Thr Ala Leu Gly Arg Gly His Leu Asp Ile Thr Asp Gly Ala Ala
            35                  40                  45

Val Arg Ser Ala Val Ala Glu His Arg Pro Ala Val Val Asn Cys
        50                  55                  60

Ala Ala Trp Thr Ala Val Asp Glu Ala Glu Ser Glu Pro Ala Leu Ala
 65                 70                  75                  80

Met Ala Val Asn Gly Glu Gly Pro Arg His Leu Ala Gln Ala Cys Arg
                85                  90                  95

Ala Val Gly Ala Val Leu Leu Gln Leu Ser Thr Asp Tyr Val Phe Pro
               100                 105                 110

Gly Ser Gly Gly Arg Pro Tyr Arg Glu Asp His Pro Thr Gly Pro Arg
               115                 120                 125

Thr Val Tyr Gly Cys Thr Lys Arg Ala Gly Glu Arg Ala Val Leu Glu
           130                 135                 140

Val Leu Pro Asp Thr Gly Tyr Ile Val Arg Thr Ala Trp Leu Tyr Gly
145                 150                 155                 160

Ala Gly Gly Pro Asn Phe Val Ala Lys Met Ile Arg Leu Glu Ala Asp
```

```
                        165                 170                 175
Glu Asp Thr Val Leu Val Asp Gln His Gly Gln Pro Thr Trp
                    180                 185                 190
Thr Ala Asp Leu Ala Asp Arg Leu Ala Ala Leu Gly Ala Ala Leu
                195                 200                 205
Ala Gly Thr Ala Pro Ala Gly Ile Tyr His Ala Thr Asn Thr Gly Gly
    210                 215                 220
Thr Thr Trp Asn Ala Leu Ala Pro Glu Thr Phe Arg Leu Leu Gly Ala
225                 230                 235                 240
Ser Thr Arg Leu Asp Pro Ala Arg Val Arg Pro Thr Thr Ser Leu Ala
                245                 250                 255
Leu Ala Arg Pro Ala Val Arg Pro Arg Tyr Ser Val Leu Asp Gln Ser
                260                 265                 270
Arg Trp Lys Ala Ala Gly Leu Glu Pro Leu Arg His Trp Arg Ala Ala
                275                 280                 285
Leu Thr Glu Ser Phe Pro Ala Leu Cys Gly Arg Ala Gly Arg Pro Val
    290                 295                 300
Pro Gly Pro Arg
305

(2) INFORMATION FOR SEQ ID NO:37:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:37:

Val Leu Val Thr Gly Gly Ser Gly Tyr Ile Gly Ser His Thr Cys Val
1               5                   10                  15
Gln Leu Leu Gln Asn Gly His Asp Val Ile Ile Leu Asp Asn Leu Cys
                20                  25                  30
Asn Ser Lys Arg Ser Val Leu Pro Val Ile Glu Arg Leu Gly Gly Lys
            35                  40                  45
His Pro Thr Phe Val Glu Gly Asp Ile Arg Asn Glu Ala Leu Met Thr
        50                  55                  60
Glu Ile Leu His Asp His Ala Ile Asp Thr Val Ile His Phe
65                  70                  75

(2) INFORMATION FOR SEQ ID NO:38:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:38:

Val Gly Ser Gly Ile Gly Leu Arg Leu Val Val His Ala Asn Leu Ala
1               5                   10                  15
Leu Leu Thr Tyr Tyr Lys Glu Ile Leu Tyr Gly Val Asp Ala Phe Ala
                20                  25                  30
Glu Tyr Gly Asp Glu Trp Leu Glu
            35                  40
```

(2) INFORMATION FOR SEQ ID NO:39:

(i) SEQUENCE CHARACTERISTICS:
        (A) LENGTH: 193 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:39:

```
Val Ala Gly Gly Phe Glu Phe Thr Pro Asp Pro Lys Gln Asp Arg Arg
 1               5                  10                  15

Gly Leu Phe Val Ser Pro Leu Gln Asp Glu Ala Phe Val Gly Ala Val
            20                  25                  30

Gly His Arg Phe Pro Val Ala Gln Met Asn His Ile Val Ser Ala Arg
        35                  40                  45

Gly Val Leu Arg Gly Leu His Phe Thr Thr Pro Pro Gly Gln Cys
    50                  55                  60

Lys Tyr Val Tyr Cys Ala Arg Gly Arg Ala Leu Asp Val Ile Val Asp
65                  70                  75                  80

Ile Arg Val Gly Ser Pro Thr Phe Gly Lys Trp Asp Ala Val Glu Met
                85                  90                  95

Asp Thr Glu His Phe Arg Ala Val Tyr Phe Pro Arg Gly Thr Ala His
            100                 105                 110

Ala Phe Leu Ala Leu Glu Asp Asp Thr Leu Met Ser Tyr Leu Val Ser
        115                 120                 125

Thr Pro Tyr Val Ala Glu Tyr Glu Gln Ala Ile Asp Pro Phe Asp Pro
    130                 135                 140

Ala Leu Gly Leu Pro Trp Pro Ala Asp Leu Glu Val Val Leu Ser Asp
145                 150                 155                 160

Arg Asp Thr Val Ala Val Asp Leu Glu Thr Ala Arg Arg Arg Gly Met
                165                 170                 175

Leu Pro Asp Tyr Ala Asp Cys Leu Gly Glu Glu Pro Ala Ser Thr Gly
            180                 185                 190

Arg
```

(2) INFORMATION FOR SEQ ID NO:40:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:40:

```
Val Arg Pro Leu Ser Val Gln Gly Ala Trp Leu Ser Glu Thr Arg Ala
 1               5                  10                  15

Phe Ala Asp Asp Arg Gly Glu Phe Gln Glu Leu Tyr Ser Ala Arg Ser
            20                  25                  30

Leu Arg Gly Ala Leu Gly Tyr Asp Pro Gly Val Ala Gln Val Asn Arg
        35                  40                  45

Ser Val Ser Arg Arg Gly Val Leu Arg Gly Val His Phe Ala Gln Leu
    50                  55                  60

Pro Pro Ser Gln Ala Lys Tyr Val Thr Cys Leu Ser Gly Ala Val Leu
65                  70                  75                  80

Asp Val Val Val Asp Ile Arg Thr Gly Ser Pro Thr Tyr Arg Ala Trp
                85                  90                  95
```

Glu Ala Val Arg Leu Asp Asp Pro His Arg Ser Leu Tyr Val Glu Ala
            100                 105                 110

Gly Leu Gly His Ser Phe Met Ala Leu Thr Asp Asp Ala Val Val Val
            115                 120                 125

Tyr Leu Thr Ser Gln Gly Tyr Ala Ala Gly Arg Glu His Gly Val His
            130                 135                 140

Pro Leu Asp Pro Asp Leu Gly Ile Ala Trp Pro Asp Gly Ile Glu Pro
145                 150                 155                 160

Val Leu Ser Glu Lys Asp Arg Gln Ala Pro Gly Ile Ala Glu Met Glu
                165                 170                 175

Arg Arg Gly Leu Leu Pro Asp Tyr Glu Glu Cys Leu Ser Thr Arg Met
                180                 185                 190

Ala Phe Arg Arg Ser Leu Cys Glu Arg Gly Thr Gly
            195                 200

(2) INFORMATION FOR SEQ ID NO:41:

(i) SEQUENCE CHARACTERISTICS:
        (A) LENGTH: 183 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:41:

Val Met Ile Val Ile Lys Thr Ala Ile Pro Asp Val Leu Ile Leu Glu
1               5                   10                  15

Pro Lys Val Phe Gly Asp Glu Arg Gly Phe Phe Glu Ser Tyr Asn
            20                  25                  30

Gln Gln Thr Phe Glu Glu Leu Ile Gly Arg Lys Val Thr Phe Val Gln
            35                  40                  45

Asp Asn His Ser Lys Ser Lys Asn Val Leu Arg Gly Leu His Phe
50                  55                  60

Gln Arg Gly Glu Asn Ala Gln Gly Lys Leu Val Arg Cys Ala Val Gly
65                  70                  75                  80

Glu Val Phe Asp Val Ala Val Asp Ile Arg Lys Glu Ser Pro Thr Phe
                85                  90                  95

Gly Gln Trp Val Gly Val Asn Leu Ser Ala Glu Asn Lys Arg Gln Leu
            100                 105                 110

Trp Ile Pro Glu Gly Phe Ala His Gly Phe Val Thr Leu Ser Glu Tyr
            115                 120                 125

Ala Glu Phe Leu Tyr Lys Ala Thr Asn Tyr Tyr Ser Pro Ser Ser Glu
            130                 135                 140

Gly Ser Ile Leu Trp Asn Asp Glu Ala Ile Gly Ile Glu Trp Pro Phe
145                 150                 155                 160

Ser Gln Leu Pro Glu Leu Ser Ala Lys Asp Ala Ala Pro Leu Leu
                165                 170                 175

Asp Gln Ala Leu Leu Thr Glu
            180

(2) INFORMATION FOR SEQ ID NO:42:

(i) SEQUENCE CHARACTERISTICS:
        (A) LENGTH: 286 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:42:

```
Met Lys Cys Thr Lys Leu Ser Ile Pro Glu Val Ile Leu Phe Glu Pro
 1               5                  10                  15

Arg Ile Phe Glu Asp Asp Arg Gly His Phe Phe Glu Ser Phe Asn Leu
                20                  25                  30

Ala Lys Phe Gln Glu Ser Ile Gly Arg Gln Val Thr Phe Val Gln Ser
            35                  40                  45

Asn Glu Ser Tyr Ser Lys Gln Asn Val Ile Arg Gly Leu His Tyr Gln
        50                  55                  60

Val Ile Arg Pro Gln Gly Lys Leu Val Arg Val Glu Gly Glu Val
65                  70                  75                  80

Phe Asp Ile Ala Val Asp Leu Arg Lys Ser Leu Gly Val Ile Val Pro
                85                  90                  95

His Tyr Leu Met Ile Phe Lys Lys Leu Asp Ile Glu Gly Cys Tyr Leu
                100                 105                 110

Ile Glu Phe Asn Lys Phe Ile Asp Ser Arg Gly Thr Phe Val Lys Thr
                115                 120                 125

Phe His Ser Asp Phe Phe Ser Glu Asn Gly Ile Val Leu Asp Met Arg
            130                 135                 140

Glu Glu Phe Tyr Ser Ile Ser Ala Lys Asn Val Ile Arg Gly Met His
145                 150                 155                 160

Phe Gln Met Pro Pro Ala Glu His Asp Lys Leu Val Tyr Cys Val Asn
                165                 170                 175

Gly Ala Val Leu Asp Val Ile Leu Asp Ile Arg Lys Asp Ser Pro Thr
                180                 185                 190

Phe Gly Gln Trp Val Gly Val Leu Leu Ser Asp Lys Asn Asn His Gln
            195                 200                 205

Leu Trp Ile Pro Glu Gly Phe Gly Phe Gln Val Leu Ser Pro
210                 215                 220

Ser Ala Lys Phe Gln Tyr Met Val Thr Asp Tyr Trp Tyr Pro Glu His
225                 230                 235                 240

Asp Arg Cys Ile Arg Phe Asn Asp Ser Asp Ile Asn Ile Lys Trp Lys
                245                 250                 255

Glu Gly Ile Ile Ser Glu Gln Gln Val Ile Glu Tyr Lys Leu Ser Ser
                260                 265                 270

Lys Asp Ile Ser Gly Asn Ser Leu Ala Asp Ala Glu Val Phe
                275                 280                 285
```

(2) INFORMATION FOR SEQ ID NO:43:

(i) SEQUENCE CHARACTERISTICS:
        (A) LENGTH: 88 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:43:

```
Ser Lys Thr Tyr Gly Glu Tyr Phe Ser Ile Glu Leu Ser Tyr Glu Asn
 1               5                  10                  15

Ser Leu Ala Leu Trp Val Pro Lys Gly Leu Ala His Gly Phe Leu Ser
                20                  25                  30

Leu Ala Asp Asn Ser Ile Met Phe Tyr Lys Thr Ser Ser Val His Asn
            35                  40                  45
```

```
Val Glu Cys Asp Ser Gly Ile Lys Trp Asn Ser Phe Gly Phe Lys Trp
 50                  55                  60
Pro Ile Asp Asn Pro Ile Ile Ser Glu Lys Asp Asn Ser Leu Cys Tyr
 65                  70                  75                  80
Phe Asp Glu Phe Asp Ser Ser Phe
                 85
```

(2) INFORMATION FOR SEQ ID NO:44:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:44:

```
Ile Asp Arg Gly Phe Phe Gly Ser Val Arg Gly His Phe Lys Val Gly
  1               5                  10                  15
Leu Asp Val Asp Arg Ser Thr Phe Trp Val Leu Trp Gly His Phe Leu
                 20                  25                  30
Tyr Glu Ile Glu
             35
```

(2) INFORMATION FOR SEQ ID NO:45:

(i) SEQUENCE CHARACTERISTICS:
        (A) LENGTH: 401 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:45:

```
Met Lys Arg Ala Leu Thr Asp Leu Ala Ile Phe Gly Gly Pro Glu Ala
  1               5                  10                  15
Phe Leu His Thr Leu Tyr Val Gly Arg Pro Thr Val Gly Asp Arg Glu
                 20                  25                  30
Arg Phe Phe Ala Arg Leu Glu Trp Ala Leu Asn Asn Asn Trp Leu Thr
                 35                  40                  45
Asn Gly Gly Pro Leu Val Arg Glu Phe Glu Gly Arg Val Ala Asp Leu
 50                  55                  60
Ala Gly Val Arg His Cys Val Ala Thr Cys Asn Ala Thr Val Ala Leu
 65                  70                  75                  80
Gln Leu Val Leu Arg Ala Ser Asp Val Ser Gly Glu Val Val Met Pro
                 85                  90                  95
Ser Met Thr Phe Ala Ala Thr Ala His Ala Ala Ser Trp Leu Gly Leu
                100                 105                 110
Glu Pro Val Phe Cys Asp Val Asp Pro Glu Thr Gly Leu Leu Asp Pro
                115                 120                 125
Glu His Val Ala Ser Leu Val Thr Pro Arg Thr Gly Ala Ile Ile Gly
                130                 135                 140
Val His Leu Trp Gly Arg Pro Ala Pro Val Glu Ala Leu Glu Lys Ile
145                 150                 155                 160
Ala Ala Glu His Gln Val Lys Leu Phe Phe Asp Ala Ala His Ala Leu
                165                 170                 175
Gly Cys Thr Ala Gly Gly Arg Pro Val Gly Ala Phe Gly Asn Ala Glu
                180                 185                 190
```

```
Val Phe Ser Phe His Ala Thr Lys Ala Val Thr Ser Phe Glu Gly Gly
            195                 200                 205

Ala Ile Val Thr Asp Asp Gly Leu Leu Ala Asp Arg Ile Arg Ala Met
210                 215                 220

His Asn Phe Gly Ile Ala Pro Asp Lys Leu Val Thr Asp Val Gly Thr
225                 230                 235                 240

Asn Gly Lys Met Ser Glu Cys Ala Ala Met Gly Leu Thr Ser Leu
            245                 250                 255

Asp Ala Phe Ala Glu Thr Arg Val His Asn Arg Leu Asn His Ala Leu
            260                 265                 270

Tyr Ser Asp Glu Leu Arg Asp Val Arg Gly Ile Ser Val His Ala Phe
            275                 280                 285

Asp Pro Gly Glu Gln Asn Asn Tyr Gln Tyr Val Ile Ile Ser Val Asp
290                 295                 300

Ser Ala Ala Thr Gly Ile Asp Arg Asp Gln Leu Gln Ala Ile Leu Arg
305                 310                 315                 320

Ala Glu Lys Val Val Ala Gln Pro Tyr Phe Ser Pro Gly Cys His Gln
            325                 330                 335

Met Gln Pro Tyr Arg Thr Glu Pro Pro Leu Arg Leu Glu Asn Thr Glu
            340                 345                 350

Gln Leu Ser Asp Arg Val Leu Ala Leu Pro Thr Gly Pro Ala Val Ser
            355                 360                 365

Ser Glu Asp Ile Arg Arg Val Cys Asp Ile Ile Arg Leu Ala Ala Thr
370                 375                 380

Ser Gly Glu Leu Ile Asn Ala Gln Trp Asp Gln Arg Thr Arg Asn Gly
385                 390                 395                 400

Ser (2) INFORMATION FOR SEQ ID NO:46:

(i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:46:

Met Asp Val Pro Phe Leu Asp Leu Gln Ala Ala Tyr Leu Glu Leu Arg
1               5                   10                  15

Ser Asp Ile Asp Gln Ala Cys Arg Arg Val Leu Gly Ser Gly Trp Tyr
            20                  25                  30

Leu His Gly Pro Glu Asn Glu Ala Phe Glu Ala Glu Phe Ala Ala Tyr
            35                  40                  45

Cys Glu Asn Ala His Cys Val Thr Val Gly Ser Gly Cys Asp Ala Leu
50                  55                  60

Glu Leu Ser Leu Val Ala Leu Gly Val Gly Gln Gly Asp Glu Val Ile
65                  70                  75                  80

Val Pro Ser His Thr Phe Ile Ala Thr Trp Leu Gly Val Pro Val Gly
            85                  90                  95

Ala Val Pro Val Pro Val Glu Pro Glu Gly Val Ser His Thr Leu Asp
            100                 105                 110

Pro Ala Leu Val Glu Gln Ala Ile Thr Pro Arg Thr Ala Ala Ile Leu
            115                 120                 125

Pro Val His Leu Tyr Gly His Pro Ala Asp Leu Asp Ala Leu Arg Ala
            130                 135                 140
```

Ile Ala Asp Arg His Gly Leu Ala Leu Val Glu Asp Val Ala Gln Ala
145                 150                 155                 160

Val Gly Ala Arg His Arg Gly His Arg Val Gly Ala Gly Ser Asn Ala
                165                 170                 175

Ala Ala Phe Ser Phe Tyr Pro Gly Lys Asn Leu Gly Ala Leu Gly Asp
            180                 185                 190

Gly Gly Ala Val Val Thr Thr Asp Pro Ala Leu Ala Glu Arg Ile Arg
            195                 200                 205

Leu Leu Arg Asn Tyr Gly Ser Lys Gln Lys Tyr Val His Glu Val Arg
210                 215                 220

Gly Thr Asn Ala Arg Leu Asp Glu Leu Gln Ala Ala Val Leu Arg Val
225                 230                 235                 240

Lys Leu Arg His Leu Asp Asp Trp Asn Ala Arg Arg Thr Thr Leu Ala
                245                 250                 255

Gln His Tyr Gln Thr Glu Leu Lys Asp Val Pro Gly Ile Thr Leu Pro
            260                 265                 270

Glu Thr His Pro Trp Ala Asp Ser Ala Trp His Leu Phe Val Leu Arg
            275                 280                 285

Cys Glu Asn Arg Asp His Leu Gln Arg His Leu Thr Asp Ala Gly Val
290                 295                 300

Gln Thr Leu Ile His Tyr Pro Thr Pro Val His Leu Ser Pro Ala Tyr
305                 310                 315                 320

Ala Asp Leu Gly Leu Pro Pro Gly Ser Phe Pro Val Ala Glu Ser Leu
                325                 330                 335

Ala Gly Glu Val Leu Ser Leu Pro Ile Gly Pro His Leu Ser Arg Glu
            340                 345                 350

Ala Ala Asp His Val Ile Ala Thr Leu Lys Ala Gly Ala
            355                 360                 365

(2) INFORMATION FOR SEQ ID NO:47:

(i) SEQUENCE CHARACTERISTICS:
        (A) LENGTH: 436 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:47:

Met Ser Gln Glu Glu Leu Arg Gln Gln Ile Ala Glu Leu Val Ala Gln
1               5                   10                  15

Ala Glu Thr Ala Met Ala Pro Lys Pro Phe Glu Ala Gly Lys Ser Val
            20                  25                  30

Val Pro Pro Ser Gly Lys Val Ile Gly Thr Lys Glu Leu Gln Leu Met
        35                  40                  45

Val Glu Ala Ser Leu Asp Gly Trp Leu Thr Thr Gly Arg Phe Asn Asp
    50                  55                  60

Ala Phe Glu Lys Lys Leu Gly Glu Tyr Leu Gly Val Pro Tyr Val Leu
65                  70                  75                  80

Thr Thr Thr Ser Gly Ser Ser Ala Asn Leu Leu Ala Leu Thr Ala Leu
                85                  90                  95

Thr Ser Pro Lys Leu Gly Val Arg Ala Leu Lys Pro Gly Asp Glu Val
            100                 105                 110

Ile Thr Val Ala Ala Gly Phe Pro Thr Thr Val Asn Pro Thr Ile Gln
            115                 120                 125

-continued

Asn Gly Leu Ile Pro Val Phe Val Asp Val Asp Ile Pro Thr Tyr Asn
130                     135                     140

Val Asn Ala Ser Leu Ile Glu Ala Ala Val Ser Asp Lys Thr Lys Ala
145                     150                     155                     160

Ile Met Ile Ala His Thr Leu Gly Asn Leu Phe Asp Leu Ala Glu Val
                        165                     170                     175

Arg Arg Val Ala Asp Lys Tyr Asn Leu Trp Leu Ile Glu Asp Cys Cys
                        180                     185                     190

Asp Ala Leu Gly Ser Thr Tyr Asp Gly Lys Met Ala Gly Thr Phe Gly
                        195                     200                     205

Asp Ile Gly Thr Val Ser Phe Tyr Pro Ala His His Ile Thr Met Gly
                210                     215                     220

Glu Gly Gly Ala Val Phe Thr Gln Ser Ala Glu Leu Lys Ser Ile Ile
225                     230                     235                     240

Glu Ser Phe Arg Asp Trp Gly Arg Asp Cys Tyr Cys Ala Pro Gly Cys
                        245                     250                     255

Asp Asn Thr Cys Lys Lys Arg Phe Gly Gln Gln Leu Gly Ser Leu Pro
                260                     265                     270

Phe Gly Tyr Asp His Lys Tyr Thr Tyr Ser His Leu Gly Tyr Asn Ile
                        275                     280                     285

Lys Ile Thr Asp Met Gln Ala Ala Cys Gly Leu Ala Gln Leu Glu Pro
290                     295                     300

Ile Glu Glu Phe Val Glu Lys Arg Lys Ala Asn Phe Lys Tyr Leu Lys
305                     310                     315                     320

Asp Ala Leu Gln Ser Cys Ala Asp Phe Ile Glu Leu Pro Glu Ala Thr
                        325                     330                     335

Glu Asn Ser Asp Pro Ser Trp Phe Gly Phe Pro Ile Thr Leu Lys Glu
                        340                     345                     350

Asp Ser Gly Val Ser Arg Ile Asp Leu Val Lys Phe Leu Asp Glu Ala
                        355                     360                     365

Lys Val Gly Thr Arg Leu Leu Phe Ala Gly Asn Leu Thr Arg Gln Pro
                        370                     375                     380

Tyr Phe His Asp Val Lys Tyr Arg Val Val Gly Glu Leu Thr Asn Thr
385                     390                     395                     400

Asp Arg Ile Met Asn Gln Thr Phe Trp Ile Gly Ile Tyr Pro Gly Leu
                        405                     410                     415

Thr His Asp His Leu Asp Tyr Val Val Ser Lys Phe Glu Glu Phe Phe
                        420                     425                     430

Gly Leu Asn Phe
            435

(2) INFORMATION FOR SEQ ID NO:48:

(i) SEQUENCE CHARACTERISTICS:
        (A) LENGTH: 409 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:48:

Val Ser Thr Tyr Val Trp Gln Tyr Leu Asn Glu Tyr Arg Glu Glu Arg
1                       5                       10                      15

Ala Asp Ile Leu Asp Ala Val Glu Thr Val Phe Glu Ser Gly Gln Leu
                20                      25                      30

Ile Leu Gly Thr Ser Val Arg Ser Phe Glu Glu Glu Phe Ala Ala Tyr

```
                  35                  40                  45
His Gly Leu Pro Tyr Cys Thr Gly Val Asp Asn Gly Thr Asn Ala Leu
     50                  55                  60

Val Leu Gly Leu Pro Arg Gly Ser Gly Pro Ile Gly Gln Leu Glu Ala
 65                  70                  75                  80

Glu Phe Leu Ala Phe Leu Asp His Gly Val Arg Tyr Ala Val Thr Phe
                 85                  90                  95

Asn Ser Gly Thr Ser Ala Leu Leu Ala Ala Tyr Arg Ala Leu Gly Ile
                100                 105                 110

Gly Pro Gly Asp Glu Val Val Thr Val Ser Asn Thr Ala Ala Pro Thr
                115                 120                 125

Val Val Ala Ile Asp Ala Val Gly Ala Thr Pro Val Phe Val Asp Val
130                 135                 140

His Glu Glu Asn Tyr Leu Met Asp Thr Gly Arg Leu Arg Ser Val Ile
145                 150                 155                 160

Gly Pro Arg Thr Arg Cys Leu Leu Pro Val His Leu Tyr Gly Gln Ser
                165                 170                 175

Val Asp Met Thr Pro Val Leu Glu Leu Ala Ala Glu His Asp Leu Lys
                180                 185                 190

Val Leu Glu Asp Cys Ala Gln Ala His Gly Ala Arg Arg His Gly Arg
                195                 200                 205

Leu Val Gly Thr Gln Gly His Ala Ala Ala Phe Ser Phe Tyr Pro Thr
            210                 215                 220

Lys Val Leu Gly Ala Tyr Gly Asp Gly Gly Ala Val Val Thr Pro Asp
225                 230                 235                 240

Ala Glu Val Asp Arg Arg Leu Arg Arg Leu Arg Tyr Tyr Gly Met Gly
                245                 250                 255

Glu Arg Tyr Tyr Val Val Asp Thr Pro Gly His Asn Ser Arg Leu Asp
                260                 265                 270

Glu Val Gln Ala Glu Ile Leu Arg Arg Lys Leu Arg Arg Leu Asp Ala
                275                 280                 285

Tyr Val Glu Gly Arg Arg Ala Val Ala Arg Tyr Glu Glu Gly Leu
                290                 295                 300

Gly Asp Leu Asp Gly Leu Val Leu Pro Thr Ile Ala Glu Gly Asn Asp
305                 310                 315                 320

His Val Tyr Tyr Val Tyr Val Val Arg His Pro Glu Arg Asp Arg Ile
                325                 330                 335

Leu Glu Ala Leu Thr Ala Tyr Asp Ile His Leu Asn Ile Ser Tyr Pro
                340                 345                 350

Trp Pro Val His Thr Met Ser Gly Phe Ala His Leu Gly Tyr Gly Pro
                355                 360                 365

Gly Asp Leu Pro Val Thr Glu Arg Leu Ala Gly Glu Ile Phe Ser Leu
370                 375                 380

Pro Met Tyr Pro Ser Leu Arg Pro Asp Ala Gln Glu Lys Val Ile Asp
385                 390                 395                 400

Ala Val Arg Glu Val Val Gly Ser Leu
                405
```

(2) INFORMATION FOR SEQ ID NO:49:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:49:

```
Phe Ala Leu Gly Val Arg Glu Gly Val Glu Ala Ala Gly Pro Ala Leu
  1               5                  10                  15

Thr Tyr His Ala Ala Leu Ser Pro Val Phe Ala Leu Arg Gly Asp Val
                 20                  25                  30

Val Leu Val Asp Ile Asp Pro Val Ser Arg Gly Leu Asp Pro Lys Ala
             35                  40                  45

Leu Glu Ala Ala Ile Thr Glu Asn Thr Arg Val Val Thr Val Val His
         50                  55                  60

Gln Trp Gly His Pro Cys Asp Met Asp Ala Ile Leu Gly Val Ala Glu
 65              70                  75                  80

Arg Tyr Gly Leu Arg Val Leu Glu Asp Cys Ser His Ala His Gly Ser
                 85                  90                  95

Arg Tyr Lys Gly Lys Val Pro Gly Thr Phe Gly Asp Ala Ala Val Phe
                100                 105                 110

Ser Leu Gln Ala Asn Lys Ala Val Tyr Ala Gly Glu Gly Gly Ile Leu
                115                 120                 125

Val Thr Asp Asp Ala Leu Val Gln Asp Arg Ala Thr Leu Leu Ala Thr
            130                 135                 140

Thr Gly Thr Val Pro Gly Leu Gly His Arg Arg
145                 150                 155
```

(2) INFORMATION FOR SEQ ID NO:50:

(i) SEQUENCE CHARACTERISTICS:
        (A) LENGTH: 379 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:50:

```
Met Ser Ser Phe Gln Glu Leu Pro Arg Trp Pro Gln Leu Thr Asp Asp
  1               5                  10                  15

Asp Ile Glu Ala Ala Val Ala Ala Leu Arg Ser Asn Arg Leu Val Gly
                 20                  25                  30

Gln Gly Asn Ser Thr Val Glu Glu Phe Glu Ala Ala Leu Ala Ala Gly
                 35                  40                  45

Gln Gly Val Glu His Ala Val Ala Val Ser Thr Gly Thr Ala Ala Val
         50                  55                  60

His Leu Ala Leu His Ala Leu Asp Val Gly Pro Gly Asp Glu Val Ile
 65              70                  75                  80

Val Pro Thr His Thr Phe Ile Gly Ser Ala Ser Pro Val Thr Tyr Leu
                 85                  90                  95

Gly Ala Arg Pro Val Phe Ala Asp Val Thr Pro Asp Thr His Cys Leu
                100                 105                 110

Asp Pro Asp Ser Val Lys Ser Leu Ile Gly Glu Arg Thr Lys Ala Ile
            115                 120                 125

Val Val Val His Ile Asn Gly Ile Ala Ala Asp Met Ala Ala Leu Thr
            130                 135                 140

Ala Val Ala Ala Glu Ala Gly Val Pro Val Ile Glu Asp Ala Ala Gln
145                 150                 155                 160

Ala Leu Gly Thr Glu Ile Gly Gly Arg Pro Ile Gly Gly Phe Gly Asp
                165                 170                 175
```

```
Leu Ala Cys Val Ser Leu Phe Phe Glu Gln Lys Val Ile Thr Ser Gly
            180                 185                 190

Gly Glu Gly Gly Ala Val Ile Thr Asp Asn Pro Val Tyr Ala Glu Arg
        195                 200                 205

Val Arg Arg Leu Arg Ser His Gly Glu Gly Pro Val Ser Gly Ser Pro
210                 215                 220

Gly Met Ile Trp Ala His Glu Val Gly Tyr Asn Val Arg Leu Thr Ser
225                 230                 235                 240

Val Gln Ala Pro Ser Ala Ser Pro Ser Asn Lys Arg Leu Gly Asp Leu
                245                 250                 255

Val Glu Ala Arg Arg Asn Ala Ala Tyr Leu Ser Glu Arg Leu Ala
            260                 265                 270

Gly Val Glu Gly Leu Glu Leu Pro Val Glu Pro Gly Thr Thr His
        275                 280                 285

Ala Tyr Trp Lys Tyr Ala Val Arg Val Pro Gly Asp Gly Arg Arg
        290                 295                 300

Ser Ala Ala Asp Ile Ala Ala His Leu Arg Ser Arg Gly Val Pro Val
305                 310                 315                 320

Leu Leu Arg Tyr Pro Tyr Pro Leu His Lys Gln Pro Ala Phe Ala Glu
                325                 330                 335

Tyr His Gly Val Ser Leu Pro Val Ala Glu Arg Leu Ser Gln Glu Leu
                340                 345                 350

Leu Ala Leu Pro Ser His Pro Gly Leu Val Glu Gly His Leu Asp His
                355                 360                 365

Ala Val Glu Glu Val Arg Lys Ala Val Ala Ser
        370                 375

(2) INFORMATION FOR SEQ ID NO:51:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:51:

Leu Leu Ala Val Leu Phe Glu Phe Ala Tyr Gly Val Gly Ala Leu Leu
1               5                   10                  15

Ala Leu Val Gly Asp Glu Val Ile Pro Thr Phe Thr Val Gly Pro Val
            20                  25                  30

Phe Val Asp Val Asp Thr Leu Asp Pro Val Ile Thr Ala Ile Val His
        35                  40                  45

Gly Asp Met Ala Leu Ile Glu Asp Ala Ala Gly Val Gly Phe Gly
    50                  55                  60

Phe Ser Phe Tyr Lys Gly Glu Gly Gly Ala Val Val Thr Asp Leu Glu
65                  70                  75                  80

Arg Arg Leu Arg Tyr Gly Tyr Gly Asn Arg Leu Glu Gln Ala Leu Leu
                85                  90                  95

Arg Leu Gly Tyr Tyr Asp Leu Leu Val Tyr His Phe Ala Leu Glu Leu
            100                 105                 110

Leu Leu Pro Pro Leu Glu Asp Val Val
            115                 120

(2) INFORMATION FOR SEQ ID NO:52:

(i) SEQUENCE CHARACTERISTICS:
```

(A) LENGTH: 415 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:52:

| Val | Arg | Val | Leu | Leu | Thr | Ser | Phe | Ala | His | Arg | Thr | His | Phe | Gln | Gly |
|---|---|---|---|---|---|---|---|---|---|---|---|---|---|---|---|
| 1 | | | | 5 | | | | | 10 | | | | | 15 | |

| Leu | Val | Pro | Leu | Ala | Trp | Ala | Leu | Arg | Thr | Ala | Gly | His | Asp | Val | Arg |
|---|---|---|---|---|---|---|---|---|---|---|---|---|---|---|---|
| | | | 20 | | | | | 25 | | | | | 30 | | |

| Val | Ala | Ala | Gln | Pro | Ala | Leu | Thr | Asp | Ala | Val | Ile | Gly | Ala | Gly | Leu |
|---|---|---|---|---|---|---|---|---|---|---|---|---|---|---|---|
| | | 35 | | | | | 40 | | | | | 45 | | | |

| Thr | Ala | Val | Pro | Val | Gly | Ser | Asp | His | Arg | Leu | Phe | Asp | Ile | Val | Pro |
|---|---|---|---|---|---|---|---|---|---|---|---|---|---|---|---|
| | 50 | | | | | 55 | | | | | 60 | | | | |

| Glu | Val | Ala | Ala | Gln | Val | His | Arg | Tyr | Ser | Phe | Tyr | Leu | Asp | Phe | Tyr |
|---|---|---|---|---|---|---|---|---|---|---|---|---|---|---|---|
| 65 | | | | | 70 | | | | | 75 | | | | | 80 |

| His | Arg | Glu | Gln | Glu | Leu | His | Ser | Trp | Glu | Phe | Leu | Leu | Gly | Met | Gln |
|---|---|---|---|---|---|---|---|---|---|---|---|---|---|---|---|
| | | | | 85 | | | | | 90 | | | | | 95 | |

| Glu | Ala | Thr | Ser | Arg | Trp | Val | Tyr | Pro | Val | Val | Asn | Asn | Asp | Ser | Phe |
|---|---|---|---|---|---|---|---|---|---|---|---|---|---|---|---|
| | | | | 100 | | | | | 105 | | | | | 110 | |

| Val | Ala | Glu | Leu | Val | Asp | Phe | Ala | Arg | Asp | Trp | Arg | Pro | Asp | Leu | Val |
|---|---|---|---|---|---|---|---|---|---|---|---|---|---|---|---|
| | | | 115 | | | | | 120 | | | | | 125 | | |

| Leu | Trp | Glu | Pro | Phe | Thr | Phe | Ala | Gly | Ala | Val | Ala | Ala | Arg | Ala | Cys |
|---|---|---|---|---|---|---|---|---|---|---|---|---|---|---|---|
| | 130 | | | | | 135 | | | | | 140 | | | | |

| Gly | Ala | Ala | His | Ala | Arg | Leu | Leu | Trp | Gly | Ser | Asp | Leu | Thr | Gly | Tyr |
|---|---|---|---|---|---|---|---|---|---|---|---|---|---|---|---|
| 145 | | | | | 150 | | | | | 155 | | | | | 160 |

| Phe | Arg | Gly | Arg | Phe | Gln | Ala | Gln | Arg | Leu | Arg | Arg | Pro | Pro | Glu | Asp |
|---|---|---|---|---|---|---|---|---|---|---|---|---|---|---|---|
| | | | | 165 | | | | | 170 | | | | | 175 | |

| Arg | Pro | Asp | Pro | Leu | Gly | Thr | Trp | Leu | Thr | Glu | Val | Ala | Gly | Arg | Phe |
|---|---|---|---|---|---|---|---|---|---|---|---|---|---|---|---|
| | | | 180 | | | | | 185 | | | | | 190 | | |

| Gly | Val | Glu | Phe | Gly | Glu | Asp | Leu | Ala | Val | Gly | Gln | Trp | Ser | Val | Asp |
|---|---|---|---|---|---|---|---|---|---|---|---|---|---|---|---|
| | | 195 | | | | | 200 | | | | | 205 | | | |

| Gln | Leu | Pro | Pro | Ser | Phe | Arg | Leu | Asp | Thr | Gly | Met | Glu | Thr | Val | Val |
|---|---|---|---|---|---|---|---|---|---|---|---|---|---|---|---|
| | 210 | | | | | 215 | | | | | 220 | | | | |

| Ala | Arg | Thr | Leu | Pro | Tyr | Asn | Gly | Ala | Ser | Val | Pro | Asp | Trp | Leu | |
|---|---|---|---|---|---|---|---|---|---|---|---|---|---|---|---|
| 225 | | | | | 230 | | | | | 235 | | | | | 240 |

| Lys | Lys | Gly | Ser | Ala | Thr | Arg | Arg | Ile | Cys | Ile | Thr | Gly | Gly | Phe | Ser |
|---|---|---|---|---|---|---|---|---|---|---|---|---|---|---|---|
| | | | | 245 | | | | | 250 | | | | | 255 | |

| Gly | Leu | Gly | Leu | Ala | Ala | Asp | Ala | Asp | Gln | Phe | Ala | Arg | Thr | Leu | Ala |
|---|---|---|---|---|---|---|---|---|---|---|---|---|---|---|---|
| | | | 260 | | | | | 265 | | | | | 270 | | |

| Gln | Leu | Ala | Arg | Phe | Asp | Gly | Glu | Ile | Val | Val | Thr | Gly | Ser | Gly | Pro |
|---|---|---|---|---|---|---|---|---|---|---|---|---|---|---|---|
| | | 275 | | | | | 280 | | | | | 285 | | | |

| Asp | Thr | Ser | Ala | Val | Pro | Asp | Asn | Ile | Arg | Leu | Val | Asp | Phe | Val | Pro |
|---|---|---|---|---|---|---|---|---|---|---|---|---|---|---|---|
| | 290 | | | | | 295 | | | | | 300 | | | | |

| Met | Gly | Val | Leu | Leu | Gln | Asn | Cys | Ala | Ala | Ile | Ile | His | His | Gly | Gly |
|---|---|---|---|---|---|---|---|---|---|---|---|---|---|---|---|
| 305 | | | | | 310 | | | | | 315 | | | | | 320 |

| Ala | Gly | Thr | Trp | Ala | Thr | Ala | Leu | His | His | Gly | Ile | Pro | Gln | Ile | Ser |
|---|---|---|---|---|---|---|---|---|---|---|---|---|---|---|---|
| | | | | 325 | | | | | 330 | | | | | 335 | |

| Val | Ala | His | Glu | Trp | Asp | Cys | Met | Leu | Arg | Gly | Gln | Gln | Thr | Ala | Glu |
|---|---|---|---|---|---|---|---|---|---|---|---|---|---|---|---|
| | | | | 340 | | | | | 345 | | | | | 350 | |

| Leu | Gly | Ala | Gly | Ile | Tyr | Leu | Arg | Pro | Asp | Glu | Val | Asp | Ala | Asp | Ser |
|---|---|---|---|---|---|---|---|---|---|---|---|---|---|---|---|
| | | | 355 | | | | | 360 | | | | | 365 | | |

| Leu | Ala | Ser | Ala | Leu | Thr | Gln | Val | Val | Glu | Asp | Pro | Thr | Tyr | Thr | Glu |
|---|---|---|---|---|---|---|---|---|---|---|---|---|---|---|---|
| | 370 | | | | | 375 | | | | | 380 | | | | |

Asn Ala Val Lys Leu Arg Glu Glu Ala Leu Ser Asp Pro Thr Pro Gln
385                 390                 395                 400

Glu Ile Val Pro Arg Leu Glu Glu Leu Thr Arg Arg His Ala Gly
                405                 410                 415

(2) INFORMATION FOR SEQ ID NO:53:

(i) SEQUENCE CHARACTERISTICS:
        (A) LENGTH: 421 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:53:

Met Arg Val Val Phe Ser Ser Met Ala Ser Lys Ser His Leu Phe Gly
1               5                   10                  15

Leu Val Pro Leu Ala Trp Ala Phe Arg Ala Ala Gly His Glu Val Arg
                20                  25                  30

Val Val Ala Ser Pro Ala Leu Thr Glu Asp Ile Thr Ala Ala Gly Leu
            35                  40                  45

Thr Ala Val Pro Val Gly Thr Asp Val Asp Leu Val Asp Phe Met Thr
        50                  55                  60

His Ala Gly His Asp Ile Ile Asp Tyr Val Arg Ser Leu Asp Phe Ser
65                  70                  75                  80

Glu Arg Asp Pro Ala Thr Leu Thr Trp Glu His Leu Arg Gly Met Gln
                85                  90                  95

Thr Val Leu Thr Pro Thr Phe Tyr Ala Leu Met Ser Pro Asp Thr Leu
            100                 105                 110

Ile Glu Gly Met Val Ser Phe Cys Arg Lys Trp Arg Pro Asp Leu Val
        115                 120                 125

Ile Trp Glu Pro Leu Thr Phe Ala Ala Pro Ile Ala Gly Ala Val Thr
        130                 135                 140

Gly Thr Pro His Ala Arg Leu Leu Trp Gly Pro Asp Ile Thr Thr Arg
145                 150                 155                 160

Ala Arg Gln Asn Phe Leu Gly Leu Leu Pro Asp Gln Pro Glu Glu His
                165                 170                 175

Arg Glu Gly Pro Leu Ala Glu Trp Leu Thr Trp Thr Leu Glu Lys Tyr
            180                 185                 190

Gly Gly Pro Ala Phe Asp Glu Glu Val Val Gly Gln Trp Thr Ile
        195                 200                 205

Asp Pro Ala Pro Ala Ala Ile Arg Leu Asp Thr Gly Leu Lys Thr Val
210                 215                 220

Gly Met Arg Tyr Val Asp Tyr Asn Gly Pro Ser Val Val Pro Glu Trp
225                 230                 235                 240

Leu His Asp Glu Pro Glu Arg Arg Val Cys Leu Thr Leu Gly Ile
                245                 250                 255

Ser Ser Arg Glu Asn Ser Ile Gly Gln Val Ser Ile Glu Glu Leu Leu
            260                 265                 270

Gly Ala Val Gly Asp Val Asp Ala Glu Ile Ile Ala Thr Phe Asp Ala
        275                 280                 285

Gln Gln Leu Glu Gly Val Ala Asn Ile Pro His Asn Val Arg Thr Val
    290                 295                 300

Gly Phe Val Pro Met His Ala Leu Leu Pro Thr Cys Ala Ala Thr Val
305                 310                 315                 320

```
His His Gly Gly Pro Gly Ser Trp His Thr Ala Ile His Gly Val
            325                 330                 335

Pro Gln Val Ile Leu Pro Asp Gly Trp Asp Thr Gly Val Arg Ala Gln
            340                 345                 350

Arg Thr Gln Glu Phe Gly Ala Gly Ile Ala Leu Pro Val Pro Glu Leu
            355                 360                 365

Thr Pro Asp Gln Leu Arg Glu Ser Val Lys Arg Val Leu Asp Asp Pro
            370                 375                 380

Ala His Arg Ala Gly Ala Ala Arg Met Arg Asp Asp Met Leu Ala Glu
385                 390                 395                 400

Pro Ser Pro Ala Glu Val Val Gly Ile Cys Glu Glu Leu Ala Ala Gly
            405                 410                 415

Arg Arg Glu Pro Arg
            420

(2) INFORMATION FOR SEQ ID NO:54:

(i) SEQUENCE CHARACTERISTICS:
        (A) LENGTH: 431 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:54:

Met Lys Val Leu Val Thr Ala Phe Ala Met Asp Ala His Phe Asn Gly
1               5                   10                  15

Val Val Pro Leu Ala Trp Ala Leu Arg Ala Ala Gly His Asp Val Arg
            20                  25                  30

Val Ala Ser Gln Pro Ala Leu Thr Asp Ser Ile Thr Arg Ala Gly Leu
        35                  40                  45

Thr Ala Val Pro Val Gly Thr Asp His Gln Val Gln Ala Ala Met Gly
    50                  55                  60

Ala Met Ala Pro Gly Val Phe Ala Leu His Leu Asn Pro Asp Tyr Leu
65                  70                  75                  80

Glu Asn Arg Pro Glu Leu Leu Asp Leu Glu Phe Leu Glu Ala Ser Thr
                85                  90                  95

Ser Met Leu Thr Ala Ala Phe Tyr Ala Gln Ile Asn Asn Asp Ser Met
            100                 105                 110

Ile Asp Glu Met Val Asp Phe Ala Ala Trp Trp Arg Pro Asp Leu Val
            115                 120                 125

Val Trp Glu Pro Phe Thr Phe Gly Ala Val Ala Ala Gln Val Thr
    130                 135                 140

Gly Ala Ala Gln Ala Arg Leu Leu Trp Gly Pro Asp Leu Phe Leu Arg
145                 150                 155                 160

Val His Asp Arg Phe Gln Gln Val Leu His Glu Val Pro Ala Glu Arg
                165                 170                 175

Arg Asp Asp Ala Leu Glu Glu Trp Leu Thr Trp Thr Leu Glu Arg His
            180                 185                 190

Gly Ala Ala Phe Gly Pro Glu Val Ile Ser Gly His Trp Thr Ile Asp
        195                 200                 205

Gln Met Pro Pro Ser Val Arg Phe Ala Thr Ala Arg Pro Thr Val Pro
    210                 215                 220

Met Arg Phe Val Pro Tyr Asn Gly Val Pro Ala Val Pro Pro
225                 230                 235                 240

Trp Leu Arg Ala Asp Pro Gly Arg Pro Arg Val Leu Leu Thr Gln Gly
```

―continued

```
            245                 250                 255
Ile Thr Glu Arg Ser Thr Gly Phe Thr Gly Leu Pro Arg Ala Gly Glu
            260                 265                 270

Leu Leu Ala Ser Ile Ala Glu Leu Asp Ala Glu Val Val Ala Thr Val
            275                 280                 285

Lys Ala Glu Glu Arg Glu Gly Leu Pro Pro Leu Pro Gly Asn Val Arg
            290                 295                 300

Val Val Asp Ser Leu Ser Leu His Val Val Leu Pro Ser Cys Ala Ala
305                 310                 315                 320

Val Val His His Gly Gly Ala Gly Thr Trp Ala Thr Ala Ala Leu His
                    325                 330                 335

Gly Val Pro Gln Leu Ala Leu Ala Trp Gln Trp Asp Asp Val Phe Arg
                    340                 345                 350

Ala Gly Gln Leu Glu Lys Leu Gly Ala Gly Ile Phe Leu Pro Pro His
                    355                 360                 365

Gly Glu Gly Ala Ser Ala Gly Arg Val Arg Asp Arg Leu Ala Gln Val
                    370                 375                 380

Leu Ala Glu Pro Ser Phe Arg Gln Gly Ala Ala Arg Ile Arg Ala Glu
385                 390                 395                 400

Met Leu Arg Thr Pro Ala Pro Gly Ala Val Val Pro Thr Leu Glu Gln
                    405                 410                 415

Leu Thr Ala Arg His Arg Ala Pro Ala Gly Gln Gly Val Arg His
                    420                 425                 430
```

(2) INFORMATION FOR SEQ ID NO:55:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:55:

```
Val Ala His Phe Gly Val Pro Leu Ala Trp Ala Leu Arg Ala Gly His
1               5                   10                  15

Asp Val Arg Val Pro Ala Leu Thr Asp Ile Ala Gly Leu Thr Ala Val
                20                  25                  30

Pro Val Gly Asp Val Asp Phe Glu Leu Tyr Asp Ile Met Val Phe Trp
            35                  40                  45

Arg Pro Asp Leu Val Trp Glu Pro Phe Thr Phe Val Ala Gly Ala Arg
        50                  55                  60

Leu Leu Trp Gly Asp Phe Pro Glu Arg Leu Trp Leu Thr Gly Phe Glu
65                  70                  75                  80

Gly Trp Ile Asp Pro Arg Leu Thr Thr Val Arg Tyr Asn Gly Val Val
                    85                  90                  95

Pro Trp Leu Arg Val Thr Gly Leu Asp Glu Ile Val Thr Pro Asn Val
                100                 105                 110

Arg Val Met Leu Cys Ala Ala Val His Gly Gly Trp Thr Ala
                115                 120                 125

His Gly Val Pro Gln Trp Asp Arg Leu Gly Ala Gly Ile Leu Val Asp
            130                 135                 140

Pro Ala Arg Glu Leu Pro Pro Val Val Glu Leu
145                 150                 155
```

(2) INFORMATION FOR SEQ ID NO:56:

(i) SEQUENCE CHARACTERISTICS:
    (A) LENGTH: 237 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:56:

```
Met Tyr Glu Gly Gly Phe Ala Glu Leu Tyr Asp Arg Phe Tyr Arg Gly
 1               5                  10                  15

Arg Gly Lys Asp Tyr Ala Ala Glu Ala Ala Gln Val Ala Arg Leu Val
            20                  25                  30

Arg Asp Arg Leu Pro Ser Ala Ser Ser Leu Leu Asp Val Ala Cys Gly
        35                  40                  45

Thr Gly Thr His Leu Arg Arg Phe Ala Asp Leu Phe Asp Asp Val Thr
 50                  55                  60

Gly Leu Glu Leu Ser Ala Ala Met Ile Glu Val Ala Arg Pro Gln Leu
 65                  70                  75                  80

Gly Gly Ile Pro Val Leu Gln Gly Asp Met Arg Asp Phe Ala Leu Asp
                85                  90                  95

Arg Glu Phe Asp Ala Val Thr Cys Met Phe Ser Ser Ile Gly His Met
               100                 105                 110

Arg Asp Gly Ala Glu Leu Asp Gln Ala Leu Ala Ser Phe Ala Arg His
           115                 120                 125

Leu Ala Pro Gly Gly Val Val Val Glu Pro Trp Trp Phe Pro Glu
130                 135                 140

Asp Phe Leu Asp Gly Tyr Val Ala Gly Asp Val Arg Asp Gly Asp
145                 150                 155                 160

Leu Thr Ile Ser Arg Val Ser His Ser Val Arg Ala Gly Gly Ala Thr
                165                 170                 175

Arg Met Glu Ile His Trp Val Val Asp Ala Val Asn Gly Pro Arg
            180                 185                 190

His His Val Glu His Tyr Glu Ile Thr Leu Phe Glu Arg Gln Gln Tyr
            195                 200                 205

Glu Lys Ala Phe Thr Ala Ala Gly Cys Ala Val Gln Tyr Leu Glu Gly
        210                 215                 220

Gly Pro Ser Gly Arg Gly Leu Phe Val Gly Val Arg Gly
225                 230                 235
```

(2) INFORMATION FOR SEQ ID NO:57:

(i) SEQUENCE CHARACTERISTICS:
    (A) LENGTH: 239 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:57:

```
Met Tyr Glu Asn Asp Ser Ala Ala Glu Val Tyr Asp Leu Leu Tyr Gln
 1               5                  10                  15

Asp Arg Lys Asp Tyr Ala Gly Glu Ala Ala Arg Val Thr Asp Leu Ile
            20                  25                  30

Arg Glu Arg Thr Pro Asp Ala Ala Ser Leu Leu Asp Ile Ala Cys Gly
        35                  40                  45

Thr Gly Thr His Leu Glu Ala Phe Ala Lys Leu Tyr Asp Arg Val Ser
 50                  55                  60
```

```
Gly Leu Glu Leu Ser Glu Trp Met Ala Ala Arg Ala Glu Glu Arg Leu
 65                  70                  75                  80

Pro Gly Val Thr Leu His Arg Gly Asp Met Arg Ala Phe Asp Leu Gly
                 85                  90                  95

Glu Thr Phe Asp Ala Val Val Cys Met Phe Ser Ser Ile Gly Tyr Leu
                100                 105                 110

Glu Thr Thr Ala Asp Leu Glu Asp Ala Val Ala Ala Met Ala Arg His
                115                 120                 125

Leu Thr Ala Asp Gly Val Leu Ala Val Glu Pro Trp Tyr Phe Pro Asp
    130                 135                 140

Thr Phe Leu Asp Gly His Val Ser Thr His Ala Leu Arg Thr Ala Pro
145                 150                 155                 160

Gly Asp Gln Gly Val Ala Arg Val Ser His Ser Thr Arg Glu Gly Gly
                165                 170                 175

Arg Thr Arg Met Glu Ile His Tyr Leu Ile Ala His Thr Ala Glu Gly
                180                 185                 190

Ile Arg His Arg Ser Glu Val Asp Tyr Leu Thr Leu Phe Ser Arg Ala
                195                 200                 205

Glu Tyr Glu Ala Ala Tyr Arg Lys Ala Gly Leu Asp Val Glu Tyr Val
    210                 215                 220

Val Thr Gly Glu Gly Ser Pro Gly Phe Phe Leu Gly Thr Arg Arg
225                 230                 235

(2) INFORMATION FOR SEQ ID NO:58:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:58:

Met Tyr Gly Ala Asp Leu Ala Arg Val Tyr Asp Leu Val His Arg Glu
  1               5                  10                  15

Arg Gly Lys Asp Tyr Arg Ala Arg Asp Arg Gly Gly Arg Arg Arg Gly
                 20                  25                  30

Pro Ala Glu Gln Ala Gly Ala Gly Arg Leu Leu Asp Val Ala Cys Gly
                 35                  40                  45

Thr Gly Gly His Leu Arg His Phe Ala Asp Leu Phe Ala His Val Glu
     50                  55                  60

Gly Val Glu Leu Ser Glu Pro Met Ala Glu Glu Ala Arg Ala Ala Leu
 65                  70                  75                  80

Pro Gly Val Thr Val His Ala Gly Asp Met Arg Asp Phe Arg Leu Gly
                 85                  90                  95

Thr Thr Phe Asp Val Val Thr Cys Met Phe Gly Ser Val Gly Tyr Met
                100                 105                 110

Thr Ser Val Ala Glu Leu Gly Arg Ala Leu Arg Met Phe Ala Arg His
                115                 120                 125

Leu Glu Pro Gly Gly Val Ala Val Val Asp Pro Trp Trp Phe Tyr Glu
    130                 135                 140

Thr Phe Ala Asp Gly His Val Ser Ala Asp Ile Val Thr Val Asp Gly
145                 150                 155                 160

Val Thr Val Ser Arg Val Ser His Ser Ala Arg Arg Gly Arg Thr Ser
                165                 170                 175
```

```
His Met Asp Val His Phe Val Val Ala Glu Pro Gly Ala Gly Ala Gln
            180                 185                 190

His Phe Val Asp Thr His Ile Ile Ser Leu Phe Ser Arg Ser Glu Tyr
            195                 200                 205

Glu Gln Ala Phe Arg Asp Gly Phe Ala Val Glu Tyr Leu Pro Glu
    210                 215                 220

Ala Pro Ser Gly Arg Gly Leu Phe Gly Val Arg Gly
225                 230                 235
```

(2) INFORMATION FOR SEQ ID NO:59:

(i) SEQUENCE CHARACTERISTICS:
        (A) LENGTH: 293 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:59:

```
Met Val Asp Ser Val Tyr Arg Thr Arg Ser Leu Gly Val Ala Ala Glu
 1               5                  10                  15

Gly Ile Pro Asp Gln Tyr Ala Asp Gly Glu Ala Ala Arg Val Trp Gln
            20                  25                  30

Leu Tyr Ile Gly Asp Thr Arg Ser Arg Thr Ala Glu Tyr Lys Ala Trp
            35                  40                  45

Leu Leu Gly Leu Leu Arg Gln His Gly Cys His Arg Val Leu Asp Val
 50                  55                  60

Ala Cys Gly Thr Gly Val Asp Ser Ile Met Leu Val Glu Glu Gly Phe
 65                  70                  75                  80

Ser Val Thr Ser Val Asp Ala Ser Asp Lys Met Leu Lys Tyr Ala Leu
                 85                  90                  95

Lys Glu Arg Trp Asn Arg Arg Lys Glu Pro Ala Phe Asp Lys Trp Val
            100                 105                 110

Ile Glu Glu Ala Asn Trp Leu Thr Leu Asp Lys Asp Val Pro Ala Gly
            115                 120                 125

Asp Gly Phe Asp Ala Val Ile Cys Leu Gly Asn Ser Phe Ala His Leu
130                 135                 140

Pro Asp Ser Lys Gly Asp Gln Ser Glu His Arg Leu Ala Leu Lys Asn
145                 150                 155                 160

Ile Ala Ser Met Val Arg Pro Gly Gly Leu Leu Val Ile Asp His Arg
                165                 170                 175

Asn Tyr Asp Tyr Ile Leu Ser Thr Gly Cys Ala Pro Pro Gly Lys Asn
            180                 185                 190

Ile Tyr Tyr Lys Ser Asp Leu Thr Lys Asp Ile Thr Thr Ser Val Leu
            195                 200                 205

Thr Val Asn Asn Lys Ala His Met Val Thr Leu Asp Tyr Thr Val Gln
            210                 215                 220

Val Pro Gly Ala Gly Arg Asp Gly Ala Pro Gly Phe Ser Lys Phe Arg
225                 230                 235                 240

Leu Ser Tyr Tyr Pro His Cys Leu Ala Ser Phe Thr Glu Leu Val Gln
                245                 250                 255

Glu Ala Phe Gly Gly Arg Cys Gln His Ser Val Leu Gly Asp Phe Lys
            260                 265                 270

Pro Tyr Arg Pro Gly Gln Ala Tyr Val Pro Cys Tyr Phe Ile His Val
            275                 280                 285

Leu Lys Lys Thr Gly
```

290

(2) INFORMATION FOR SEQ ID NO:60:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:60:

Tyr Ala Tyr Leu Asp Val Ala Cys Gly Thr Gly Phe Val Glu Ser Met
 1               5                  10                  15

Ala Leu Phe Asp Val Cys Met Ser Glu Ala Ala Gly Val Glu Trp Phe
            20                  25                  30

Phe Gly Met Tyr Val Gly Leu Phe Val Phe
            35                  40

POLYKETIDE-ASSOCIATED SUGAR BIOSYNTHESIS GENES

FIELD OF THE INVENTION

The present invention relates to methods for directing the biosynthesis of specific Poetide analogs by genetic manipulation. In particular, sugar biosynthesis genes are manipulated to produce precise, novel glycosylation-modified macrolides of predicted structure.

BACKGROUND OF THE INVENTION

Polyketides are a large class of natural products that includes many important antibiotic, antifungal, anticancer, and anti-helminthic compounds such as erythromycins, amphotericins, daunorubicins, and avermectins. Their synthesis proceeds by an ordered condensation of acyl esters to generate carbon chains of varying length, side chain, and reduction pattern that are differentially cyclized and subsequently modified to give the mature polyketides. For many polyketides, maturation includes the addition of one or more sugar residues to the cyclized carbon chain. The sugar residues are frequently critical to the biological activity of the mature polyketide.

Streptomyces and the closely related Saccharopolyspora genera are prodigious producers of polyketide metabolites. Because of the commercial significance of these compounds, a great amount of effort has been expended in the study of Streptomyces genetics. Consequently, much is known about Streptomyces and several cloning vectors exist for introducing DNA into these organisms.

Although many polyketides have been identified, there remains the need to obtain novel glycosylation modified (as defined herein) polyketide structures with enhanced properties. Current methods of obtaining such molecules include screening of biological samples and chemical modification of existing polyketides, both of which are costly and time consuming. Current screening methods are based on gross properties of the molecule, i.e. antibacterial, antifungal activity, etc., and both a priori knowledge of the structure of the molecules obtained or predetermination of enhanced properties are virtually impossible. Standard chemical modification of existing structures has been successfully employed, but is limited by the number of types of compounds obtainable. Furthermore, the poor yield of multistep chemical syntheses often limits the practicality of this approach. The following modifications to sugar residues bound to polyketides are particularly difficult or inefficient at the present time: change the stereochemistry of specific hydroxyl or methyl groups, change the oxidation state of specific hydroxyl groups, and deoxygenation of specific carbons. Accordingly, there exists a need to obtain molecules wherein such changes are specified and performed which would represent an improvement in the technology to produce altered glycosylation-modified polyketide molecules with predicted structure.

The present invention overcomes these problems by providing the genetic sequence of sugar biosynthesis genes involved in the biosynthesis of polyketide-associated sugars.

SUMMARY OF THE INVENTION

In one aspect, the present invention provides an isolated single or double stranded polynucleotide, typically DNA, having a nucleotide sequence which comprises a nucleotide sequence selected from the group consisting of (a) the sense sequence of FIG. 4A (SEQ ID NO:1) from about nucleotide position 54 to about nucleotide position 1136; the sense sequence of FIG. 4A from about nucleotide position 1147 to about nucleotide position 2412; sense sequence of FIG. 4A from about nucleotide position 2409 to about nucleotide position 3410; the sense sequence of FIG. 4B (SEQ ID NO:2) from about nucleotide position 80 to about nucleotide position 1048; the sense sequence of FIG. 4B from about nucleotide position 1048 to about nucleotide position 2295; the sense sequence of FIG. 4B from about nucleotide position 2348 to about nucleotide position 3061; the sense sequence of FIG. 4B from about nucleotide position 3214 to about nucleotide position 4677; the sense sequence of FIG. 4B from about nucleotide position 4674 to about nucleotide position 5879; the sense sequence of FIG. 4B from about nucleotide position 5917 to about nucleotide position 7386; and the sense sequence of FIG. 4B from about nucleotide position 7415 to about nucleotide position 7996; (b) sequences complementary to the sequences of (a); (c) sequences that, on expression, encode a polypeptide encoded by the sequences of (a); and (d) analogous sequences that hybridize under stringent conditions to the sequences of (a) and (b). A preferred molecule is a DNA molecule. In another embodiment, the polynucleotide is an RNA molecule.

In another embodiment, a DNA molecule of the present invention is contained in an expression vector. The expression vector preferably further comprises an enhancer-promoter operatively linked to the polynucleotide. In a preferred embodiment, the DNA molecule in the vector is one of the preferred sequences mentioned above. In an especially preferred embodiment, the DNA molecule in the vector is the sequence of FIG. 4B from about nucleotide position 80 to about nucleotide position 1048.

The present invention still further provides for a host cell transformed with a polynucleotide or expression vector of this invention. Preferably, the host cell is a bacterial cell selected from the group consisting of Saccharopolyspora spp., Streptomyces spp. and E. coli.

The present invention also provides methods to produce novel glycosylation modified polyketide structures by designing and introducing specified changes in the DNA governing the synthesis and attachment of sugar residues to polyketides. According to one method, the biosynthesis of specific glycosylation-modified polyketides is accomplished by genetic manipulation of a polyketide-producing microorganism comprising the steps of isolating a sugar biosynthesis gene-containing DNA sequence from those described above; identifying within the gene-containing DNA sequence one or more DNA fragments responsible for the biosynthesis of a polyketide-associated sugar or its attachment to the polyketide; creating one or more specified changes into the DNA fragment or fragments, thereby resulting in an altered DNA sequence; introducing the altered DNA sequence into a polyketide-producing microorganism to replace the original sequence whereby the altered DNA sequence, when translated, results in altered enzymatic activity capable of effecting the production of the specific glycosylation-modified polyketide; growing a culture of the altered polyketide-producing microorganism under conditions suitable for the formation of the specific glycosylation-modified polyketide; and isolating said specific glycosylation-modified polyketide from the culture.

In a second method the biosynthesis of specific glycosylation-modified polyketides is accomplished by isolating a sugar biosynthesis gene-containing DNA sequence from from those described above; identifying within the gene-containing DNA sequence one or more DNA fragments responsible for the biosynthesis of a polyketide-associated sugar or its attachment to the polyketide; reversing the strand orientation of the DNA fragment or fragments, thereby resulting in an altered DNA sequence which, when transcribed, results in production of an antisense mRNA; introducing the altered DNA sequence into a polyketide-producing microorganism having an mRNA capable of binding to the antisense MRNA which results in altered enzymatic activity capable of effecting the production of the specific glycosylation-modified polyketide; growing a culture of the altered polyketide-producing microorganism under conditions suitable for the formation of the specific glycosylation-modified polyketide; and isolating the specific glycosylation-modified polyketide from the culture.

In a third method the biosynthesis of specific glycosylation-modified polyketides is accomplished by isolating a sugar biosynthesis gene-containing DNA sequence from from those described above; identifying within the gene-containing DNA sequence one or more DNA fragments responsible for the biosynthesis of a polyketide-associated sugar or its attachment to the polyketide; introducing the DNA fragment or fragments into a distinct polyketide-producing microorganism whereupon transcription and translation of the DNA fragment or fragments generate an altered polyketide-producing microorganism that is capable of producing the specific glycosylation-modified polyketide; growing a culture of the polyketide-producing microorganism containing the DNA fragment or fragments under conditions suitable for the formation of the specific glycosylation-modified polyketide; and isolating the specific glycosylation-modified polyketide from the culture.

Preferably, the sugar biosynthesis gene-containing DNA sequence of the processes described above comprises genes which encode an enzymatic activity involved in the biosynthesis of L-mycarose and/or D-desosamine. More preferably, the sugar biosynthesis gene-containing DNA sequence comprises the sequence of FIG. 4B from about nucleotide position 80 to about nucleotide position 1048.

The present invention is especially useful in manipulating sugar biosynthesis genes from Streptomyces and Saccharopolyspora, organisms that provide over one-half of the clinically useful antibiotics.

BRIEF DESCRIPTION OF THE DRAWINGS

FIGS. 4A-1 through 4A-4 (SEQ ID NO:1) illustrate the nucleotide sequence of the sugar biosynthesis genes eryCII (coordinates 54–1136), eryCIII (coordinates 1147–2412), and eryBII (coordinates 2409–3410), with corresponding translation of the open reading frames (SEQ ID NO:31). Standard one letter codes for the amino acids appear beneath their respective nucleic acid codons as described herein.

FIGS. 4B-1 through 4B-9 (SEQ ID NO:2) illustrate the nucleotide sequence of the sugar biosynthesis genes eryBIV (coordinates 80–1048), eryBV (coordinates 1048–2295), eryCVI (coordinates 2348–3061), eryBVI (coordinates 3214–4677), eryCIV (coordinates 4674–5879), eryCV (coordinates 5917–7386), and eryBVII (coordinates 7415–7996) with corresponding translation of the putative open reading frames (SEQ ID NO:32). Standard one letter codes for the amino acids appear beneath their respective nucleic acid codons as described herein.

FIG. 5(A) illustrates the amino acid sequence identity between the sugar biosynthesis enzyme encoded by the eryBlV gene of Sac. erythraea (SEQ ID NO:33) and the sugar biosynthesis enzymes encoded by the ascF gene of Yersinia pseudotuberculosis (Thorson et al., J. Bacteriol., 176:5483 (1994)), the rfbJ gene of Salmonella enterica (Jiang et al., Mol. Microbiol., 5:695 (1991)), the strL gene of Streptomyces griseus (Pissowotzki et al., Mol. Gen. Genet. 241:193 (1993)) and the galE gene of Escherichia coli (Lemaire and Hill, Nucl. Acids Res. 14:7705 (1986)) which are SEQ ID NOS:34, 35, 36 and 37 respectively. A consensus sequence (SEQ ID NO:38) is also shown.

FIG. 5(B) illustrates the amino acid sequence identity between the sugar biosynthesis enzyme encoded by the eryBVII gene of Sac. erythraea (SEQ ID NO:39) and the sugar biosynthesis enzymes encoded by the strM gene of Streptonmyces griseus (Pissowotzki et al., Mol. Gen. Genet. 241:193 (1993)), the rfbC gene of Salmonella enterica (Jiang et al., Mol. Microbiol., 5:695 (1991)), the rfbF gene of Yersinia entezcolitica (Zhang et al., Mol. Microbiol., 9:309 (1993)), and the ascE gene of Yersinia pseudotuberculosis (Thorson et al., J. Bacteriol., 176:5483 (1994)) which are SEQ ID NOS:40, 41, 42 and 43 respectively. A consensus sequence (SEQ ID NO:44) is also shown.

FIG. 5(C) illustrates the amino acid sequence identity bee veen the sugar biosynthesis enzyme encoded by the eryCIV gene of Sac. erythraea (SEQ ID NO: 45) and the sugar biosynthesis enzymes encoded by the eryCI gene of Sac. erythraea (Dhillon et al., Mol. Microbiol., 3:1405 (1989)), the ascC gene of Yersinia pseudotuberculosis (Weigel et al., Biochemistry, 31:2129 (1992), Thorson et al., J. Am. Chem. Soc., 115:6993 (1993), Thorson et al., J. Bacteriol., 176:5483 (1994)), the dnrJ gene of Streptomyces peucetius (Stutzman-Engwall et al.,J. Bacteriol., 174:144 (1992)), the prgl gene of Streptomyces alboniger (Lacalle et al., EMBO J., 11:785 (1992)), and the strS gene of Streptomyces griseus (Distler et al., Gene, 115:105 (1992)). which are SEQ ID NOS:46, 47, 48, 49 and 50 respectively. A consensus sequence (SEQ ID NO:51) is also shown.

FIG. 5(D) illustrates the amino acid sequence identity between the sugar biosynthesis enzymes encoded by the eryBV and eryCIII genes of Sac. erythraea (SEQ ID NO:52 and 53 respectively) and the sugar biosynthesis enzyme encoded by the dnrS gene of Streptomyces peucetius (Otten et al., J. Bacteriol., 177:6688 (1995)) which is SEQ ID NO:54. A consensus sequence (SEQ ID NO:55) is also shown.

FIG. 5(E) illustrates the amino acid sequence identity between the sugar biosynthesis enzyme encoded by the eryCVI gene of Sac. erythraea (SEQ ID NO: 56) and the sugar biosynthesis enzymes encoded by the srmX gene of Streptomyces ambofaciens (Geistlich et al., Mol. Microbiol., 6:2019 (1992)), the rdmd gene of *Streptomyces purpurascens* (GenBank Accession: U10405) and the glycine methyltransferase of *Rattus norvegious* (Ogawa et al., *Eur. J. Biochem.* 168:141 (1987)) which are SEQ ID NOS:57, 58, and 59 respectively. A consensus sequence (SEQ ID NO:60) is also shown.

FIG. 6 illustrates the compounds conceivably formed in Examples 1–4 and are representative of compounds formed from Type I, Type II, and Type III alterations.

FIG. 7 illustrates the construction of the expression plasmid pASX2 described in Example 2. For FIGS. 7–13 the following abbreviations have been used: amp, ampicillin resistance gene; tsr, thiostrepton resistance gene; ROP, repressor of plasmid synthesis gene; eryBI, eryBII, eryBIII, eryBIV, eryBV, eryBVI, eryBVII, eryCI, eryCII, eryCIII, eryCIV, eryCV, and eryCVI, the erythromycin biosynthetic genes involved in the synthesis of mycarose or its attachment to the macrolide ring (eryb) or the synthesis of desosamine or its attachment to the macrolide ring (eryC) [the thin arrows above a gene indicate its relative size and the direction of transcription]; ori-*E. coli*, an origin of DNA replication that functions in *E. coli*, in the specific examples the ColE1 origin; ori-Stieptomyces, an origin of DNA replication that functions in Streptomyces, in the specific examples the pJV1 origin (Servin-Gonzalez et al., Microbiology, 141:2499 (1995)); p-ermE*, a modified promoter for the erythromycin resistance gene; t-fd, the gene VIII transcription terminator of bacteriophage fd; PCR, polymerase chain reaction. Restriction enzyme sites have been indicated by their standard commercial names (i.e. BamHI, EcoRI, etc). The abbreviations appended to the large arrows in the plasmid synthetic schemes summarize each of the steps involved the plasmid constructions. These steps are described fully in the relevant Examples.

FIG. 8 illustrates the construction of the eryBVII antisense expression plasmid pASBVII described in Example 2.

FIG. 9(A) illustrates the construction of the carrier plasmid pK 1.

DETAILED DESCRIPTION OF THE INVENTION

I. The Invention

Figure 1A:
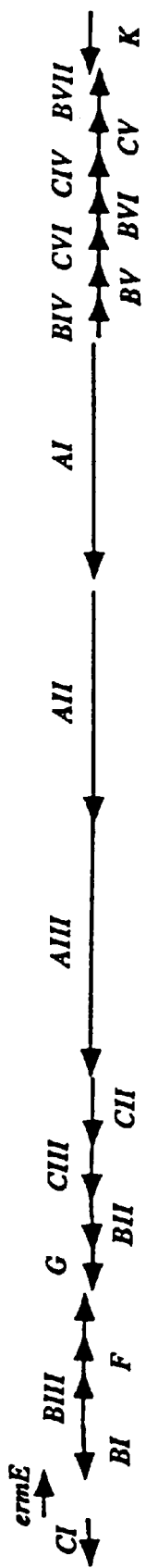
FIG. 1A) illustrates the organization of the erythromycin biosynthetic gene cluster and the genetic designations of the biosynthetic genes; B) illustrates an abbreviated erythromycin biosynthetic scheme that broadly associates the biosynthetic genes with their role in erythromycin biosynthesis. Seven eryB genes, eryBI–eryBVII, are responsible for the biosynthesis of L-mycarose or its attachment to the erythronolide B ring, and six eryC genes, eryCI–eryCVI, are responsible for the biosynthesis of D-desosamine or its attachment to 3-α-mycarosylerythronolide B. The dashed arrows indicate that the pathway through erythromycin B is not the principal natural biosynthetic route to erythromycin A.

The present invention provides isolated and purified polynucleotides that encode enzymes or fragments thereof responsible for the biosynthesis of polyketide-associated sugars or their attachment to polyketides, vectors containing those polynucleotides, host cells transformed with those vectors, a process of making novel glycosylated polyketides using those polynucleotides and vectors, and isolated and purified recombinant polypeptides and polypeptide fragments thereof.

II. Definitions

For the purposes of the present invention as disclosed and claimed herein, the following terms are defined.

The term "polyketide" as used herein refers to a large and diverse class of natural products, including but not limited to antibiotic, antifungal, anticancer, and anti-helminthic compounds. Antibiotics include, but are not limited to anthracyclines and macrolides of different types (polyenes and avermectins as well as classical macrolides such as erythromycins).

The term "glycosylated polyketide" refers to any polyketide that contains one or more sugar residues.

The term "glycosylation-modified polyketide" refers to a polyketide having a changed glycosylation pattern or configuration relative to that particular polyketide's unmodified or native state.

The term "polyketide-producing microorganism" as used herein includes any microorganism that can produce a polyketide naturally or after being suitably engineered (i.e. genetically). Examples of actinomycetes and the polyketides they naturally produce include but are not limited to those listed in Table 1 below (see Hopwood, D. A. and Sherman, D. H., *Annu. Rev. Genet.*, 24:37–66 (1990) incorporated herein by reference).

TABLE 1

| Organism | Polyketide Produced |
| --- | --- |
| *Saccharopolyspora erythraea* | Erythromycin |
| *Streptomyces ambofaciens* | Spiramycin |
| *Streptomyces avermitilis* | Avermectin |
| *Streptomyces fradiae* | Tylosin |
| *Streptomyces griseus* | Candicidin, monactin, griseusin |
| *Streptomyces violaceoniger* | Granaticin |
| *Streptomyces thermotolerans* | Carbomycin |
| *Streptomyces rimosus* | Oxytetracycline |
| *Streptomyces peucetius* | Daunorubicin |
| *Streptomyces coelicolor* | Actinorhodin |
| *Streptomyces glaucescens* | Tetracenomycin |
| *Streptomyces roseofulvus* | Frenolicin |
| *Streptomyces cinnamonensis* | Monensin |
| *Streptomyces curacoi* | Curamycin |
| *Amycolatopsis mediterranei* | Rifamycin |

Other examples of polyketide-producing microorganisms that produce polyketides naturally include various Actinomadura, Dactylosporangium and Nocardia strains.

The term "sugar biosynthesis genes" as used herein refers to sequences of DNA from *Saccharopolyspora erythraea* that encode sugar biosynthesis enzymes and is intended to include sequences of DNA from other polyketide-producing microorganisms which are identical or analogous to those obtained from *Saccharopolyspora erythraea*.

The term "sugar biosynthesis enzymes" as used herein refers to polypeptides which are involved in the biosynthesis and/or attachment of polyketide-associated sugars and their derivatives and intermediates.

The term "polyketide-associated sugar" refers to a sugar that is known to attach to polyketides or that can be attached to polyketides by the processes described herein.

The term "sugar derivative" refers to a sugar which is naturally associated with a polyketide but which is altered relative to the unmodified or native state; examples only include N-3-α-desdimethyl D-desosamine, D-mycarose, 4-keto-L-mycarose, 4keto-D-mycarose, 3-desmethyl L-mycarose and 3-desmethyl D-mycarose.

The term "sugar intermediate" refers to an intermediate compound produced in a sugar biosynthesis pathway.

The term "eryB" as used herein refers to sequences of DNA that encode enzymes involved specifically in the biosynthesis of the deoxysugar L-mycarose.

The term "eryC" as used herein refers to sequences of DNA that encode enzymes involved specifically in the biosynthesis of the deoxysugar D-desosamine.

III. Polynucleotides

The organization of the segment of the *Saccharopolyspora erythraea* (*Sac. erythraea*) chromosome that determines the biosynthesis of erythromycin and the corresponding genes that determine the biosynthesis of the sugars L-mycarose and D-desosaniine, designated eryB and eryC, respectively, are shown in FIG. 1A. It is seen that several genes are required for the biosynthesis of each of the sugars and that these genes are interspersed among one another. It is predicted that each gene encodes an enzyme that catalyzes one or a few steps in the biosynthesis of L-mycarose or D-desosarmine from thymidine diphospho-4-keto-6 deoxyglucose (TDP-glucose); these steps are outlined in FIG. 2 and FIG. 3. In the case of L-mycarose, (shown in FIG. 2), these steps include: (1) C-2" deoxygenation, (2) C-2"/C-3" enoyl reduction, (3) C-5" epimerization, (4) C-3" C-methylation, (5) C-4" keto reduction, and (6) transfer to erythronolide B. For D-desosamine, shown in FIG. 3, these steps comprise (1) C-4'/3' isomerization, (2, 3) C-3' deoxygenation and reduction, (4) C-3' amination, (5, 6) N-3' N-dimethylation, and transfer to mycarosyl erythronolide B.

This classification of genes (as belonging to either the eryB class or eryC class) was determined by first altering the wild type genes of interest in an erythromycin producing strain (i.e. in vivo) to inactivate their expression. The erythromycin products resulting from such alterations were then analyzed. Genes whose alterations caused an accumulation of erythronolide B (indicating a lack of L-mycarose, or failure to attach L-mycarose to the erythronolide ring) were classified as eryB genes; genes whose alterations caused an accumulation of 3-α-L-mycarosyl erythronolide B (indicating a lack of D-desosamine, or failure to attach D-desosamine to the 3-α-L-mycarosyl erythronolide B ring) were classified as eryC genes. Accordingly, it should be noted that all such genes identified herein as eryB or eryC are involved in the synthesis of L-mycarose or D-desosamine. The predicted functional activities of the polypeptides encoded by eryB and eryC will be discussed in further detail below.

In one aspect then, the present invention provides isolated and purified eryB and eryC polynucleotides from *Sac. erythraea* that encode enzymes involved in the production of glycosylated polyketides. A polynucleotide of the present invention that encodes a sugar biosynthesis enzyme is an isolated single or double stranded polynucleotide having a nucleotide sequence which comprises a nucleotide sequence selected from the group consisting of (a) the sense sequence of FIG. 4A from about nucleotide position 54 to about nucleotide position 1136; the sense sequence of FIG. 4A from about nucleotide position 1147 to about nucleotide position 2412; the sense sequence of FIG. 4A from about nucleotide position 2409 to about nucleotide position 3410; the sense sequence of FIG. 4B from about nucleotide position 80 to about nucleotide position 1048; the sense sequence of FIG. 4B from about nucleotide position 1048 to about nucleotide position 2295; the sense sequence of FIG. 4B from about nucleotide position 2348 to about nucleotide position 3061; the sense sequence of FIG. 4B from about nucleotide position 3214 to about nucleotide position 4677; the sense sequence of FIG. 4B from about nucleotide position 4674 to about nucleotide position 5879; the sense sequence of FIG. 4B from about nucleotide position 5917 to about nucleotide position 7386; and the sense sequence of FIG. 4B from about nucleotide position 7415 to about nucleotide position 7996;

(b) sequences complementary to the sequences of (a), (c) sequences that, when expressed, encode polypeptides encoded by the sequences of (a), and (d) analogous sequences that hybridize under stringent conditions to the sequences of (a).

A preferred polynucleotide is a DNA molecule. In another embodiment, the polynucleotide is an RNA molecule.

The nucleotide sequence and deduced amino acid residue sequences of the sugar biosynthesis genes are set forth in FIGS. 4A and 4B. The nucleotide sequences of FIG. 4A and FIG. 4B represent full length DNA clones of the sense strand of two distinct clusters of sugar biosynthesis genes and are intended to represent both the sense strand (shown on top) and its complement.

The present invention also contemplates analogous DNA sequences which hybridize under stringent hybridization conditions to the DNA sequences set forth above. Stringent hybridization conditions are well known in the art and define a degree of sequence identity greater than about 80%–90%. The modifier "analogous" refers to those nucleotide sequences that encode analogous polypeptides (i.e. in relation to a sugar biosynthesis enzyme), analogous polypeptides being those which have only conservative differences and which retain the conventional characteristics and activities of sugar biosynthesis enzymes. (A more detailed description of analogous polypeptides is provided below). The present invention also contemplates naturally occurring allelic variations and mutations of the DNA sequences set forth above so long as those variations and mutations code, on expression, for a sugar biosynthesis gene of this invention as set forth hereinafter.

As is well known in the art, because of the degeneracy of the genetic code, there are numerous other DNA and RNA molecules that can code for the same polypeptides as those encoded by the aforementioned sugar biosynthesis genes and fragments thereof. The present invention, therefore, contemplates those other DNA and RNA molecules which, on expression, encode the polypeptides of SEQ ID NOs:3–10 or fragments thereof. Having identified the amino acid residue sequence encoded by a sugar biosynthesis gene, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid, are within the scope of this invention.

A table of amino acids and their representative abbreviations, symbols and codons is set forth below in Table 2.

TABLE 2

| Amino Acid | Abbrev. | Symbol | Codon(s) | | | |
|---|---|---|---|---|---|---|
| Alanine | Ala | A | GCA | GCC | GCG | GCU |
| Cysteine | Cys | C | UGA | UGU | | |

TABLE 2-continued

| Amino Acid | Abbrev. | Symbol | Codon(s) | | | | |
|---|---|---|---|---|---|---|---|
| Aspartic Acid | Asp | D | GAC | GAU | | | |
| Glutamic Acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG* CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

As is well known in the art, codons constitute triplet sequences of nucleotides in mRNA molecules and as such, are characterized by the base uracil (U) in place of base thymidine (T) (which is present in DNA molecules).

A simple change in a codon for the same amino acid residue within a polynucleotide will not change the structure of the encoded polypeptide. By way of example, it can be seen from FIG. 4A that an AGC codon for serine exists at nucleotide positions 126–128 and again at positions 420–422 and 561–563. However, it can also be seen from that sane sequence that serine can be encoded by a TCG codon (see eg. nucleotide positions 192–194) and a TCC codon (see e.g., nucleotide positions 204–206). Substitution of the latter codons for serine with the AGC codon for serine, or visa versa, does not substantially alter the DNA sequence of FIG. 4A and results in production of the same polypeptide. In a similar manner, substitutions of the recited codons with other equivalent codons can be made in a like manner without departing from the scope of the present invention.

A polynucleotide of the present invention can also be an RNA molecule. An RNA molecule contemplated by the present invention is complementary to or hybridizes under stringent conditions to any of the DNA sequences set forth above. Exemplary and preferred RNA molecules are MRNA molecules that encode sugar biosynthesis enzymes of this invention.

IV. Polypeptides

In another aspect, the present invention provides polypeptides which are sugar biosynthesis enzymes. A sugar biosynthesis enzyme of the present invention is a polypeptide of about 21 kdal to about 47 kdal. As set forth in FIG. 5(A)–5(E), analogs of the predicted polypeptides encoded by certain eryB and eryC genes have been identified in various species and their sequences compared using the PREM routine (Genetics Computer Group (GCG) Sequence Analysis Software Package, Madison, Wis.). Due to the degree of amino acid sequence identity existing between the polypeptides of these other sugar biosynthesis genes and the polypeptides encoded by the eryB and eryC genes, certain enzymatic activities can reasonably be attributed to the eryB and eryC polypeptide&

By way of example, analogs of the polypeptide encoded by the eryBIV gene have been identified in *Yersinia pseudotuberculosis, Salmonella enterica, Streptomyces griseus* and *Escherichia coli* (see FIG. 5(A)). The various analogs have been identified with from 290–328 amino acid residues and are characterized by a low degree of amino acid sequence identity. (For example, the identity between the sugar biosynthesis enzyme encoded by the eryBIV gene of *Sac. erythraea* and the sugar biosynthesis enzyme encoded by the galE gene of *E. coli* is 20% at the amino acid level). However, a conserved amino acid sequence motif, G x x G x x G (where G represents the amino acid glycine and x represents any other amino acid residue) is found within the first 30 amino acid residues of all analogs shown. Since the polypeptide encoded by the galE gene has been shown to be an epimerase (whose mechanism includes a ketoreduction (Bauer et al., *Proteins* 12:372 (1992)), the eryBIV gene product is reasonably predicted to be a ketoreductase. See FIG. 2.

As set forth in FIG. 5(B) analogs of the sugar biosynthesis enzyme encoded by the eryBVII gene have been identified in *Streptomyces griseus, Salmonella enterica, Yersinia entercolitica* and *Yersinia pseudotuberculosis*. The various analogs have been identified with from 183–200 amino acid residues and are characterized by a moderate degree of amino acid identity. By way of example, the identity at the amino acid level between the sugar biosynthesis enzyme encoded by the eryBVII gene of *Sac. erythraea* and the sugar biosynthesis enzyme encoded by the rfbC gene of *Salmonella enterica* or the strM gene of *Streptomyces griseus* is 37% and 61%, respectively. Furthermore, a common characteristic of these particular polypeptides (including that of eryBWII), is that they are only associated with L-sugar biosynthesis and not with D-sugar biosynthesis. Thus the gene product of eryBVII is reasonably predicted to function as a C-5 epimerase which converts the stereochemistry of the sugar from the "D" configuration to the "L" configuration.

As set forth in FIG. 5(C) analogs of the sugar biosynthesis enzyme encoded by the eryCIV gene have been identified in *Sac. erythraea* and *Yersinia pseudotuberculosis*. As set forth in FIG. 5(C), the predicted amino acid sequences of the protein products of eryCI and eryCIV share 34% sequence identity to each other and 27% and 25% respectively to the predicted amino acid sequence encoded by ascC from *Yersinia pseudotuberculosis*. The enzyme encoded by ascC has been shown to remove a hydroxyl group located at the C-3 position of L-ascarylose (Liu and Thorson, *Annu. Rev. Microbiol.* 48:223 (1994)). Thus, at least one of the polypeptides encoded by eryCI or eryCIV is predicted to be an enzyme which functions in deoxygenation reactions.

Furthermore, the enzyme encoded by the ascC gene requires the biochemical cofactor pyridoxamine, which is the same cofactor used in biochemical transamination reactions. Consequently, it has been proposed that some protein analogs having a moderate degree of sequence similarity to the polypeptide encoded by ascC function as transaminases in amino sugar biosynthesis (Thorson et al., *J. Am. Chem. Soc.* 115:6993 (1993)). Since the biosynthesis of D-desosamine requires both deoxygenation and transamination, it is reasonable to predict that at least one of the polypeptides encoded by the eryCI or eryCIV genes functions in transamination reactions.

Figure 2:
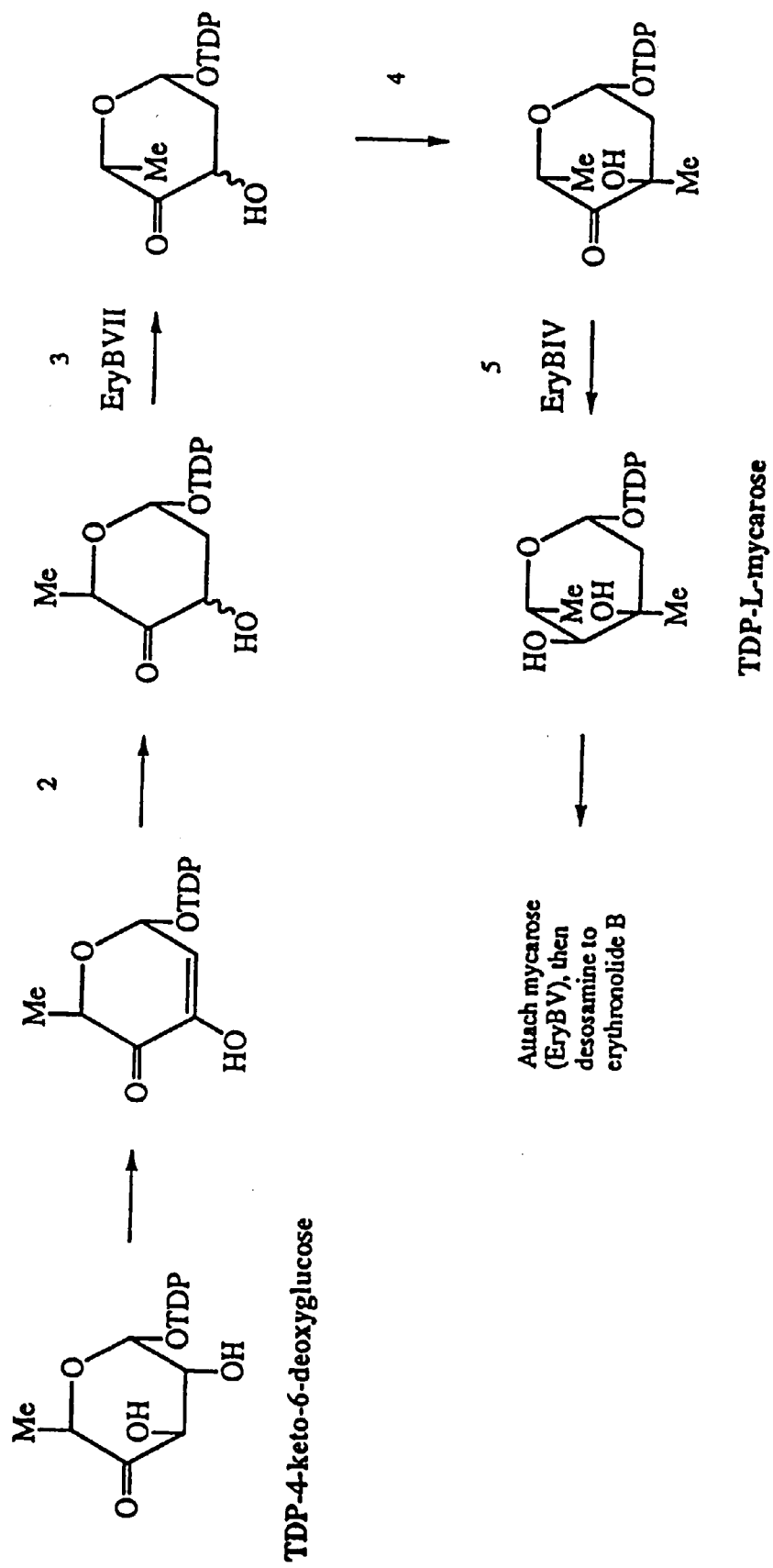
FIG. 2 illustrates the proposed scheme for the biosynthesis of L-mycarose and the eryB genes responsible for the specific steps.
Figure 3:
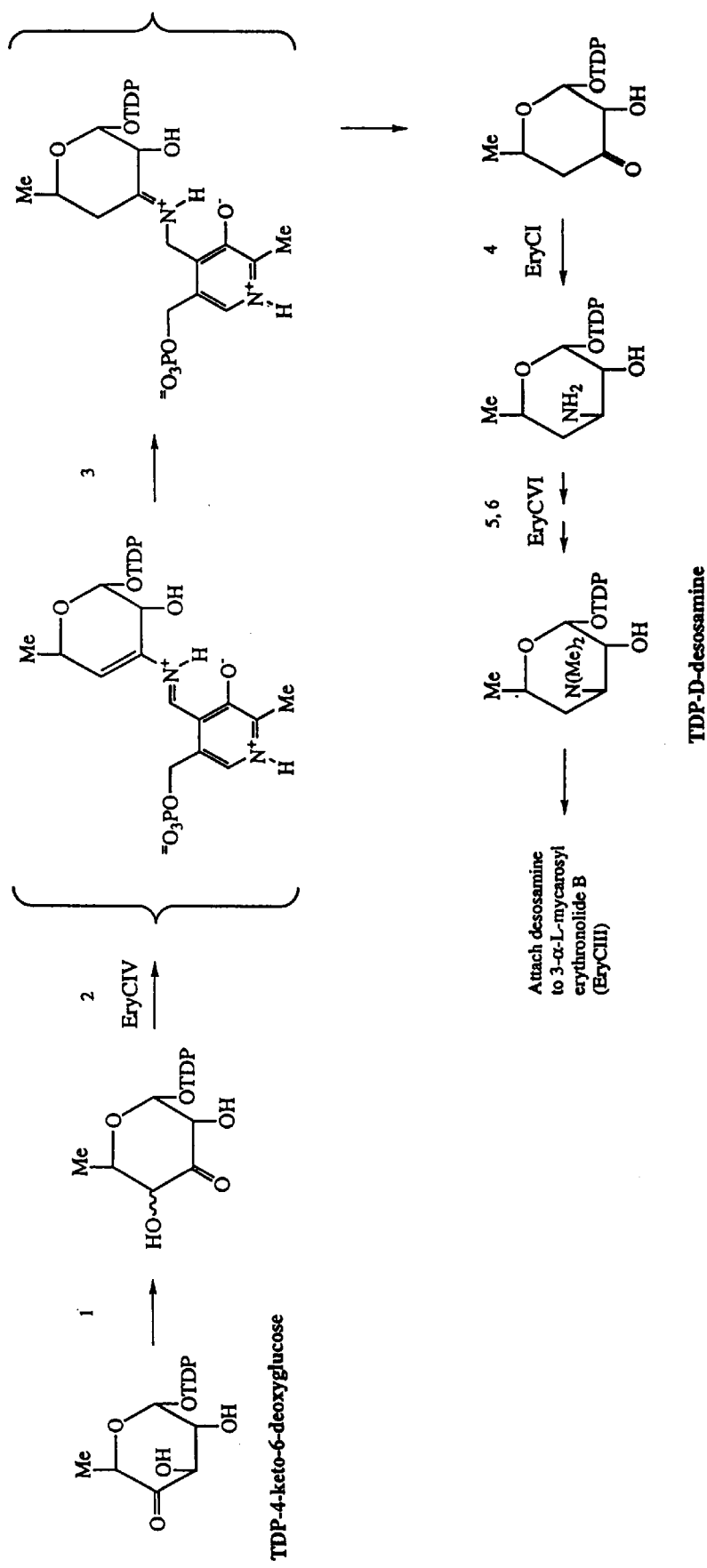
FIG. 3 illustrates the proposed scheme for the biosynthesis of D-desosamine and the eryC genes responsible for the specific steps. 5857.US.01 *
Figure 6A:
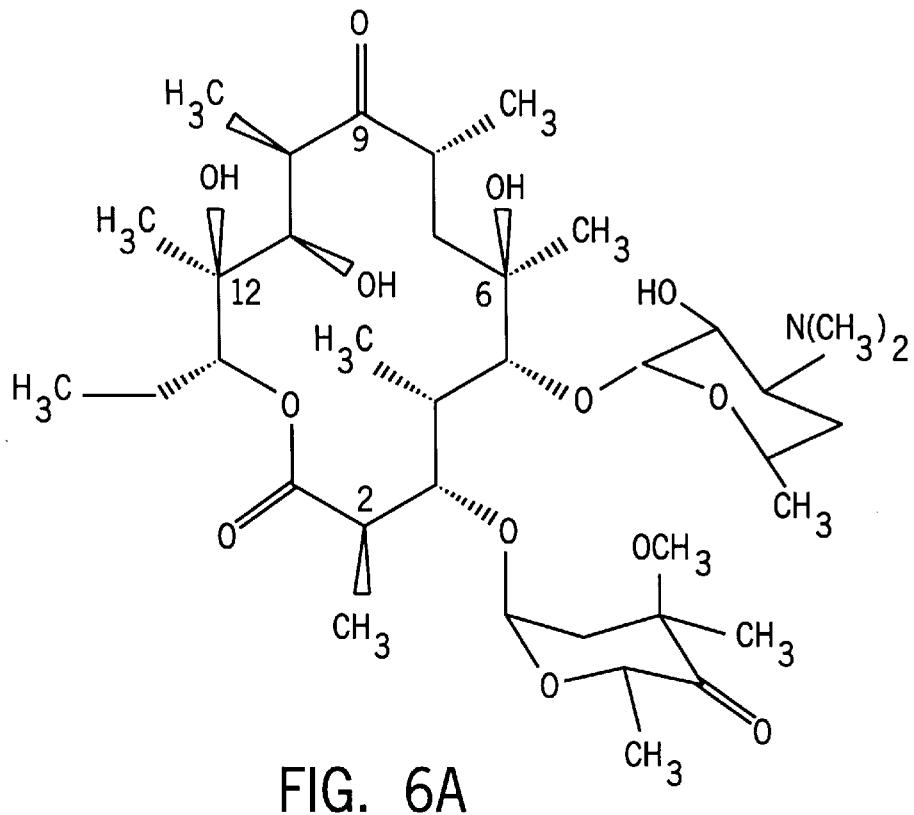
Figure 6B:
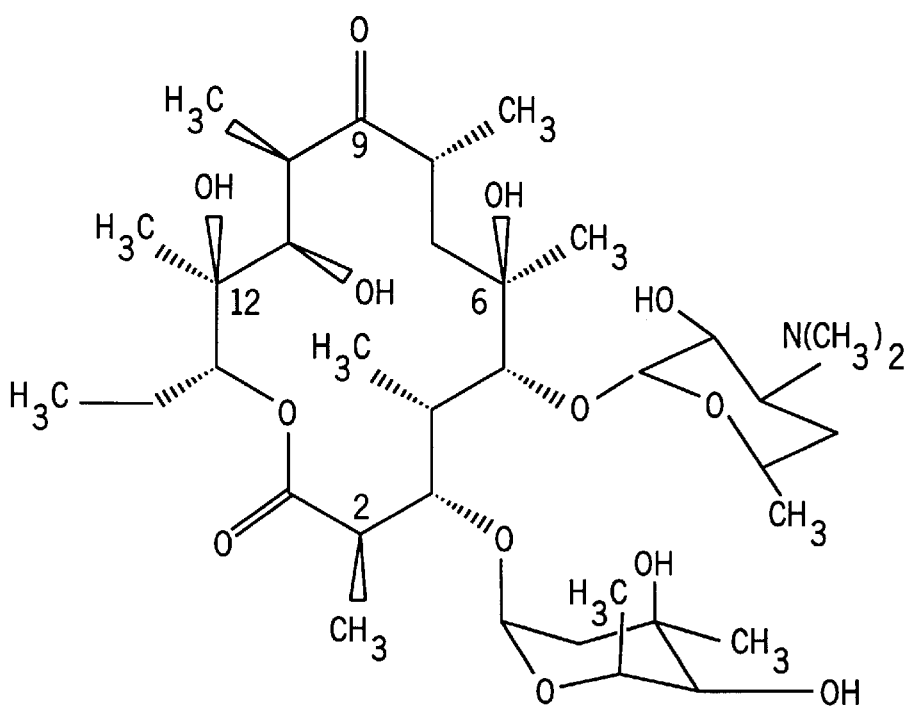
Figure 6C:
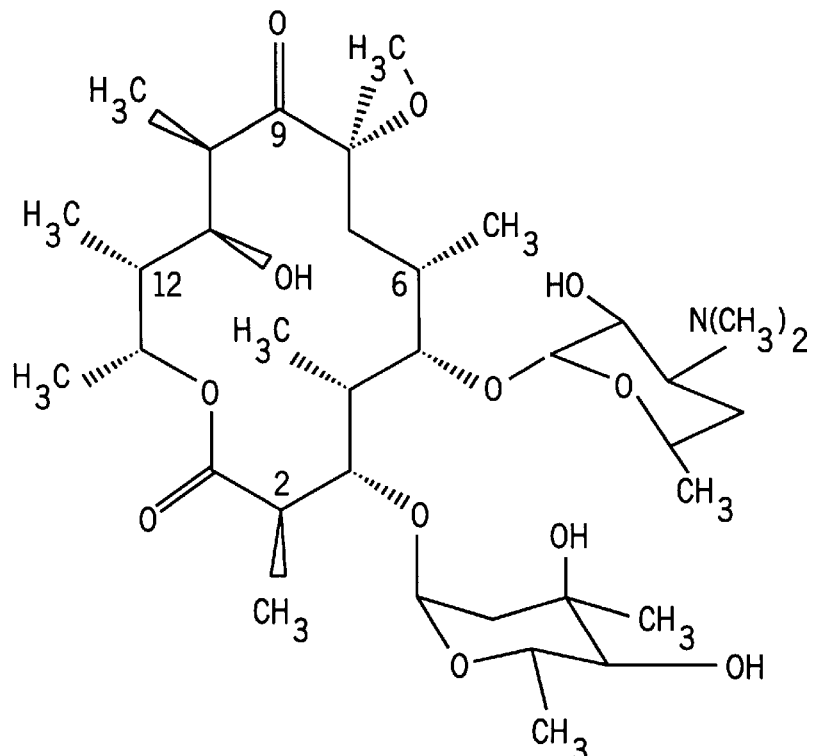
Figure 6D:
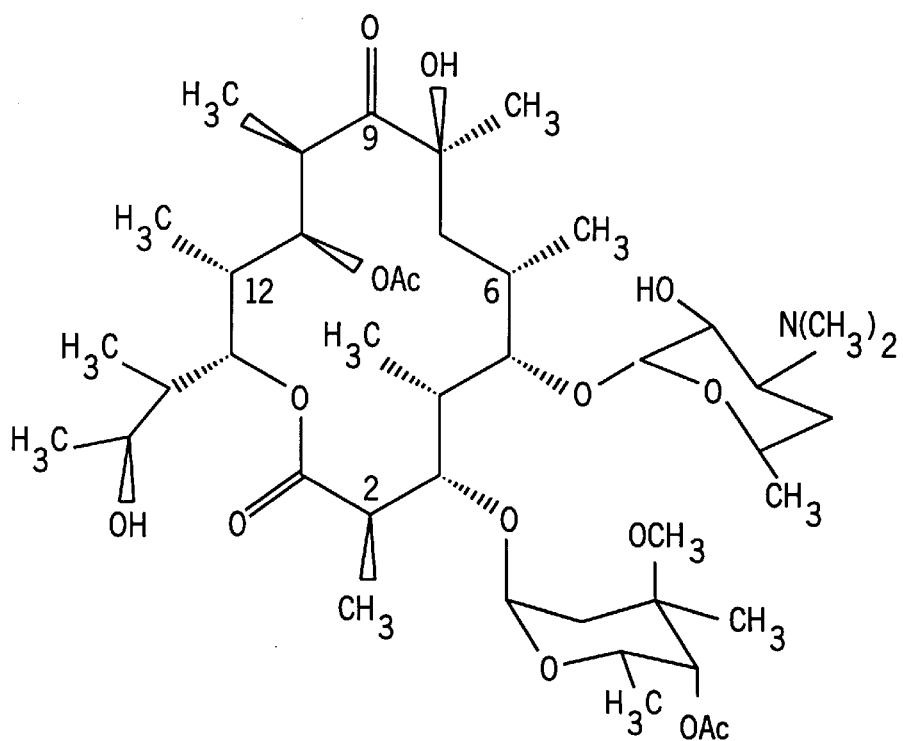

As set forth in FIG. 5(D) the predicted polypeptides encoded by eryBV and eryCIII share 43% identity at the amino acid level and as such, may be assumed to have similar activities with respect to their particular sugars. However, as shown in FIGS. 2 and 3, there are no common steps in the proposed pathways of L-mycarose and D-desosamine biosynthesis. Rather than having similar sugar biosynthesis functions, these polypeptides are predicted to be nucleotidyl-sugar transferases which, (in *Sac. erythraea* at least), function to attach L-mycarose and D-desosamine to erythronolide B and 3-α-mycarosylerythronolide B, respectively.

As set forth in FIG. 5(E) analogs of the polypeptide encoded by the eryCVI gene have been identified in *Streptomyces ambofaciens, Steptomyces purpurascens,* and *Rattus norvegicus*. The various analogs have been identified with from 237–293 amino acid residues and are characterized by a low to moderate degree of amino acid identity. By way of example, the identity between the polypeptide encoded by the eryCVI gene of *Sac. erythraea* and the glycine methyltransferase of *Rattus norvegicus* is 26% at the amino acid level. Furthermore these sugar biosynthesis enzymes share a common sequence motif, LDVCGTG (see amino acid positions 64–71 in the consensus sequence in FIG. 5(E)), with rat glycine methyltransferase whose biochemical function is known (Ogawa et al., *Eur. J. Biochem.* 168:141 (1987)). Thus these polypeptides are predicted to be N-methyltransferases.

In another aspect, the present invention provides a recombinant C4" keto reductase from *Sac. erythraea*. A recombinant *Sac. erythraea* C-4" ketoreductase of the present invention is a polypeptide of about 322 or less amino acid residues. A preferred recombinant *Sac. erythraea* C-4" ketoreductase is that encoded by the nucleotide sequence of FIG. 4B from about nucleotide position 80 to about nucleotide position 1048.

The present invention also contemplates amino acid residue sequences that are substantially duplicative of the sequences set forth herein such that those sequences demonstrate like biological activity to disclosed sequences. Such contemplated sequences include those analogous sequences characterized by a minimal change in amino acid residue sequence or type (e.g., conservatively substituted sequences) which insubstantial change does not alter the fundamental nature and biological activity of the aforementioned sugar biosynthesis enzymes.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2(0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minrus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

V. Production of novel glycosylated polyketides

In another aspect, the present invention comprises a general procedure for producing novel polyketide structures in vivo by selectively altering, inactivating, or augmenting the genetic information of the organism that naturally produces a related polyketide. That is, in the present invention, novel polyketides of desired structure are produced by manipulation of the eryB and/or eryC genes followed by their introduction into various polyketide-producing microorganisms. These manipulations result in the formation of "glycosylation-modified" polyketides (i.e. polyketides having an altered glycosylation pattern or configuration relative to their native state). For example, "glycosylation-modified" polyketides are those which have additional sugar groups attached (where none previously existed), different sugars (such as sugar intermediates) attached (in place of the natural sugars) or lack sugar groups (at positions where sugar groups previously existed).

In the case of Type I and Type II alterations (further described below) glycosylation-modified polyketides may arise though mechanisms which cause either (1) the non-production of the sugar attachment enzyme (i.e. the enzyme involved in attachment of a sugar to the the polyketide structure) or (2) the non-production of a sugar biosynthesis enzyme. In the first instance, the sugar will not be attached to the polyketide since the enzyme which functions to attach the sugar will be lacking. In the second situation, a sugar intermediate from the biosynthesis pathway will be produced (depending on which enzyme is lacking) and attached to the polyketide provided it is recognized as a suitable substrate by the sugar attachment enzyme; alternatively, it will not be recognized and therefore, not attached. In the case of Type III alterations (also described in detail below), glycosylation-modified polyketides arise via attachment of additional or different sugars (i.e. not normally found in a particular polyketide-producing strain) to the polyketide. It should be noted, that these postulated mechanisms are simply provided to enhance understanding of the novel processes described herein; the actual mechanisms by which the Type I, II and III alterations produce glycosylation-modified polyketides is not presently known.

In the first type of alteration (referred to herein as Type I alterations), genetically altered eryB and/or eryC genes are introduced into the chromosome of *Sac. erythraea* or another glycosylated polyketide-producing organism that also produces L-mycarose, D-desosamine, or their closely related derivatives such as mycaminose (4hydroxy D-desosamine). The genetic alteration of an eryB and/or eryC gene is such that it causes a non-functional enzyme to be synthesized. Once introduced into an appropriate strain, the altered gene replaces its corresponding wild type gene causing the strain to lose the ability to produce a particular enzymatic activity involved in sugar biosynthesis. As a result, a glycosylation-modified polyketide is produced via either of the mechanisms previously described for a Type I alteration.

In a Type I change described herein, a specific mutation in an eryB and/or eryC gene of the *Sac. erythraea* chromosome is accomplished by a three step process which involves: 1) specifically altering the DNA sequence of a desired sugar biosynthesis gene, 2) subcloning the altered sequence into a suitable vector capable of recombining in the chromosome of an appropriate host and 3) introducing the vector containing the subcloned sequence into the appropriate host so that exchange of the wild type allele with the mutated one will occur. The first step is accomplished using standard recombinant DNA techniques to effect a deletion, base pair conversion or frame-shift in the DNA sequence. The second step, which also employs standard recombinant techniques, involves subcloning the altered sequence into a vector which does not replicate in *Sac. erythraea* or the desired host. In the final step, the vector is introduced into a suitable host, where by the process of gene replacement, the altered allele replaces the wild-type one. All techniques employed in a Type I change are well known to those of ordinary skill in the art.

Example 1 illustrates the process of gene replacement of an eryB gene. As Example 1 shows, the eryb gene of interest is mutated and along with adjacent upstream and downstream DNA sequences, cloned into a non-replicating *Sac. erythraea* plasmid vector. The vector carrying the mutated allele and adjoining DNA is then introduced into the host strain by the process of protoplast transformation. Transformants are regenerated under selective conditions (i.e. conditions that require expression of a particular plasmid marker) in order to induce recombination of the plasmid into the host cell chromosome. In other words, since the plasmid does not replicate autonomously, it must reside in the chromosome to be maintained in the cell and to express a particular marker under selective conditions. Insertion is achieved when the regenerated cells undergo a single homologous recombination between one of the two DNA segments that flank the mutation on the plasmid and its homologous counterpart in the chromosome. The cells are then grown without selection for the marker which induces plasmid loss from the chromosome. This loss arises after the cells have undergone a second recombination between the second DNA segment that flanks the mutation and its homologous chromosomal counterpart. This second recombinational event results in the loss of the plasmid sequences and the wild type allele from the chromosome; the mutant allele however is retained.

In a variation of a Type I change, the non-production of the sugar biosynthesis enzyme (or attachment enzyme) may be achieved by the alternative mechanisms of promoter inactivation and/or transcriptional terminator insertion. These variations do not effect the gene sequence itself but rather regulatory mechanisms involved in gene transcription. "Promoter" as used herein refers to that region of a DNA molecule which controls the initiation of RNA transcription. Such regions are known to bind RNA polymerases (i.e. the enzymes involved in synthesizing RNA molecules).

This form of Type I change (i.e. promoter inactivation) involves two steps of 1) identifying the promoter region of the desired gene and 2) rendering the promoter region inoperable by mutation. As in the replacement mechanism described above such mutations may be effected by creating deletions in the promoter sequence or by base pair conversion. In the case where the promoter controls transcription of a single gene, inactivation of the promoter will eliminate expression of that particular gene; of course, where the promoter controls expression of an entire operon (i.e. a series of genes whose expression is controlled by a single promoter), promoter inactivation will effectively eliminate expression of all genes in that operon.

In a similar manner, the non-production of a sugar biosynthesis enzyme (or attachment enzyme) may arise from inserting a transcriptional terminator upstream from the gene to be inactivated. A "transcriptional terminator" as used herein is a nucleotide sequence which signals RNA polymerase to cease transcription. An example of a transcriptional terminator is a palindromic sequence capable of forming a stem-loop structure that is followed by a stretch of U residues (for example the transcriptional terminator that follows gene VIII of bacteriophage fd (Beck and Zink, *Gene*, 16:35 (1981)). Effecting a change in production of a sugar biosynthesis gene by this process involves 1) identifying of the gene or genes of interest (in the case of an operon arrangement) to be inactivated and 2) cloning a transcriptional terminator sequence in a region of the DNA upstream from such gene(s). A transcriptional terminator will cause the polymerase involved in RNA transcription to stop (at or near the signaling region) thereby preventing transcription of any downstream sequences. Thus, changes such as promoter inactivation and transcriptional insertion, which directly effect expression of sugar biosynthesis genes are also intended to be within the scope of the invention.

In the second case (referred to herein as Type II alterations) eryB and/or eryC genes are arranged on a vector in an antisense orientation relative to a promoter capable of allowing expression of the gene in *Sac. erythraea or Streptomyces*. The vector is then introduced into a polyketide producing microorganism. As a result of this vector construction, antisense messenger RNA (mRNA) is produced which interferes with the translation of the wild-type mRNA. Similarly to the Type I manipulation, novel glycosylation modified polyketides will be produced in which the normal mycarose, desosamine, and/or closely related sugar residue is lacking or is substituted by a sugar intermediate.

In a Type II change, inactivation of the eryB and/or eryC genes by antisense expression is accomplished by a two step procedure in which (1) a specific sugar biosynthesis gene is subcloned into an expression vector in an antisense (i.e. reverse) orientation; and (2) the anti-sense expression vector is introduced into the desired strain. The first step is accomplished using standard recombinant DNA techniques employing either *E. coli* or Streptomyces as the host, and an expression vector (capable of replicating in either host) that can be assembled to contain a Streptomyces promoter. Streptomyces promoters may be obtained from any commercially available Streptomyces plasmids or Streptomyces-*E. coli* shuttle plasmids. In step 2, the anti-sense expression vector is introduced into a suitable Streptomyces strain and the transformed cells are grown under selective conditions in order to maintain the expression palsmid in the cell.

Figure 1B:
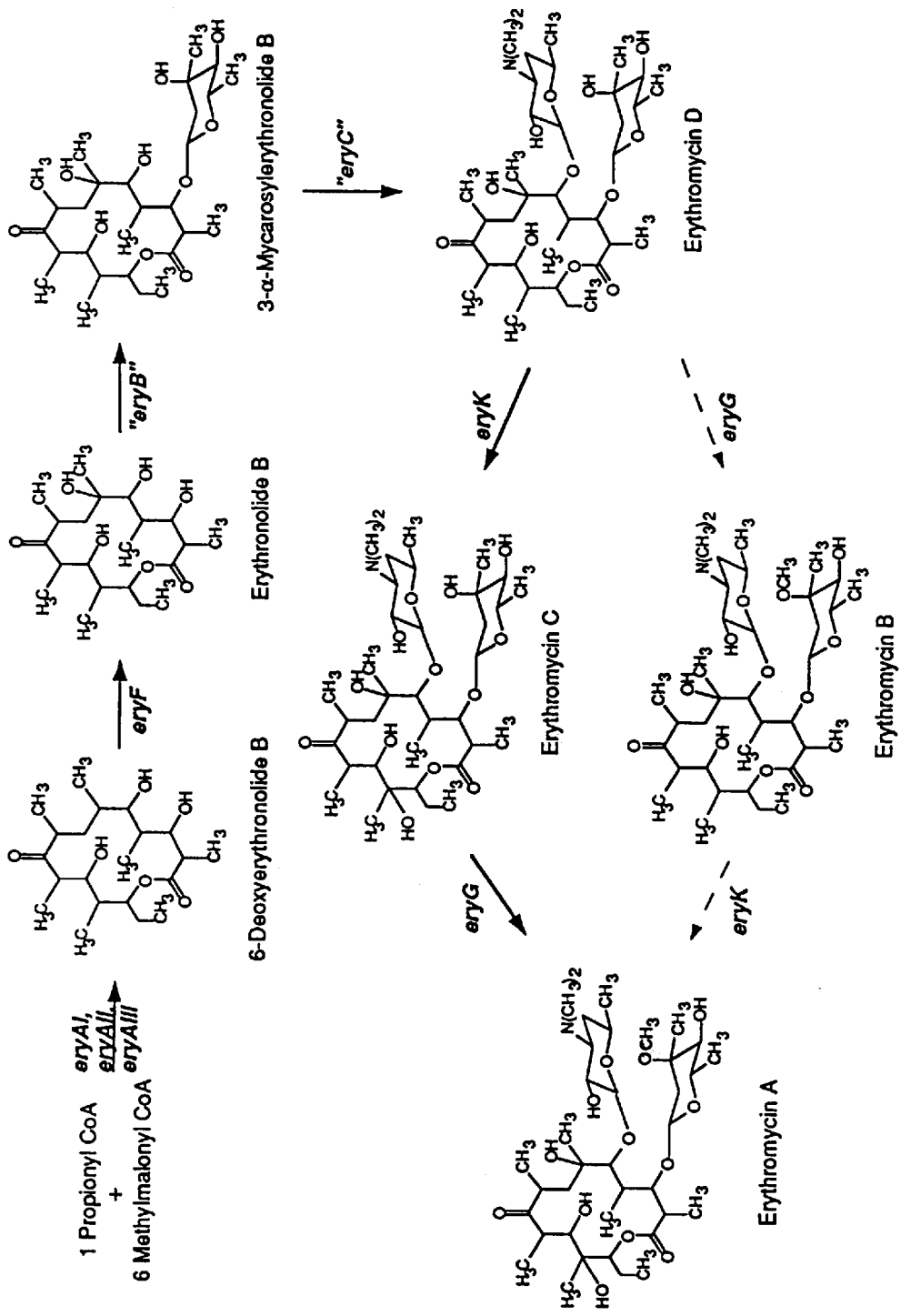

As described in Example 2, the gene to be inactivated is subcloned in its reverse orientation downstream of a Streptomyces promoter (which is contained within a replicating *Sac. erythraea* plasmid). The plasmid carrying the antisense gene is then introduced into the host strain by protoplast transformation. Transformants are regenerated under selective conditions in order to maintain the autonomously replicating plasmid in the cells. Subsequent expression of the antisense gene causes the production of an antisense messenger RNA (mRNA) that is complementary to the mRNA of the native allele of the selected gene. Through standard nucleotide base pair interactions, the antisense mRNA and the native mRNA form an RNA duplex that occludes the ribosome binding site of the native mRNA. This interaction prevents ribosomal translation of the native mRNA and the corresponding synthesis of the enzyme encoded by that mRNA. In this way, specific enzymatic steps in sugar biosynthesis corresponding to the identity of the gene expressed in the antisense orientation are blocked leading to the production of novel sugar intermediates which, when attached to the polyketide ring of the host microorganism, give rise to novel glycosylation-modified polyketides. Alternatively, the antisense expression vector can be constructed using a non-replicating Sac. erythraea vector that includes flanking DNA from a nonessential region of the Sac. erythraea chromosome, such as the region immediately upstream from the eryK gene (FIG. 1). This vector can then be used to stably insert the antisense construction into the chromosome by homologous recombination in a fashion similar to that described for the construction of a Type I alteration.

In the third case (referred to herein as Type m alterations), novel glycosylation-modified polyketides of desired structure are produced by arranging all or a subset of the eryB and/or eryC genes on a replicating vector and introducing these genes en bloc into a "distinct" polyketide-producing organism, ie. one other than the microorganism from which the eryB and/or eryC genes were taken. As an example, eryB and/or eryC genes may be taken from Sac. erythreae and introduced into Streptomyces violaceoniger or Streptomyces venezuelae. In this case, mycarose, desosamine, their biochemical intermediates and/or their closely related derivatives will be synthesized and attached at specific positions to polyketide compounds that do not necessarily carry these, or any, sugar residues. Some examples of novel glycosylated polyketides that may be produced in hosts that carry such manipulations are shown in FIG. 6.

In Type m changes, the genes for the biosynthesis of mycarose and/or desosanmine are introduced into a polyketide-producing organism other than Sac. erythraea by another simple two step procedure: 1) all or a subset of the eryB and/or eryC genes are assembled together on a replicating plasmid downstream of a Streptomyces promoter; and 2) the plasmid is introduced into the polyketide-producing organism. Step 1 requires standard recombinant DNA manipulations employing E. coli and/or Streptomyces as the host Step 2 requires one or more plasmids out of the several Streptomyces vectors or E. coli-Streptomyces shuttle vectors available, one or more promoters that function in Streptomyces, and a selection for the presence of the strain carrying the plasmid. As described in Examples 3 and 4, sets of the eryB and/or eryC genes are sequentially subcloned together on a replicating vector downstream of a suitable promoter that functions in the desired host. The plasmid carrying the grouped genes is then introduced into the host strain by electroporation or by transformation of protoplasts employing selection for a plasmid marker.

GENERAL METHODS

Materials, Plasmids, and Bacterial Strains

Restriction endonucleases, T4 DNA ligase, competent E. coli DH5α cells, X-gal, IPTG and plasmids pUC18, pUC19, and pBR322 were purchased from Bethesda Research Laboratories (BRL), Gaithersburg, Md. Vent$_R$® DNA polymerase was purchased from New England Biolabs (Beverly, Mass.). Plasmids pGEM®5Zf, pGEM®7Zf, and pGEM®11Zf were from Promega, Madison, Wis., plasmids pIJ4070 and pIJ702 were obtained from the John Innes Institute, Norwich, England, and plasmids pWHM3 and pWHM4 (J. Bacteriol. 1989 171:5872) were obtained from C. R. Hutchinson, University of Wisconsin, Madison, Wis. [α-$^{32}$P]dCTP, Hybond™-N nylon membranes, and Megaprime nick translation kits were from Amersham Corp., Chicago, Ill. SeaKem® LE agarose and SeaPlaque® low gelling temperature agarose were from FMC Bioproducts, Rockland, Me. E. coli K12 strains carrying the E. coli-Sac. erythraea shuttle plasmids pWHM3 and pWHM4 (Vara et al., J Bacteriol, 171:5872 (1989)) and PAWX are available from the Agricultural Research Service, Peoria, Ill., under the accession numbers NRRL B-21512, NRRL B-21513 and NRRL B-21514, respectively. Sac. erythraea strain NRRL2338 is also available from the Agricultural Research Service culture collection. Staphylococcus aureus Th$^R$ (thiostrepton resistant) was obtained by plating $10^8$ cells of S. aureus on agar medium containing 10 μg/ml thiostrepton and picking a survivor after 48 hr growth at 37° C. Thiostrepton was obtained from Sigma Chemical, St Louis, Mo. All other chemicals and reagents were from standard commercial sources unless otherwise specified.

DNA Manipulations

Standard conditions were employed for restriction endonuclease digestion, agarose gel-electrophoresis, isolation of DNA fragments from low melting agarose gels, DNA ligation, plasmid isolation from E. coli by alkaline lysis, and transformation of E. coli employing selection for ampicillin resistance (150 μg/ml) on LB agar plates (Sambrook et al., Molecular Cloning, A Laboratory Manual, Cold Spring Harbor Laboratory Press, Plainview, N.Y., 1989). Total DNA from Sac. erythraea and Streptomyces species (including S. fradiae, S. celestes, S. violaceoniger, S. hygroscopicus, S. venezuelae) was prepared according to described procedures (Hopwood et al., Genetic Manipulation of Streptomyces, A Laboratory Manual, John Innes Foundation, Norwich, UK (1985)). Transfer of DNA from agarose gels to Hybond™-N membranes and Southern analysis using Megaprime™ nick translated probes was performed according to the manufacturers instructions.

Amplification of DNA Fragments

Synthetic deoxyoligonucleotides were synthesized on an ABI Model 380A synthesizer (Applied Biosystems, Foster City, Calif.) following the manufacturers reconmmendations. Amplification of DNA fragments was performed by the polymerase chain reaction (PCR) using a Perkin Elmer GeneAmp® PCR System 9600. Reactions contained 100 pmol of each primer, 1 μg of template DNA (chromosomal DNA from Sac. erythraea NRRL2338), 2 units Vent$_R$® DNA polymerase in 100 μl volume of PCR buffer (10 mM KCl, 10 mM (NH$_4$)$_2$SO$_4$, 20 mM Tris-HCl (pH 8.8, @ 25° C.), 2.5 mM MgSO$_4$, 0.1% Triton® X-100) containing dATP (200 μM), dTTP (200 μM), dCTP (250 μM), and dGTP (250 μM). The reaction mixture was subjected to 30 cycles. Each cycle consisted of one period of 35 sec at 96° C. and one period of 2 min at 72° C. The reaction products were visualized and purified from low melting agarose. The PCR primers described in the examples were derived from the nucleotide sequence of the eryB and eryC genes of FIG. 4.

Transformation and Gene Replacement in Sac. erythraea

Protoplasts of Sac. erythraea strains were prepared and transformed with miniprep DNA isolated from E. coli according to published procedures (Yamamoto et al., *J Antibiotics*, 39:1304 (1986)). Non-integrative transformants, in the case of pWHM4 derivatives, were selected by regenerating the protoplasts and overlaying with thiostrepton (final concentration 20 µg/ml) as described (Weber et al., *Gene*, 68:173 (1988)). Integrative transformants, in the case of pWHM3 derivatives, were selected on thiostrepton-containing agar plates (15 µg/ml) as described by Weber et al., *Gene*, 68:173 (1988). Loss of the Th$^R$ phenotype was monitored after two rounds of non-selective growth in SGGP media (Yamamoto et al., *J Antibiotics*, 39:1304 (1986)) followed by protoplasting and serial dilution on non-selective agar media. Regenerated protoplasts were replica plated on thiostrepton-containing media. Th$^S$ (thiostrepton-sensitive) colonies arose at a frequency of $10^{-1}$. Retention of the mutant allele was established by Southern hybridization of several Th$^S$ colonies.

Fermentation

*Sac. erythraea* or *Streptomyces* cells are inoculated into 100 ml SCM medium (1.5% soluble starch, 2.0% Difco Soytone, 0.15% Yeast Extract, 0.01% $CaCl_2$) and allowed to grow for 3 to 6 days. The entire culture is then inoculated into 10 liters of fresh SCM medium. The fermenter is operated for a period of 4 to 7 days at 32° C. maintaining constant aeration and pH at 7.0. After the fermentation is complete, the cells are removed by centrifugation at 4° C. and the fermentation beer is kept cold until further use. When antibiotic selection to maintain a plasmid, such as pXC4 or pXB6, is required, thiostrepton (10 µg/ml) is added to both the 100 ml starter culture and the 10-liter fermenter.

The invention will be better understood in connection with the following examples, which are intended as an illustration of and not a limitation upon the scope of the invention. Both below and throughout the specification, it is intended that citations to the literature be expressly incorporated by reference.

EXAMPLE 1

Construction and characterization of *Sac. erythraea* ERBIV that produces 4"-deoxy4"-oxo-erythromycin A.

A. Construction of Plasmid pRBIV

A 4.3 kb PstI-HindIII fragment, which included the eryBIV gene, was isolated from the plasmid pAIX5 and subcloned into PstI-HindIII digested pUC19 to generate plasmid pUCBIV. After transformation and isolation of the plasmid from *E. coli*, the identity of pUCBIV was confirmed by digestion with MunI which released a fragment of 370 bp. Plasmid pUCBIV was then cut with the restriction enzyme NcoI, the restriction site filled in with Klenow enzyme, and the plasmid religated to generate plasmid pNCOBIV, (which now carried a frameshift mutation in the eryBIV gene). After transformation and isolation of the plasmid from *E. coli*, the identity of pNCOBIV was confirmed by digestion with NsiI and HindIII which released a fragment of 1.59 kb. (The NsiI site was formed by the fill-in and religation of the NcoI site.) Finally, plasmid pNCOBIV was digested with HindIII and SstI and the 3.2 kb fragment carrying the altered eryBIV gene was isolated and ligated into HindIII and SstI digested pWHM3 to generate plasmid pRBIV. After transformation and isolation of the plasmid from *E. coli*, the identity of pRBIV was confirmed by digestion with KpnI which released fragments of 5.2 kb, 4.4 kb, and 0.72 kb.

B. Construction of *Sac. erythraea* ERBIV

*Sac. erythraea* protoplasts were transformed with plasmid pRBIV and integrative transformants selected as described in General Methods. Resolution of the integrants by nonselective growth as described in General Methods yielded *Sac. erythraea* ERBIV in which the wild type copy of the eryBIV gene was replaced with the inactive mutant copy. Gene replacement was confirmed by Southern analysis of NcoI digested *Sac. erythraea* DNA and NcoI-NsiI digested *Sac. erythraea* DNA using the 1.58 kb NcoI-HindIII fragment isolated from plasmid pUCBIV (coordinates 681–2214, FIG. 4B) as a probe. Wild type *Sac. erythraea* and wild type resolvants display a hybridizing DNA fragment of 2.75 kb when digested with either NcoI or NcoI-NsiI, whereas *Sac. erythraea* strain ERBIV is characterized by hybridization to either a 16 kb DNA fragment or a 2.75 kb DNA fragment when digested with NcoI or NcoI-NsiI, respectively.

C. Isolation, purification, and properties of 4"-deoxy-4"-oxo-erythromycin A from *Sac. erythraea* ERBIV

*Sac. erythraea* strain ERBIV is fermented for 4 days in SCM media as described in General Methods. The fermentation broth of *Sac. erythraea* ERBIV is then cooled to 4° C. and adjusted to pH 4.0 and extracted once with methylene chloride. The aqueous layer is readjusted to pH 9.0 and extracted twice with methylene chloride and the combined basic methylene chloride extracts are concentrated to a solid residue. This is digested in methanol and chromatographed over a column of Sephadex LH-20 in methanol. Fractions are tested for bioactivity against a sensitive organism, such as *Staphylococcus aureus* Th$^R$, and active fractions are combined. The combined fractions are concentrated and the residue is digested in 10 ml of the upper phase of a solvent system consisting of n-heptane, benzene, acetone, isopropanol, 0.05 M, pH 7.0 aqueous phosphate buffer (5:10:3:2:5, v/v/v/v/v), and chromatographed on an Ito Coil Planet Centrifuge in the same system. Active fractions are combined, concentrated and partitioned between methylene chloride and dilute ammonium hydroxide (pH 9.0). The methylene chloride layer is separated and concentrated to yield the desired product as a white foam.

EXAMPLE 2

Construction and characterization of *Sac. erythraea* ER720(pASBVII) that produces 3-α-D-mycarosyl-5-β-D-desosaminoyl-12-hydroxy-erythronolide B.

Figure 7:
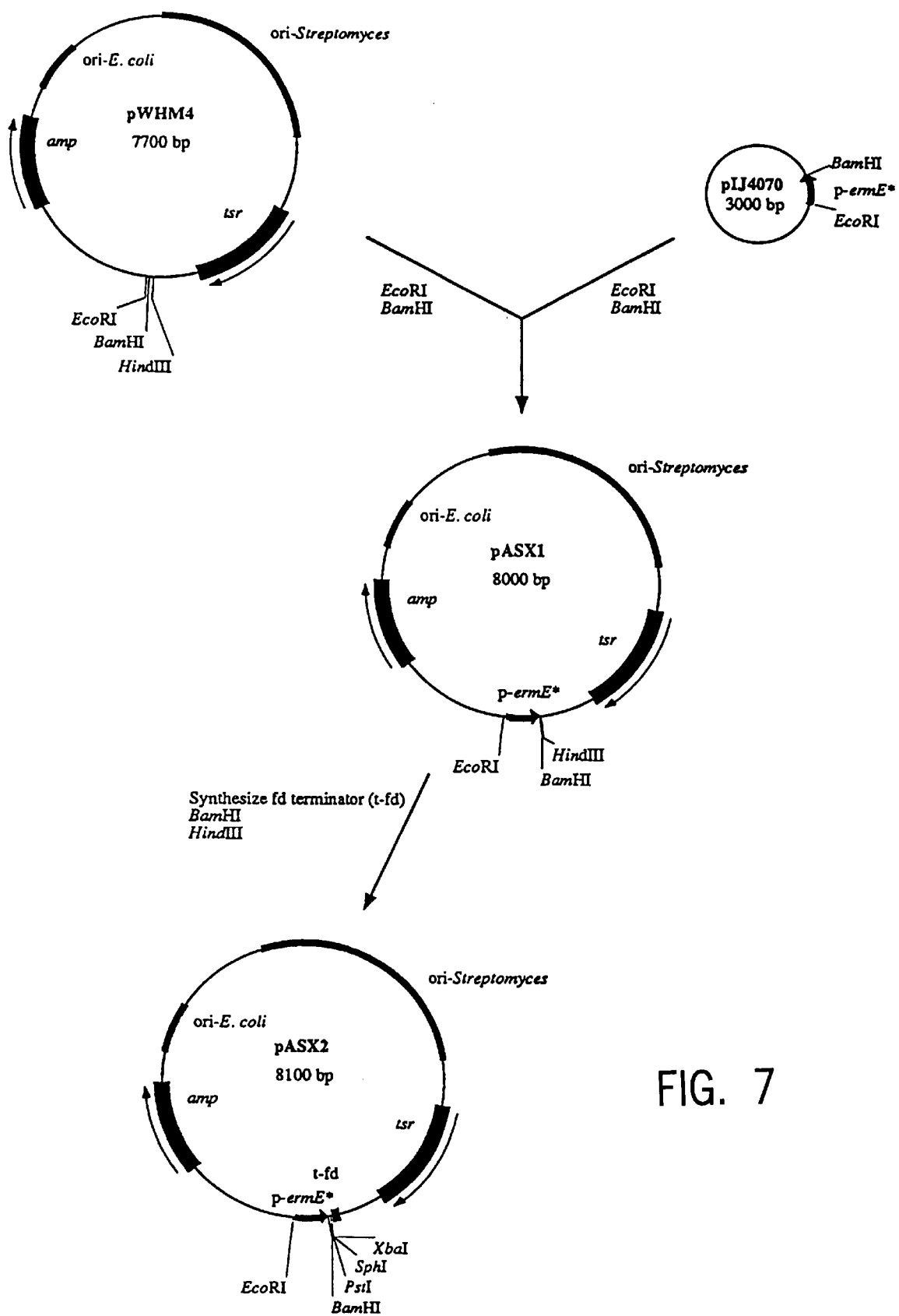

A. Construction of plasmid pASX2 (see FIG. 7)

The 290 bp EcoRI-BamHI segment carrying the ermE* promoter is isolated from plasmid pIJ4070 and ligated into EcoRI-BamHI digested pWHM4 DNA to form pASX1. After transformation and isolation of the plasmid from *E. coli*, the identity of pASX1 is confirmed by digestion with ApaLI which releases fragments of 3.9 kb, 2.5 kb, 1.2 kb, 0.5 kb, and 0.4 kb.

Two oligonucleotides of the sequences: SEQ ID NO:3 (5'-GATCCAGCGTCTGCAGGCATGCTCTAGATACAAT TAAAGGCTCCTTTTGGAGCCTTTTTTTTGGAGATTT CAACGT-3') and SEQ ID NO:4 (5'-AGCTACGTTGAAAATCTCCAAAAAAAAAGGCTC CAAAA GGAGCCTTTAATTGTATCTAGAGCATGC-CTGCAGAC GCTG-3'), corresponding to the (+) and (−) strands of the bacteriophage fd gene VIII transcription terminator (t-fd) [Beck et al. (1978) *Nucl. Acids Res.* 5:4495] and including restriction enzyme sites for the enzymes PstI, SphI, and XbaI, and overhanging ends compatible with BamHI and HindIII are synthesized and approximately 250 ng of each oligonucleotide are then mixed together in TE buffer and heated to 99° C. for 1 min. The solution is cooled slowly to room temperature allowing the oligonucleotides to anneal due to self complementarity, and the annealed oligonucleotides are then ligated into BamHI-HindIII digested pASX1 to give pASX2. After transformation and isolation of the plasmid from E. coli, the identity of pASX2 is confirmed by DNA sequencing of the 1.2 kb EcoRI-SalI fragment that contains the ErmE* promoter and the bacteriophage fd terminator.

Figure 8:
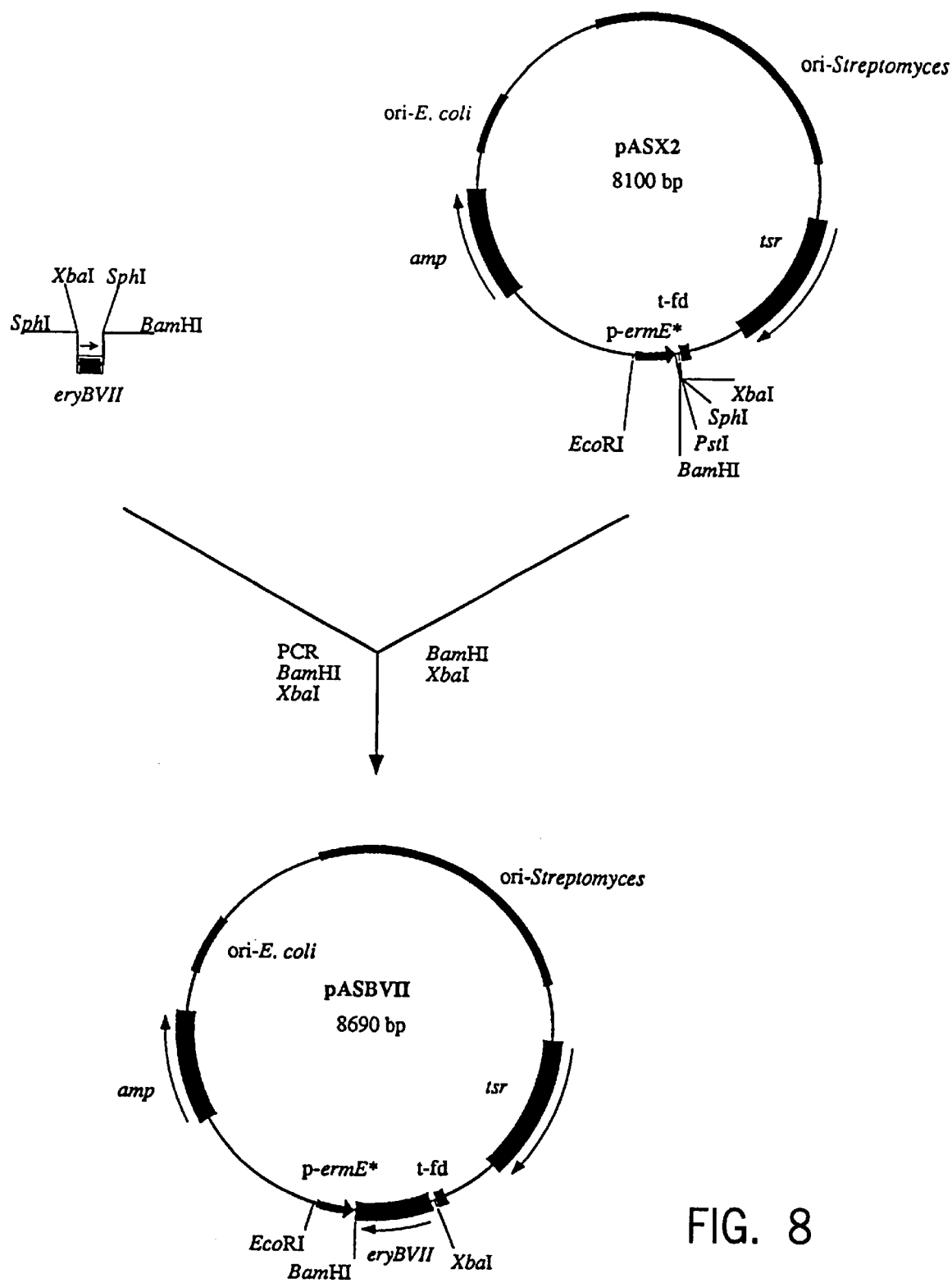
Figure 9B:
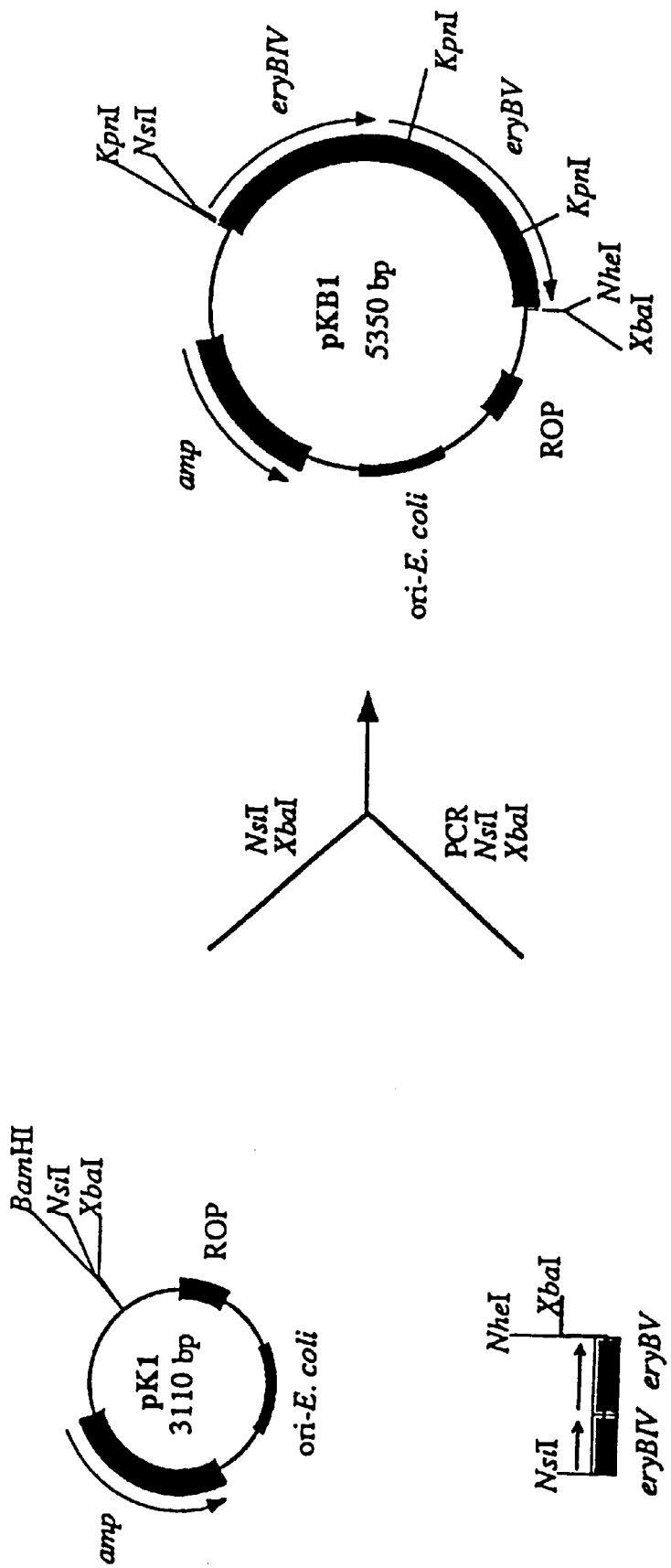
FIGS. 9(B)–(E) illustrates the construction of plasmid pKB6 which carries all of the eryb genes and is described in Example 3.
Figure 9C:
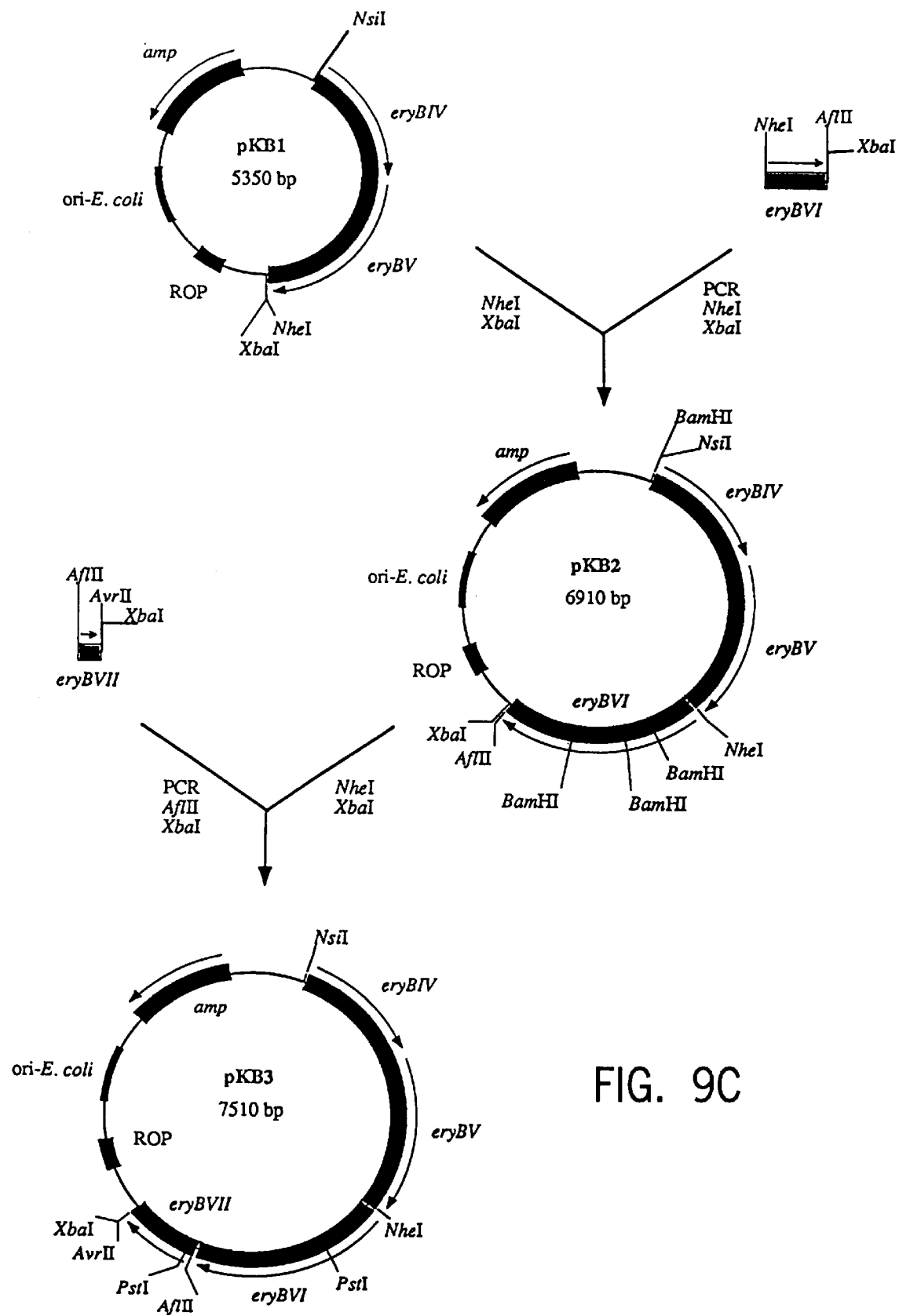
Figure 9D:
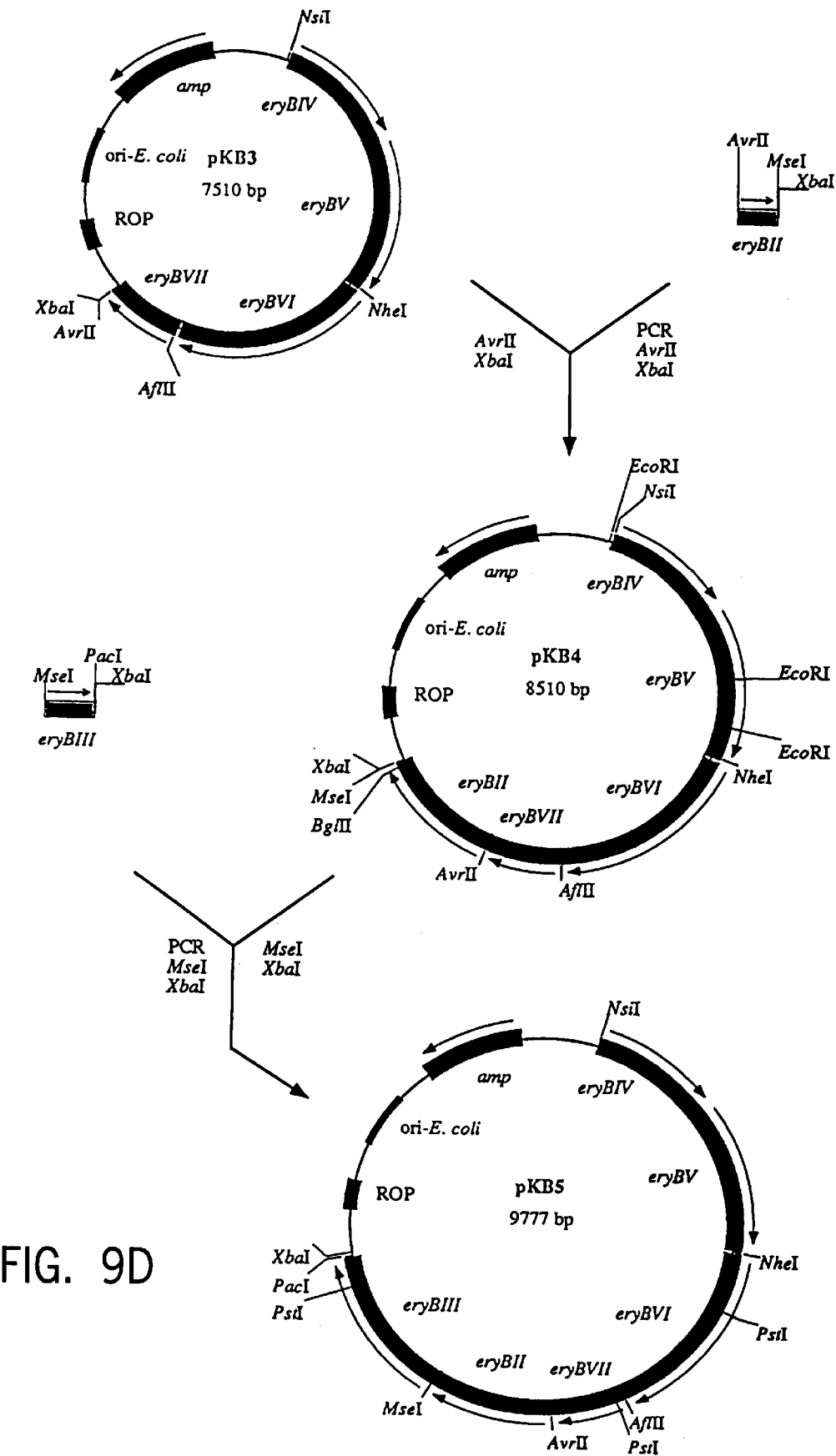
Figure 9E:
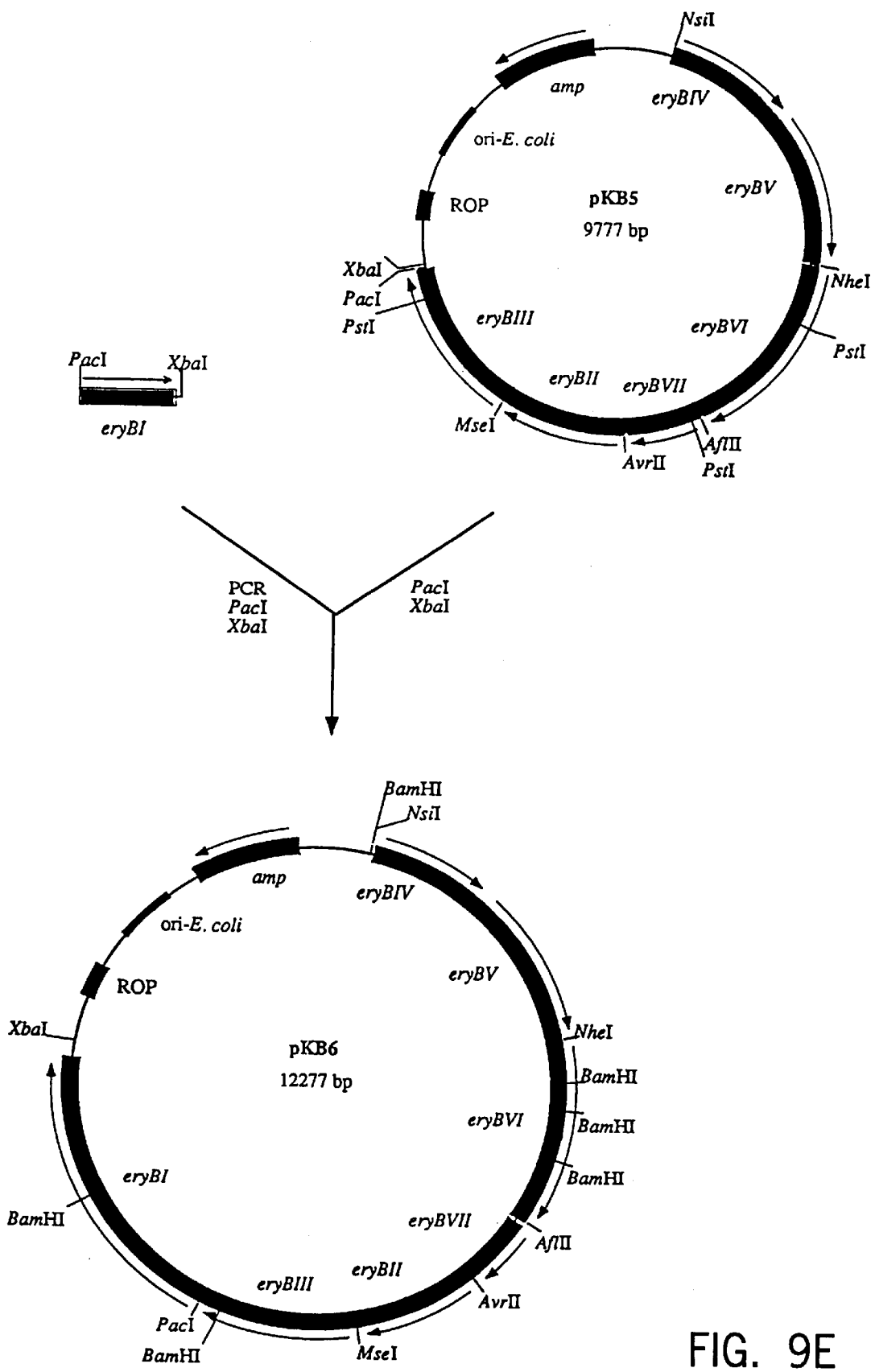

B. Construction of plasmid pASBVII (see FIG. 8)

The 598 base pair DNA segment that carries the eryBVII gene, comprising coordinates 7398–7996 (FIG. 4B), is amplified by PCR employing two oligonucleotides, SEQ ID NO:5 (5'-GATCGCATGCTCTAGAGTACGTGAGCTG-GCGGTGGCGG GC-3') and SEQ ID NO:6 (5'-GATCCGGATCCGCATGCTTCACCTGCCGGTGCTGGCGG G-3'). After digestion of the purified PCR product with BamHI-XbaI the PCR fragment was ligated to BamHI-XbaI digested pASX2 to give pASBVII. After transformation and isolation of the plasmid from E. coli, the identity of pAS-BVII is verified by DNA sequencing of the 880 bp EcoRI-XbaI insert.

C. Construction of Sac. erythraea ER720(pASBVII)

Sac. erythraea strain ER720 protoplasts are transformed with plasmid pASBVII and transformants are selected for with thiostrepton (15 µg/ml). To confirm transformation, total DNA is isolated from $Th^R$ colonies and used to transform E. coli. After transformation and isolation of the plasmid from E. coli, the identity of pASBVII is verified by restriction analysis with the enzymes PvuII and BamHI which releases a 1.48 kb fragment. Those Sac. erythraea colonies that are found to contain pASBVII are designated Sac. erythraea ER720(pASBVII).

D. Isolation, purification, and properties of 3-α-D-mycarosyl-5-β-D-desosaminoyl-12-hydroxy-erythronolide B from Sac. erythraea ER720(pASBVII)

Sac. erythraea ER720(pASBVII) is fermented for 3 days in SCM media with thiostrepton selection as described in General Methods. The fermentation broth is then cooled to 4° C. and adjusted to pH 4.0 and extracted once with methylene chloride. The aqueous layer is readjusted to pH 9.0 and extracted twice with methylene chloride and the combined extracts are concentrated to a solid residue. This is digested in methanol and chromatographed over a column of Sephadex LH-20 in methanol. Fractions are tested for bioactivity against a sensitive organism, such as Staphylococcus aureus $Th^R$, and active fractions are combined. The combined fractions are concentrated and the residue is digested in 10 ml of the upper phase of a solvent system consisting of n-heptane, benzene, acetone, isopropanol, 0.05 M, pH 7.0 aqueous phosphate buffer (5:10:3:2:5, v/v/v/v/v), and chromatographed on an Ito Coil Planet Centrifuge in the same system. Active fractions are combined, concentrated and partitioned between methylene chloride and dilute ammonium hydroxide (pH 9.0). The methylene chloride layer is separated and concentrated to yield the desired product as a white foam.

EXAMPLE 3

Construction and characterization of Streptomyces antibioticus ATCC 11891(pXB6) that produces 3-des-oleandrosyl-3-mycarosyl oleandomycin A. Construction of plasmid pKB6 and intermediates (see FIG. 9)

i) Construction of plasmid pKI

The DNA sequences of pBR322 (GenBank Accession #: J01749) and pUC19 (GenBank Accession #: X02514) are known. The 805 nt DNA segment comprising coordinates 1673 through 2478 of pBR322 is amplified by PCR employing two oligodeoxynucleotides, SEQ ID NO:7 (5'-GATCACATGTTCTTTCCTGCGTTATCCCCTG-3') and SEQ ID NO:8 (5'-GATCGGATCCATGCATGTCTAGAGCATCGCAGGATG CTGCTGGC-3'). After digestion of the purified PCR product with AflIII and BamHI the fragment is ligated into AflIII and BamHI digested pUC19 to give plasmid pK1. The identity of plasmid pK1, after transformation and isolation from E. coli, is verified by PvuII digestion which releases fragments of 0.55 kb and 2.55 kb. Plasmid pK1 contains the ROP region of pBR322 that controls plasmid copy number.

ii) Construction of plasmid pKB1

The 2.24 kb DNA segment that carries the eryBIV and eryBV genes, comprised between coordinates 56 and 2296 of the sequence presented in FIG. 4B, is amplified by PCR employing two deoxyoligonucleotides, SEQ ID NO:9 (5'-GAATGCATCCTGGAAAGCGAGCAAATGCTCCGGTG-3') and SEQ ID NO:11 (5'-GATCTAGAGCTAGCCGGCGTGGCGGCGCGTG-3'). After digestion with NsiI and XbaI the fragment is ligated into NsiI and XbaI digested pK1 to yield plasmid pKB1, 5.3 kb in size. The identity of plasmid pKB 1, after transformation and isolation from E. coli, is verified by KpnI digestion which releases fragments of 0.72 kb, 1.14 kb and 3.42 kb.

iii) Construction of plasmid pKB2

The 1.56 kb DNA segment that carries the eryBVI gene, comprised between coordinates 3121 and 4677 of the sequence presented in FIG. 4B, is amplified by PCR employing two deoxyoligonucleotides, SEQ ID NO:11 (5'-GATCGCTAGCCGTGACCGGACCCTTACAGTGAGTG-3') and SEQ ID NO:12 (5'-GATCTAGACTTAAGTCATCCGGCGGTCCTGGTGTAG ACGGC-3'). After digestion with NheI and XbaI the fragment is ligated into NheI and XbaI digested pKB1 to give plasmid pKB2, 6.9 kb in size. The identity of plasmid pKB2, after transformation and isolation from E. coli, is confirmed by BamHI digestion which releases fragments of 0.22 kb, 0.40 kb, 2.6 kb and 3.7 kb.

iv) Construction of plasmid pKB3

The 0.6 kb DNA segment that carries the e y BVII gene, comprised between coordinates 7385 and 7987 of the sequence presented in FIG. 4B, is amplified by PCR employing two deoxyoligonucleotides, SEQ ID NO:13 (5'-GATCTTAAGAACCGGAGTTGCGAGTACGTGAGCTG GCG-3') and SEQ ID NO:14 (5'-GATCTAGACCTAGGTCACCTGCCGGTGCTGGCGG GCTC-3'). After digestion with AflII and XbaI the fragment is ligated into AflII and XbaI digested pKB2 giving plasmid pKB3, 7.5 kb in size. The identity of plasmid pKB3, after transformation and isolation from E. coli, is verified by PstI digestion which releases fragments of 1.1 kb and 6.4 kb.

v) Construction of plasmid pKB4

The 1.0 kb DNA segment that carries the eryBII gene, comprised between coordinates 2385 and 3410 of the sequence presented in FIG. 4A, is amplified by PCR employing two deoxyoligonucleotides, SEQ ID NO:15 (5'-GATCCTAGGCCGCAGGAAGGAGAGAACCACG-3') and SEQ ID NO:16 (5'-GATCTAGATTAATCACTGCAACCAGGCTTCCGGC-3'). Following digestion with AvrII and XbaI the fragment is ligated into AvrII and XbaI digested pKB3 yielding the desired plasmid pKB4. After transformation and isolation of the plasmid from E. coli, the identity of pKB4, 8.5 kb in size, is verified by BVII and EcoRI digestion which releases fragments of 0.41 kb, 1.6 kb, 3.1 kb and 3.4 kb.

vi) Construction of plasmid pKB5

The DNA sequence of eryBIII has been reported [Haydock et al (1991) *Mol Gen Genet* 230:120]. The 1.3 kb DNA segment that carries the eryBIII gene, comprised between coordinates 3965 and 5232 of the sequence depicted in [Haydock et al (1991) *Mol Gen Genet* 230:120], is amplified by PCR employing two deoxyoligonucleotides, SEQ ID NO:17 (5'-GATTAATTGGCCGCGGCGCCGCGCTCGTTATG-3') and SEQ ID NO:18 (5'-GATCTAGATAATTAATCATACGACTTCCAGTCGGG GTAG-3'). After digestion with MseI and XbaI the fragment is ligated into MseI and XbaI digested pKB4 to give the desired plasmid pKB5, 9.8 kb in size. The identity of pKB5, after transformation and isolation from *E. coli*, is verified by PstI digestion which releases fragments of 1. I kb, 2.5 kb, and 6.1 kb, visualized by gel electrophoresis.

vii) Construction of plasmid pKB6

The eryBI gene has been mapped [Haydock et al (1991) *Mol Gen Genet* 230:1201] and the DNA sequence on both flanks of eryBI is known [Haydock et al (1991) *Mol Gen Genet* 230:120] and GenBank Accession # M11200. The 2.5 kb DNA segment that carries the eryBI gene, comprised between coordinates 1.1 and 3.6 of the map presented in Haydock et al., is amplified by PCR employing two deoxyoligonucleotides: SEQ ID NO:19 (5'-GATTAATTAATGATCAAGCTGAAAATTGTTTGCATG-3') and SEQ ID NO:20 (5'-GATCTAGACTGCCGGCTCAGCCTTCCCAGGTTCG-3'). After digestion with PacI and XbaI the fragment is ligated into PacI and XbaI digested pKB5 to give plasmid pKB6, 12.3 kb in size. The identity of pKB6, after transformation and isolation from *E. coli*, is verified by BamHI digestion which releases fragments of 0.22 kb, 0.40 kb, 1.4 kb, 2.6 kb, 3.3 kb and 4.4 kb. Plasmid pKB6 carries all of the eryB genes, eryBI–eryBVII, that are involved in the biosynthesis of mycarose and its attachment to the polyketide.

B. Construction of Plasmid pXSB6 (see FIG. 11)

The 9.2 kb NsiI-XbaI segment of pKR6, prepared as described in Example 3(A)(vii) above, that carries all of the eryB genes is isolated and ligated into PstI-XbaI digested pASX2, prepared as described in Example 2(A) above, to give plasmid pXSB6. After transformation and isolation of the plasmid from *E. coli*, the identity of pXSB6, 17.2 kb in size, is verified by the observation of fragments of 0.41 kb, 1.9 kb, and 14.9 kb after EcoRI digestion. Plasmid pXSB6 carries all of the etyb genes in a transcriptional fusion downstream of the ermE* promoter on an *E. coli*-Streptomyces shuttle plasmid.

C. Construction of Plasmid pXB6 i) Construction of plasmid pN702 (see FIG. 10)

Figure 10:
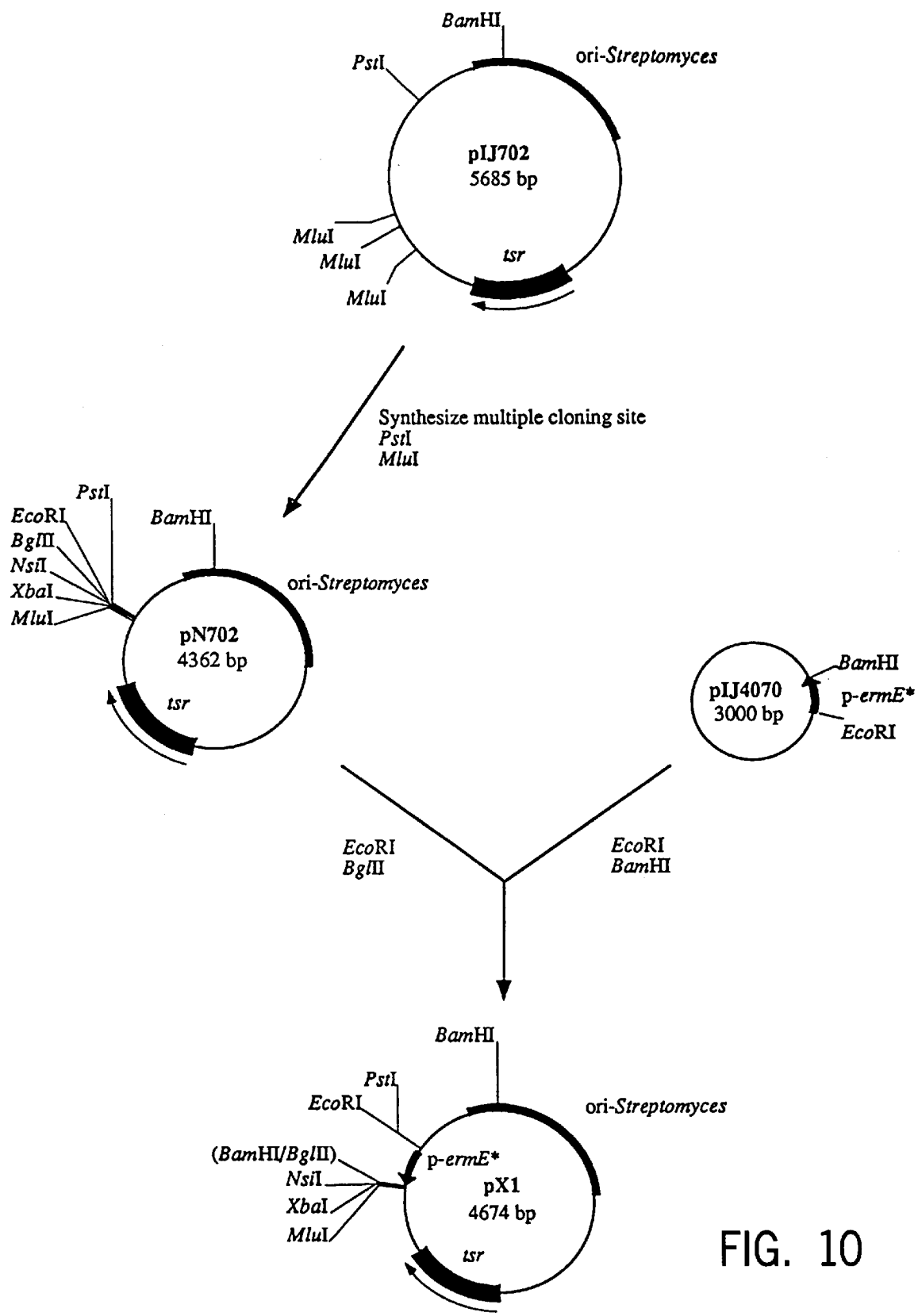
FIG. 10 illustrates the construction of expression plasmid pX1 described in Example 3.

Two oligonucleotides of the sequences: SEQ D NO:21 5'-GGAATTCAGATCTATGCATTCTAGAA-3') and SEQ ID NO:22 (5'-CGCGTTCTAGAATGCATAGATCTGAATTCCTGCA-3') that include restriction enzyme sites for the enzymes EcoRI, BglII, NsiI, and XbaI and overhanging ends compatible with PstI and MluI are synthesized. Approximately 250 ng of each oligonucleotide are then mixed together in TE buffer and heated to 99° C. for 1 min. After the solution is cooled slowly to room temperature allowing the oligonucleotides to anneal due to self complementarity, the annealed oligonucleotides are ligated into PstI-MluI digested pIJ702 to yield the desired plasmid pN702. After transformation and isolation of the plasmid from *Streptomyces lividans* 1326, the identity of plasmid pN702, 4.3 kb in size, is verified by the observation of fragments of 0.75 kb and 3.6 kb after EcoRI-BamHI or XbaI-BamHI digestion.

ii) Construction of plasmid pX 1 (see FIG. 10)

Figure 11:
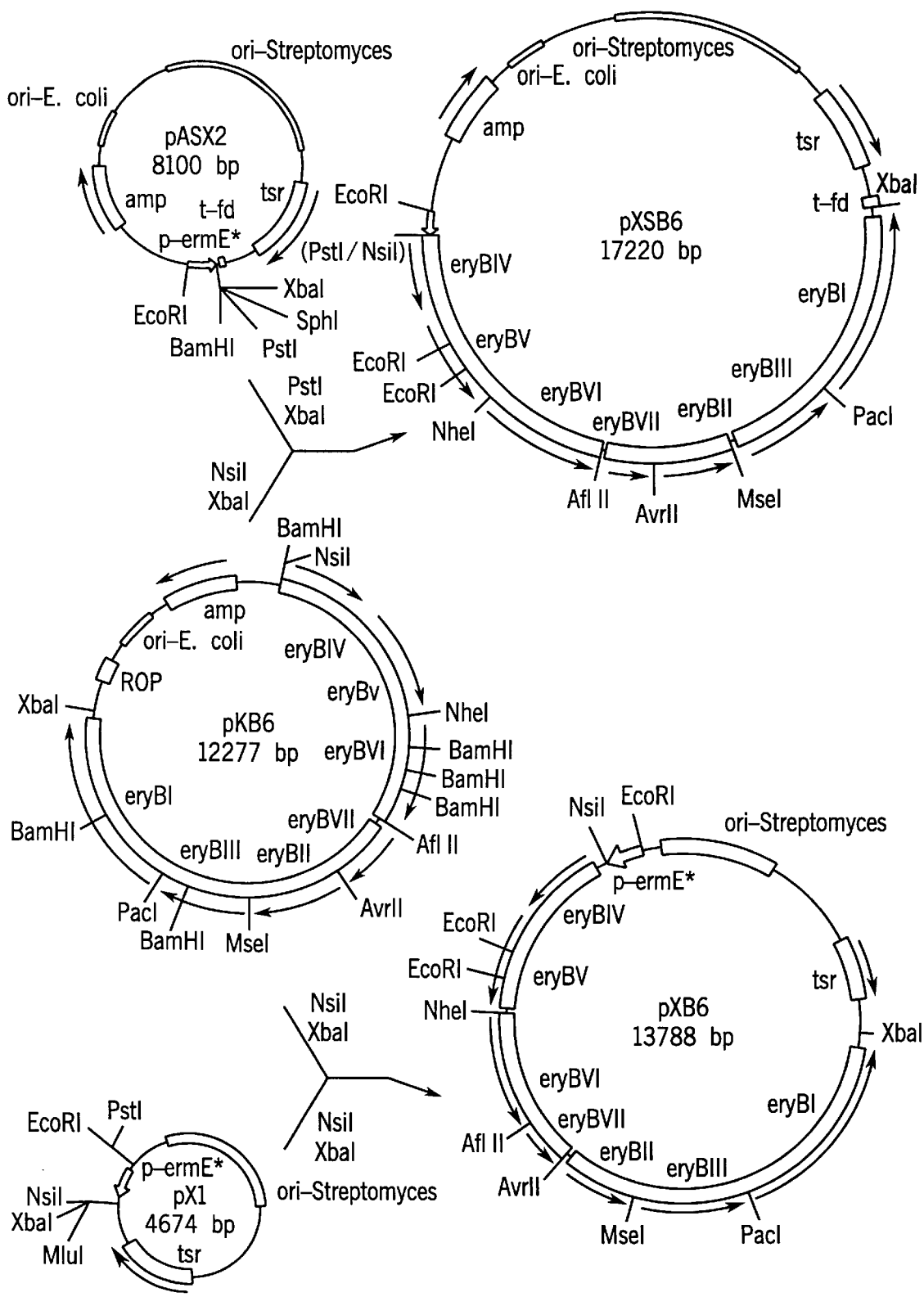
FIG. 11 illustrates the construction of the eryB expression plasmids pXSB6 and pXB6 described in Example 3.

The 290 bp EcoRI-BamHI segment that carries the ermE* promoter is isolated from plasmid pIJ4070 and ligated into EcoRI-BglII digested pN702 to give plasmid pX1. The resulting mixture contains the desired plasmid pX1. After transformation and isolation of the plasmid from *Streptomyces lividans* 1326, the identity of plasmid pX1, 4.6 kb in size, is verified by the observation of fragments of 1.0 kb and 3.6 kb after NsiI-BamHI digestion.

iii) Construction of plasmid pXB6 (see FIG. 11)

The 9.2 kb NsiI-XbaI segment of pKB6, prepared as described in Example 3(A)(vii) above, that carries all of the eryB genes is isolated and ligated into NsiI-XbaI digested pX1 to give the desired plasmid pXB6. After transformation and isolation of the plasmid from *Streptomyces lividans* 1326, the identity of plasmid pXB6, 13.8 kb in size, is verified by the observation of fragments of 0.41 kb, 1.9 kb, and 11.5 kb after EcoRI digestion. Plasmid pXB6 carries all of the eryB genes in a transcriptional fusion to the ermE* promoter on a Streptomyces plasmid.

D. Construction of *Streptomyces antibioticus* ATCC 11891 (pXB6)

Approximately 500 µg of plasmid pXB6, isolated from *Streptomyces lividans* 1326(pXB6), are electroporated into the oleandomycin producer *Streptomyces antibioticus* ATCC 11891 and several of the resulting Thio$^R$ colonies that appear on the R3M-agar plates containing thiostrepton are analyzed for their plasmid content. The presence of plasmid pXB6, 13.8 kb in size, is verified by the observation of fragments of 0.41 kb, 1.9 kb, and 11.5 kb after EcoRI digestion.

E. Isolation, purification, and properties of 3-des-oleandrosyl-3-mycarosyl oleandomycin from *Streptomyces antibioticus* ATCC 11891 (pXB6)

*Streptomyces antibioticus* ATCC 11891 (pXB6) is fermented for 5 days in SCM media with thiostrepton selection as described in General Methods. The fermentation broth is then cooled to 4° C. and adjusted to pH 4.0 and extracted once with methylene chloride. The aqueous layer is readjusted to pH 9.0 and extracted twice with methylene chloride and the combined extracts are concentrated to a solid residue. This is digested in methanol and chromatographed over a column of Sephadex LH-20 in methanol. Fractions are tested for bioactivity against a sensitive organism, such as *Staphylococcus aureus* Th$^R$, and active fractions are combined. The combined fractions are concentrated and the residue is digested in 10 ml of the upper phase of a solvent system consisting of n-heptane, benzene, acetone, isopropanol, 0.05 M, pH 7.0 aqueous phosphate buffer (5:10:3:2:5, v/v/v/v/v), and chromatographed on an Ito Coil Planet Centrifuge in the same system. Closely eluting active fractions are combined, concentrated and partitioned between methylene chloride and dilute ammonium hydroxide (pH 9.0). The methylene chloride layer is separated and concentrated to yield the desired product as a white foam.

EXAMPLE 4

Construction and characterization of *Streptomyces violaceoniger* NRRL 2834(pXC4) that produces 5-des-chalcosyl-5-desosamrrinoyl lankamycin

Figure 12A:
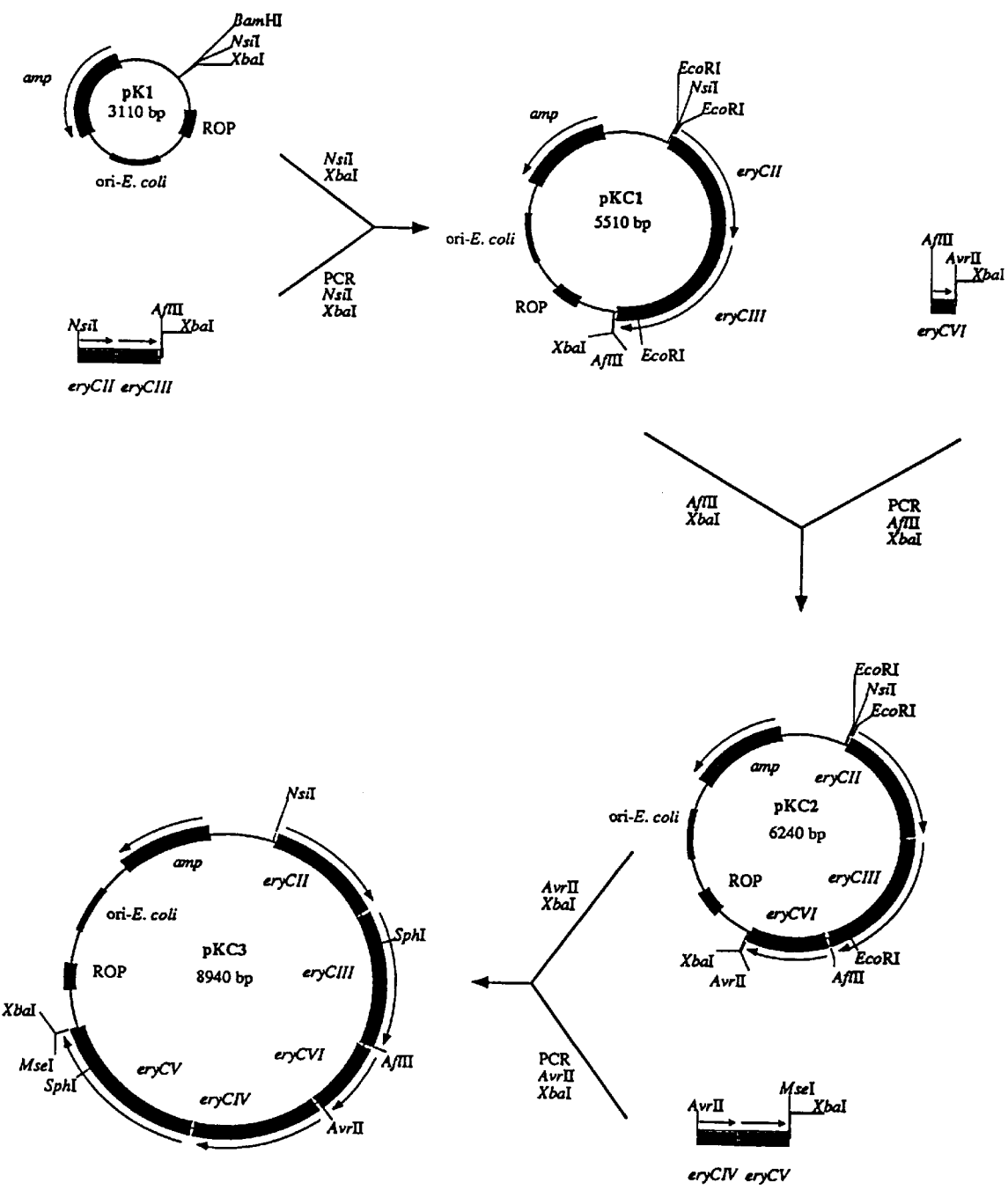
FIGS. 12(A)–(B) illustrates the construction of plasmid pKC4 which carries all of the eryC genes described in Example 4.
Figure 12B:
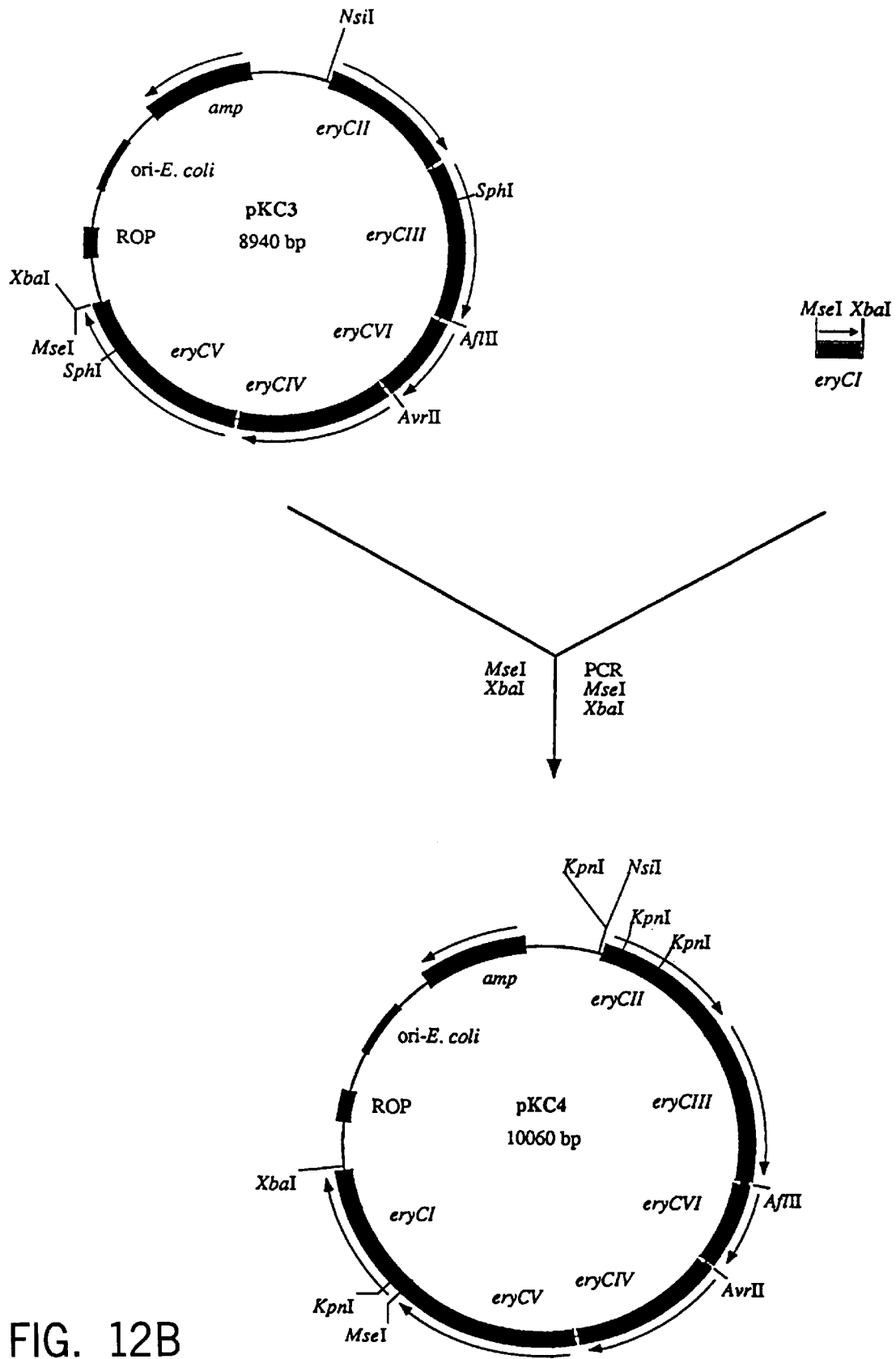

A. Construction of plasmid pKC4 and intermediates (see FIG. 12)

i) Construction of plasmid pKC1

The 2.4 kb DNA segment that carries the eryCII and eryCIII genes, comprised between coordinates 33 and 2413 of the sequence presented in FIG. 4A, is amplified by PCR employing two deoxyoligonucleotides, SEQ ID NO:23 (5'-GAATGCATCTGGCTGGGCGGAGGGAATTCATG-3') and SEQ ID NO:24 (5'-GATCTAGACTTAAGTCATCGTGGTTCTCTCCTTCC TGC GGC-3'). After digestion with NsiI and XbaI the purified PCR fragment is ligated into NsiI and XbaI digested pK1 to give plasmid pKC1, 5.5 kb in size. The identity of plasmid pKC1, after transformation and isolation from E. coli, is verified by EcoRI digestion which releases fragments of 2.2 kb and 3.3 kb.

ii) Construction of plasmid pKC2

The 732 bp DNA segment that carries the eryCVI gene, comprised between coordinates 2331 and 3063 of the sequence presented in FIG. 4B, is amplified by PCR employing two deoxyoligonucleotides, SEQ ID NO:25 (5'-GATCCTTAAGCTCCGGAGGGAGCAGGGATG-3') and SEQ ID NO:26 (5'-GATCTAGACCTAGGTCATCCGCGCACACCGACGA AC- 3'). After digestion with AflII and XbaI the purified PCR fragment is ligated into AflII and XbaI digested pKC1 to give plasmid pKC2, 6.2 kb in size. The identity of plasmid pKC2, after transformation and isolation from E. coli, is verified by XbaI-EcoRI digestion which releases fragmentsof 0.95 kb, 2.2 kb and 3.1 kb.

iii) Construction of plasmid pKC3

The 2.7 kb DNA segment that carries the eryCIV and eryCV genes, comprised between coordinates 4650 and 7386 of the sequence presented in FIG. 4B, is amplified by PCR employing two deoxyoligonucleotides, SEQ ID NO:27 (5'-GATCCTAGGCCGTCTACACCAGGACCGCCGG-3') and SEQ ID NO:28 (5'-GATCTAGATTAATCACCTICCGCGCAGGAAGCCGC-3'). After digestion with AvrII and XbaI the purified PCR fragment is ligated into AvrII and XbaI digested pKC2 to yield plasmid pKC3, 9.0 kb in size. The identity of plasmid pKC3, after transformation and isolation from E. coli, is verified by SphI digestion which releases fragments of 4.0 kb and 5.0 kb.

iv) Construction of plasmid pKC4

The DNA sequence of the eryCI gene has been determined (GenBank Accession #X15541). The 1.1 kb DNA segment that carries the eryCI gene, comprised between coordinates 38 and 1161 of the sequence indicated above, is amplified by PCR employing two deoxyoligonucleotides, SEQ ID NO:29 (5'-GATCTTAAGCCGCCACTCGAACGGACACTCG-3') and SEQ ID NO:30 (5'-GATCTAGATCAAGCCCCAGCCTTGAGGG-3'). After digestion with MseI and XbaI the fragment is ligated into MseI and XbaI digested pKC3 to give plasmid pKC4, 10.1 kb in size. The identity of plasmid pKC4, after transformation and isolation from E. coli, is verified by KpnI digestion which releases fragments of 0.15 kb, 0.31 kb, 4.1 kb and 5.5 kb. Plasmid pKC4 carries all of the eryC genes, eryCI–eryCVI, that are involved in the biosynthesis of desosamine and its attachment to the polydetide.

Figure 13:
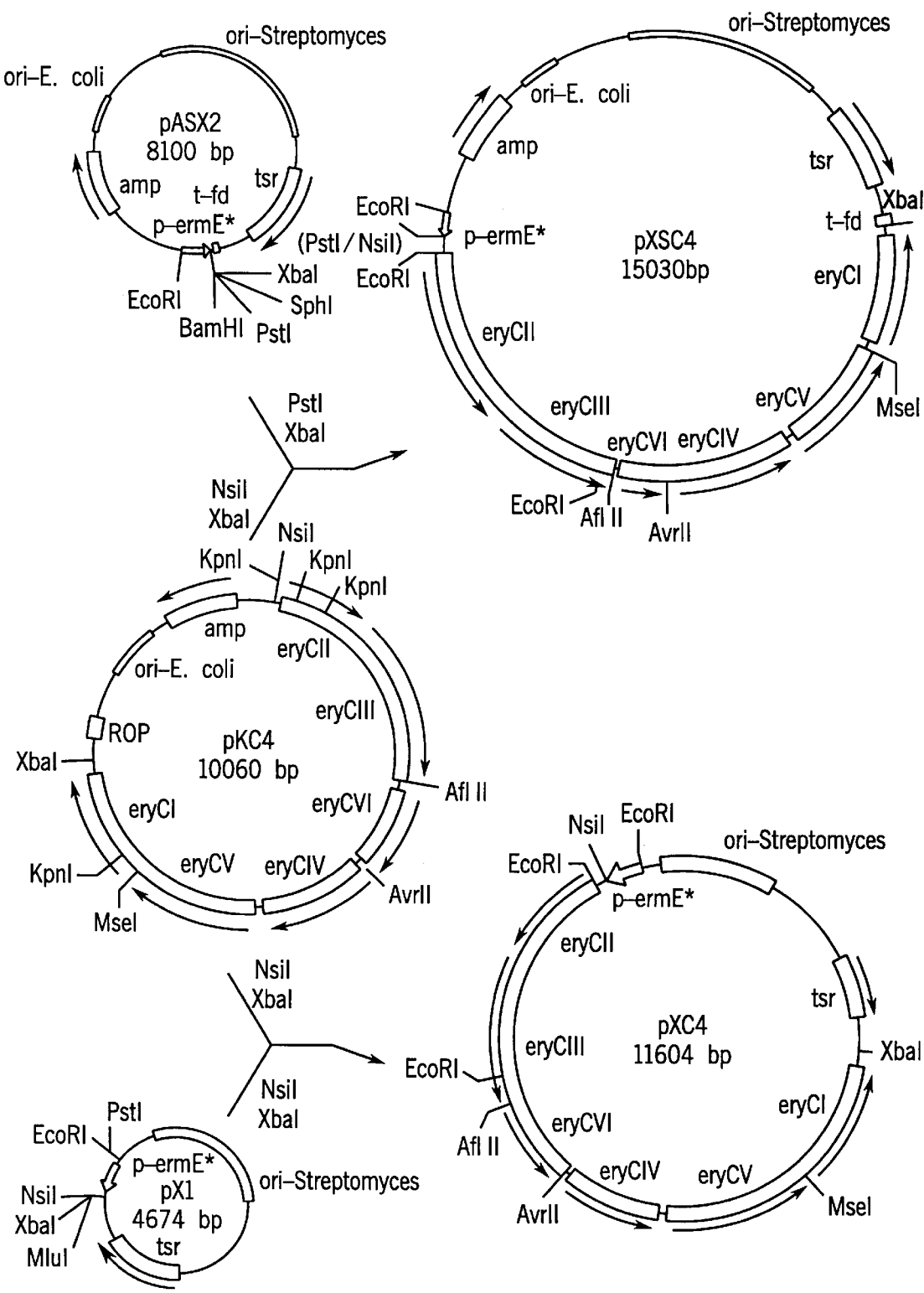
FIG. 13 illustrates the construction of the eryC expression plasmids pXSC4 and pXC4 described in Example 4.

B. Construction of Plasmid pXSC4 (see FIG. 13)

The 6.9 kb NsiI-XbaI segment of pKC4 that carries all of the eryC genes is isolated and ligated into PstI-XbaI digested pASX2, prepared as described in Example 2(A), to give the desired plasmid pXSC4, 14.9 kb in size, wherein all of the eryC genes are transcriptionally linked downstream of the ermE* promoter on an E. coli-Streptomyces shuttle plasmid. The identity of plasmid pXSC4, after transformation and isolation from E. coli, is verified by the observation of fragments of 0.29 kb, 2.2 kb, and 12.4 kb after EcoRI digestion.

C. Construction of Plasmid pXC4 (see FIG. 13)

The 6.9 kb NsiI-XbaI segment of pKC4 that carries all of the eryC genes is isolated and ligated into NsiI-XbaI digested pX 1, prepared as described in Example 3(C)(ii), to give the desired plasmid pXC4, 11.5 kb in size, wherein all of the eryC genes are transcriptionally linked downstream of the ermE* promoter on a Streptomyces plasmid. After transformation and isolation of the plasmid from Streptomyces lividans 1326, the identity of plasmid pXC4 is verified by the observation of fragments of 0.29 kb, 2.2 kb, and 9.0 kb after EcoRI digestion.

D. Construction of Streptomyces violaceoniger NRRL 2834 (pXC4)

Approximately 500 μg of the plasmid pXC4, isolated from Streptomyces lividans 1326(pXC4), are electroporated into the lankamycin producer Streptomyces violaceoniger NRRL 2834 and several of the resulting Thio$^R$ colonies that appear on the R3M-agar plates containing thiostrepton are analyzed for their plasmid content. The presence of plasmid pXC4 is verified by the observation of fragments of 0.29 kb, 2.2 kb, and 9.1 kb in size after EcoRI digestion of the plasmid.

E. Isolation, purification, and properties of 5-des-chalcosyl-5-desosaminoyl lankamycin S. violaceoniger NRRL 2834(pXC4) is fermented for 5 days in SCM media with thiostrepton selection as described in General Methods. The fermentation broth is then cooled to 4° C. and adjusted to pH 4.0 and extracted once with methylene chloride. The aqueous layer is readjusted to pH 9.0 and extracted twice with methylene chloride and the combined extracts are concentrated to a solid residue. This is digested in methanol and chromatographed over a column of Sephadex LH-20 in methanol. Fractions are tested for bioactivity against a sensitive organism, such as Staphylococcus aureus Th$^R$, and active fractions are combined. The combined fractions are concentrated and the residue is digested in 10 ml of the upper phase of a solvent system consisting of n-heptane, benzene, acetone, isopropanol, 0.05 M, pH 7.0 aqueous phosphate buffer (5:10:3:2:5, v/v/v/v/v), and chromatographed on an Ito Coil Planet Centrifuge in the same system. Active fractions are combined, concentrated and partitioned between methylene chloride and dilute ammonium hydroxide (pH 9.0). The methylene chloride layer is separated and concentrated to yield the desired product as a white foam.

Although the present invention is illustrated in the examples listed above in terms of preferred embodiments, these examples are not to be regarded as limiting the scope of the invention. The above illustrations serve to describe the principles and methodologies involved in creating the types of genetic alterations that can be introduced into Sac. erythraea and/or other Streptomyces that result in the synthesis of novel glycosylation-modified polyketide products. Although a single Type I alteration, leading to the production of for example, 4"-deoxy-4"-oxo-erythromycin A, is specified herein, it is obvious to those skilled in the art that other Type I changes can be introduced into the eryb and/or eryC genes leading to novel glycosylation-modified polyketide structures. Examples of additional Type I alterations leading to usefull novel compounds include but are not limited to: mutations in the eryBVII gene conceivably leading to 3-α-D-mycarosyl-5-β-D-desosaminoyl-12-hydroxy-erythronolide B and mutations in the eryCVI gene conceivably leading to N-3α'-des-dimethyl erythromycin A. Moreover, it is obvious that Type I alterations in two or more different eryB and/or eryC genes can be combined leading to novel glycosylation-modified polyketide structures.

Examples of combinations of two Type I alterations leading to useful compounds include but are not limited to: mutations in the eryBIV and eryBVII genes conceivably leading to 3-α-D4"-deoxy-4"-oxo-mycarosyl-5-β-D-desosaminoyl-1 2-hydroxy-erythronolide B; mutations in the eryBIV and eryCVI genes conceivably leading to 4"-deoxy-4"-oxo-(N-3α'-des-dimethyl)-erythromycin A; and mutations in the eryBIV, eryBVII, and eryCVI genes conceivably leading to 3-α-D-4"-deoxy-4"-oxo-mycarosyl-5-β-D-(N-3α'-des-dimethyl)-desosaminoyl-12-hydroxy-erythronolide B. All Type I mutations or combinations of two or more Type I mutations in the eryBII, eryBIV, eryBV, eryBVI, eryBVII, eryCII, eryCIII, eryCIV, eryCV, or eryCVI genes, the *Sac. erythraea* strains that carry said mutations or combinations of mutations, and the corresponding polyketides produced from said strains, therefore, are included within the scope of the present invention.

Although the Type II mutation specified herein was constructed with the eryBVII gene on a self-replicating plasmid it is obvious that other eryB genes and eryC genes can be expressed in an antisense orientation leading to novel glycosylation-modified polyketide structures. Examples of additional Type II alterations leading to useful compounds include but are not limited to: antisense expression of the eryBIV gene conceivably leading to 4"-deoxy-4"-oxo-erythromycin A and antisense expression of the eryCVI gene conceivably leading to N-3α'-des-dimethyl erythromycin A. Moreover, it will occur to those skilled in the art that promoters other than the ermE* promoter, for example the melC promoter of pIJ702, will be suitable for antisense expression, and that many self-replicating vectors in addition to pWHM4 will function to carry the antisense alteration. It will also occur to those skilled in the art that a self-replicating vector is not required for this invention and that the antisense alteration can be introduced directly into the chromosome using the same principles employed to construct a Type I gene alteration. An example of a Type II alteration that is introduced directly into the chromosome is the eryBVII antisense alteration described in Example 2 wherein DNA segments immediately upstream of the eryK gene are used to flank the ermE-eryBVII-phage fd terminator grouping in a pWRM3 vector, and this vector is integrated into and then resolved from the chromosome leaving the ermE*-eryBVII-phage fd terminator grouping stably incorporated into this nonessential region of the chromosome of *Sac. erythraea* conceivably leading to the production of 3-α-D-mycarosyl-5-β-D-desosaminoyl-12-hydroxy-erythronolide B. All Type II mutations in the eryBII, eryBIV, eryBV, eryBVI, eryBVII, eryCII, eryCIII, eryCIV, eryCV, or eryCVI genes whether carried on a self-replicating plasmid or integrated into a nonessential region of the chromosome, the *Sac. erythraea* strains that carry said mutations, and the corresponding polyketides produced from said strains, therefore, are included within the scope of the present invention.

Although Type m alterations, leading to the production of 5-des-chalcosyl-5-desosaminoyl lankamycin in *Streptomyces violaceoniger* and 3-des-oleandrosyl-3-mycarosyl oleandomycin in *Streptomyces antibioticus*, are specified herein, it is obvious that Type III alterations can be introduced into any polyketide producing microorganism leading to novel glycosylation modified polyketides. It will also occur to those skilled in the art that both the eryB and eryC genes can either be cotransformed into a polyketide producing microorganism or grouped together on a single vector that is introduced into a polyketide producing microorganism. An example of a Type III change using both the eryB and eryC genes together is their introduction into *Streptomyces violaceoniger* conceivably leading to 3-des-(4"-O-acetylarcanosyl)-3-mycarosyl-5-des-chalcosyl-5-desosaminoyl lankamycin. Although the Type III alterations specified herein have indicated a specific genetic order of the eryB or eryC genes, it will occur to those skilled at the art that many different genetic arrangements of the eryB or eryC genes will produce similar results. It will also that occur to those skilled at the art that certain arrangements of the eryB and/or eryC genes that lack one or more of the respective eryB and/or eryC genes will lead to the production of novel glycosylated polyketides in which intermediate compounds in the biosynthesis of mycarose and/or desosamine, respectively, such as those outlined in FIGS. 2 and 3, are attached to the polyketide. An example of a Type III alteration in which only a subset of the eryB and/or eryC genes are used is the introduction of a pXC4 derivative that lacks the eryCVI gene, removed by digestion of plasmid pXC4 with AflII and AvrII followed by treatment with the Klenow fragment of DNA polymerase I and religation, into *Streptomyces violaceoniger* leading to the production of to 5-des-chalcosyl-5-(N-3α'-des-dimethyl desosaminoyl) lankamycin. It will also that occur to those skilled at the art that promoters other than ermE or ermE*, such as the melC promoter of plasmid pIJ702, and vectors other than pWHM4 or pIJ702 can also be utilized in the construction of a Type III alteration, and these variants are, of course, considered to be within the scope of the invention. Finally, it will also occur to those skilled in the art that a self-replicating vector is not required for this invention and that an assembly of sugar biosynthesis genes can be introduced directly into the chromosome of a heterologous host using the same principles employed to construct a Type I gene alteration once a nonessential region of the heterologous host chromosome has been identified. Alternatively, plasmids or bacteriophages which undergo site-specific recombination with host genes may also be used to introduce eryB and eryC genes into a host to effect Type III alterations. All Type III alterations using one or more of the eryBHI, eryBIV, eryBV, eryBVI, eryBVII, eryCII, eryCIII, eryCIV, eryCV, or eryCVI genes, the polyketide producing strains that carry said alterations, and the corresponding polyketides produced from said strains, therefore, are included within the scope of the present invention.

In addition, it is also possible to create combinations of Type I and Type II alterations such that some Type I eryB and/or eryC mutations are introduced directly into the *Sac. erythraea* chromosome in the appropriate locus, while other eryB and/or eryC genes are inactivated by Type II alterations using a self-replicating or integrating vector. For example, combination of a Type I alteration, such as a mutation in eryBIV, and a Type II alteration, such as transformation with pASBVII, will conceivably lead to production of 3-α-D-4"-deoxy-4"-oxo-mycarosyl-5-β-D-desosaminoyl-1 2-hydroxy-erythronolide B. All combinations of two or more alterations of Type I and Type II, the *Sac. erythraea* strains that carry such alterations, and the glycosylated polyketides produced from such strains are included within the scope of the present invention.

As an extension of the examples reported with the eryB and/or eryC genes, it is possible to apply the method described herein to heterologous sugar biosynthesis genes that are similar to the eryB and/or eryC genes. The construction of strains carrying heterologous sugar biosynthesis genes that lead to the production of novel glycosylated polyketides requires: (i) cloning of the sugar biosynthesis genes from any other glycosylated-polyketide producing actinomycete, (ii) determining the nucleotide sequence of the cloned gene(s); (iii) excising and assembling the cloned gene(s) into vectors suitable for Type I, Type II, or Type III alterations; and (iv) transformation of polyketide producing microorganisms and screening for the novel compound. Any polyketide-associated sugar biosynthesis gene can thus be precisely excised from the genome of a glycosylated polyketide producing microorganism and altered or arranged with other sugar biosynthesis genes and then introduced into the same or another polyketide producing microorganism to create a novel glycosylated polyketide of predicted structure. Thus, for example, a Type I or Type II alteration of a heterologous gene that is similar to an eryB and/or eryC gene, such as can be found in the eryBVII homolog for the synthesis of L-oleandrose in *Streptomyces antibioticus*, to result in the production of 3-des-L-oleandrosyl-3-D-oleandrosyl oleandomycin is included within the scope of the present invention. Similarly, a Type III assembly of the genes for the synthesis of a sugar other than mycarose or desosamine, such as can be found in the genes for the synthesis of angolosamine in *Streptomyces eurythermus*, and their transformation into *Sac. erythraea* to result in the synthesis of 5-des-desosaminoyl-5-angolosaminoyl-erythromycin A is included within the scope of the present invention.

It will occur to those skilled in the art that the Type I, Type II, and Type III genetic manipulations described herein and the polyketide producing microorganisms into which they are introduced are in no way exclusive. Hence, the choice of a convenient host and the choice of a Type I, Type II, or Type III alteration is based solely on the relatedness of the desired novel glycosylated polyketide to a natural counterpart. Therefore, Type I, Type II, and Type III alterations can be constructed in any polyketide producing microorganism employing either endogenous or exogenous sugar biosynthesis genes. Thus all Type I, Type II, and Type III mutations or various combinations thereof constructed in any polyketide producing microorganism according to the principles described herein, and the respective polyketides produced from such strains, are included within the scope of the present invention. Examples of glycosylated polyketides that can be altered by creating Type I, Type II, or Type III changes in the producing microorganisms include, but are not limited to macrolide antibiotics such as erythromycin, tylosin, spiramycin, etc; aromatic polyketides such as daunorubicin and doxorubicin, etc; polyenes such as candicidin, amphotericins, etc; and other complex polyketides such as avermectin.

Whereas the novel derivatives or modifications of erythromycin described herein have been specified as the A derivatives, such as 4"-deoxy-4"-oxo-erythromycin A, those skilled in the art understand that the wild type strain of *Sac. erythraea* produces a family of erythromycin compounds, including erythromycin A, erythromycin B, erythromycin C, and erythromycin D. Thus, modified strains of *Sac. erythraea*, such as strain ERBIV, for example, would be expected to produce the corresponding members of the 4"-deoxy 4"-oxo-erythromycin family, including 4"-deoxy-4"-oxo-erythromycin A, 4"-deoxy-4"-oxo-erythromycin B, 4"-deoxy-4"-oxo-erythromycin C, and 4"-deoxy-4"-oxo-erythromycin D. Similarly, all other modified strains of *Sac. erythraea* that produce novel glycosylated erythromycin derivatives would be expected to produce the A, B, C, and D forms of said derivatives. For example, modified *Sac. erythraea* strains that produce 6-deoxyerythromycin, 6,12-dideoxyerythromycin and 6,7-anhydroerythromycin would be expected to produce novel glycosylation-modified polyketides by introduction of the additional modification of a Type I, II or III change in a sugar biosynthesis gene. Therefore, all members of the family of each of the novel erythromycins described herein or produced by these methods are included within the scope of the present invention.

Variations and modifications of the methods for obtaining the desired plasmids, hosts for cloning and choices of vectors and eryB and/or eryC genes to clone and modify, other than those described herein will occur to those skilled in the art. For example, although we have described the use of plasmids pWHM3, pWHM4, and pIJ702, other vectors can be employed wherein all or part of said plasmids is replaced by other DNA segments that function in a similar manner, such as replacing the pUC19 component of pWHM3 and pWHM4 with pBR322, available from BRL; or employing different segments of the pIJ101 replicon in pWHM3 and pIJ702, or the pJV1 replicon in pWHM4, respectively; or employing selectable markers other than thiostrepton- or ampicillin-resistance. These are just a few of a long list of possible examples all of which are included within the scope of the present invention. Similarly, the segments of the eryB and eryC loci that have been specified herein to generate the various Type I, Type II, and Type III alterations can readily be substituted for other segments of different length encoding the same functions, either produced by PCR-amplification of genomic DNA or of an isolated clone, or by isolating suitable restriction fragments from *Sac. erythraea*. In the same way it is possible to create Type I mutations functionally equivalent to those described herein by altering through deletion, insertion, or site directed mutagenesis different portions of the corresponding genes. It is also possible to create Type II mutations functionally equivalent to those described herein by employing larger or smaller portions of the corresponding genes; and it is possible to create Type III mutations using larger or smaller segments of the corresponding genes in the same or different linear order described herein. Additional modifications include changes in the restriction sites used for cloning or in the general methodologies described above. All such changes are included in the scope of the present invention. It will also occur to those skilled in the art that different methods are available to ferment *Sac. erythraea* and other polyketide producing microorganisms and to extract the novel polyketides specified herein, and all such methods are also included within the scope of this invention.

It will also be apparent that many modifications and variations of the invention as set forth herein are possible without departing from the spirit and scope thereof, and that, accordingly, such limitations are imposed only as indicated by the appended claims.

We claim:

1. An isolated single or double stranded polynucleotide which comprises a nucleotide sequence selected from the group consisting of a) the sense sequence of SEQ ID NO:1 wherein said sense sequence of SEQ ID NO:1 is selected from the group consisting of (i) from about nucleotide position 54 to about nucleotide position 1136; (ii) from about nucleotide position 1147 to about nucleotide position 2412; and (iii) from about nucleotide position 2409 to about nucleotide position 3410;

b) the sense sequence of SEQ ID NO:2 wherein said sense sequence of SEQ ID NO:2 is selected from the group consisting of (i) from about nucleotide position 80 to about nucleolide position 1048; (ii) from about nucleotide position 1048 to about nucleotide position 2295; (iii) from about nucleotide position 2348 to about nucleotide position 3061; (iv) from about nucleotide position 3214 to about nucleotide position 4677; (v) from about nucleotide position 4674 to about nucleotide position 5879; (vi) from about nucleotide position 5917 to about nucleotide position 7386; and (vii) from about nucleotide position 7415 to about nucleotide position 7996;

c) sequences complementary to the sequences of (a) or (b); and d) sequences that, on expression, encode a polypeptide encoded by the sequences of (a) or (b).

2. The polynucleotide of claim 1 that is a DNA molecule.

3. The polynucleotide of claim 1 that is an RNA molecule.

4. The polynucleotide of claim 2 wherein the nucleotide sequence is selected from the group consisting of the nucleotide sequence of (a) selected from the group consisting of (i) from about nucleotide position 54 to about nucleotide position 1136; and (ii) from about nucleotide position 1147 to about nucleotide position 2412; and the nucleotide sequence of (b) selected from the group consisting of (i) from about nucleotide position 2348 to about nucleotide position 3061; (ii) from about nucleotide position 4674 to about nucleotide position 5879; and (iii) from about nucleotide position 5917 to about nucleotide position 7386.

5. The polynucleotide of claim 2 wherein the nucleotide sequence is selected from the group consisting of the nucleotide sequence of (a) from about nucleotide position 2409 to about nucleotide position 3410; and the nucleotide sequence of (b) selected from the group consisting of (i) from about nucleotide position 80 to about nucleotide position 1048; from about nucleotide position 1048 to about nucleotide position 2295; (iii) from about nucleotide position 3214 to about nucleotide position 4677; and (iv) from about nucleotide position 7415 to about nucleotide position 7996.

6. The polynucleotide of claim 2 wherein the nucleotide sequence is the nucleotide sequence of (b) from about nucleotide position 80 to about nucleotide position 1048.

7. A vector comprising the DNA molecule of claim 2.

8. The vector of claim 7 further comprising an enhancer-promoter operatively linked to the polynucleotide.

9. The vector of claim 7 wherein the polynucleotide has the nucleotide sequence of claim 6.

10. A host cell transformed with the vector of claim 7.

11. The transformed host cell of claim 10 that is a bacterial cell.

12. The transformed host cell of claim 11 wherein the bacterial cell is selected from the group consisting of Streptomyces and E. coli.

13. A host cell transformed with the vector of claim 8.

14. The transformed host cell of claim 13 that is a bacterial cell.

15. The transformed host cell of claim 14 wherein the bacterial cell is selected from the group consisting of Streptomyces and E. coli.

16. A host cell transformed with the vector of claim 9.

17. The transformed host cell of claim 16 that is a bacterial cell.

18. The transformed host cell of claim 17 wherein the bacterial cell is selected from the group consisting of Streptomyces and E. coli.

19. A method for directing the biosynthesis of specific glycosylation-modified polyketides by genetic manipulation of a polyketide-producing microorganism, said method comprising the steps of:

(1) isolating a sugar biosynthesis gene-containing DNA sequence according to claim 1;

(2) identifying within said gene-containing DNA sequence one or more DNA fragments responsible for the biosynthesis of a polyketide-associated sugar or its attachment to a polyketide;

(3) introducing said DNA fragment or fragments into a distinct polyketide-producing microorganism to produce an altered polyketide-producing microorganism capable of producing said specific glycosylation-modified polyketide;

(4) growing a culture of said polyketide-producing microorganism containing said DNA fragment or fragments under conditions suitable for the formation of said specific glycosylation-modified polyketide; and (6) isolating said specific glycosylation-modified polyketide from said culture.

* * * * *